United States Patent
Heil et al.

(10) Patent No.: US 9,120,787 B2
(45) Date of Patent: Sep. 1, 2015

(54) HIV REPLICATION INHIBITORS

(75) Inventors: Marintha L. Heil, Frederick, MD (US); Nicholas D. P. Cosford, La Jolla, CA (US); Nicholas Pagano, La Jolla, CA (US); Peter Teriete, La Jolla, CA (US)

(73) Assignees: Southern Research Institute, Birmingham, AL (US); Sanford-Burnham Medical Research Institute, La Jolla, CA (US)

( * ) Notice: Subject to any disclaimer, the term of this patent is extended or adjusted under 35 U.S.C. 154(b) by 0 days.

(21) Appl. No.: 14/238,374

(22) PCT Filed: Aug. 27, 2012

(86) PCT No.: PCT/US2012/052482
§ 371 (c)(1),
(2), (4) Date: Apr. 2, 2014

(87) PCT Pub. No.: WO2013/033003
PCT Pub. Date: Mar. 7, 2013

(65) Prior Publication Data
US 2014/0235582 A1 Aug. 21, 2014

Related U.S. Application Data

(60) Provisional application No. 61/527,895, filed on Aug. 26, 2011.

(51) Int. Cl.
*C07D 239/22* (2006.01)
*C07D 417/04* (2006.01)
*C07D 417/14* (2006.01)
*A61K 31/513* (2006.01)
*A61K 31/675* (2006.01)
*A61K 45/06* (2006.01)

(52) U.S. Cl.
CPC ............ *C07D 417/14* (2013.01); *A61K 31/513* (2013.01); *A61K 31/675* (2013.01); *A61K 45/06* (2013.01); *C07D 239/22* (2013.01); *C07D 417/04* (2013.01)

(58) Field of Classification Search
CPC .. C07D 239/22; C07D 417/04; C07D 417/14; A61K 31/513; A61K 31/675
USPC ........... 544/295, 296, 315, 316; 514/249, 274
See application file for complete search history.

(56) References Cited

FOREIGN PATENT DOCUMENTS

| CN | 1500082 A | 5/2004 |
|----|-----------|--------|
| CN | 101903356 A | 12/2010 |
| WO | WO-2005110411 A1 | 11/2005 |
| WO | WO-2010046780 A2 | 4/2010 |

OTHER PUBLICATIONS

Pagano et al., An Automated Process for a Sequential Heterocycle/Multicomponent Reaction: Multistep Continuous Flow Synthesis of 5-(Thiazol-2-yl)-3,4-Dihydropyrimidin-2(1H)-ones, Journal of Flow Chemistry, vol. 1, No. 1, pp. 28-31 (Aug. 25, 2011).*
Gray et al., Preexposure Prophylaxis for HIV Prevention, The New England Journal of Medicine, pp. 462-465 (2012).*
Kharchenko et al., Synthesis of Substituted 5-(1,2,4-oxadiazol-5-yl)-3,4-dihydropyrimidine-2(1H)-thiones, J. Comb. Chem. 11, pp. 216-219 (2009).*
Nadery et al., Pre-exposure prophylaxis (PrEP) in HIV-uninfected individuals with high-risk behaviour, Netherlands Journal of Medicine, 71(6), pp. 295-299 (2013).*
Razonable et al., PubMed Abstract (Herpes 10(3):60-5) (2003).*
Padhy et al., Synthesis and anti-microbial activity of some pyrimidine derivatives, Indian Journal of Chemistry, vol. 42B, pp. 910-915 (Apr. 2003).*
Goff, Medline Abstract (J. Gene Med. 3(6):517-28) (2001).*
Douglas et al., Introduction to Viral Diseases, Cecil Textbook of Medicine, $20^{th}$ Edition, vol. 2, pp. 1739-1747 (1996).*
Bosseray et al., PubMed Abstract (Pathol Biol (Paris) 50(8):483-92) (2002).*
Mishra et al., "Synthesis and Anti-microbial Evaluation of Some 3, 4-Dihydro Pyrimidine-2-one Derivatives", Trends in Applied Sciences Research, 3 (2): 203-208, 2008.
Extended European Search Report issued Aug. 12, 2014 in EP Appln. No. EP12828488.
First Office Action issued Oct. 24, 2014 in Chinese Appln. No. 201280041536.7.
Parameswari et al., "Adsorption and Inhibitive Properties of Triazolopyrimidine Derivatives in Acid Corrosion of Mild Steel", E-Journal of Chemistry, 2011, 8(3), 1250-1257.
Registry (STN) [online], Jan. 27, 2011 CAS registry No. 1260732-94-2.
Registry (STN) [online], Aug. 7, 2009 CAS registry No. 1173247-19-2.
Registry (STN) [online], Aug. 5, 2009 CAS registry No. 1172858-78-4.
Registry (STN) [online], Jul. 29, 2009 CAS registry No. 1170040-00-2.
Registry (STN) [online], Aug. 2, 2009 CAS registry No. 1171615-64-7.
Registry (STN) [online], Jul. 12, 2006 CAS registry No. 892302-22-6.
Registry (STN) [online], Aug. 13, 2008 CAS registry No. 1040705-90-5.
Registry (STN) [online], Aug. 13, 2008 CAS registry No. 1040703-90-9.
Registry (STN) [online], Aug. 13, 2008 CAS registry No. 1040701-84-5.
Registry (STN) [online], Jan. 26, 2008 CAS registry No. 1030782-61-6.
Office Action issued Jun. 2, 2015 in JP Application No. 2014-527351.

* cited by examiner

*Primary Examiner* — Deepak Rao
(74) *Attorney, Agent, or Firm* — Novak Druce Connolly Bove + Quigg LLP

(57) ABSTRACT

Compounds of Formula (I) wherein B is selected from the group consisting of substituted or unsubstituted aryl, substituted or unsubstituted heteroaryl; Y is a linker moiety selected from the group consisting of a direct bond. R, R1, R2, and R3 are each individually selected from the group consisting substituted or unsubstituted aryl, substituted or unsubstituted heteroaryl, or heterocycle.

19 Claims, 2 Drawing Sheets

*Scheme 5.* One-pot synthesis of 5-(thiazol-2-yl)-3,4-dihydrpyrimidin-2(*1H*)-ones.

*Scheme 6.* Continuous flow synthesis of 5-(thiazol-2-yl)-3,4-dihydropyrimidin-2(*1H*)-ones.

Scheme 7. Example of continuous flow synthesis.

HIV REPLICATION INHIBITORS

CROSS REFERENCE TO RELATED APPLICATIONS

This application is a National Phase filing under 35 U.S.C. §371 of PCT/US2012/052482 filed on Aug. 27, 2012; and this application claims priority to U.S. Provisional Application No. 61/527,895 filed on Aug. 26, 2012; the entire contents of all are hereby incorporated by reference.

FEDERALLY SPONSORED RESEARCH AND DEVELOPMENT

This invention was partially supported by grants No. MH087989, DA029966 and CA030199 from the National Institutes of Health and the US Government has certain rights in the invention.

BACKGROUND

1. Technical Field

This disclosure generally relates to compounds and compositions, and methods of using these compounds and compositions, as inhibitors of human immunodeficiency virus (HIV) replication, and methods of treating patients infected with HIV, the causative agent of acquired immunodeficiency syndrome (AIDS). The present disclosure also relates to pre-exposure prophylaxis. In addition, the present disclosure relates to methods for fabricating compounds according to the disclosure.

2. Background Information

The human immunodeficiency virus (HIV) is the causative agent of acquired immunodeficiency syndrome (AIDS), a life threatening disease for which there is no cure. Since its discovery 30-years ago, there have been over 60 million people that have been infected with HIV and 25 million have died of HIV related causes. As of 2009, there were an estimated 33.3 million people living with the disease and 1.8 million new infections worldwide per year[1].

The advent of highly active anti-retroviral therapy (HAART) for the chronic suppression of virus replication has dramatically increased the mean survival time and improved quality of life for individuals infected with HIV. More recently, pre-exposure prophylactic administration of anti-retroviral therapy has been provided to healthy individuals at high risk of contracting the disease to prevent infection. Pre-exposure prophylaxis (PrEP) studies have shown a reduction in the rate of transmission to 1.7 in every 100 children in mother-to-child transmission and 44 out of every 100 events in cohorts of men who have sex with men[2-6].

HIV is a positive sense RNA virus. The viral genome is ~10,000 bp and encodes viral capsid, nucleocapsid, matrix, reverse transcriptase (RT), protease, envelope proteins (Gp120 & Gp41), integrase, Tat, Rev, Vif, Vpu and Nef. A host cell is infected when HIV gp120 binds the host CD4 receptor. Next, the virus binds the CCR5, or CXCR4, co-receptor and undergoes a conformational change, forming a prefusion complex with the host cell, which folds to merge the virus and host cell lipid membranes. Once inside the cell, the virus uncoats and the RT primes the viral RNA genome for transcription of a DNA copy of the genome. The DNA copy of the genome is integrated by the viral integrase into the host genome. The integrated genome is transcribed by the host polymerase machinery and the virus protein Tat. The viral protein Rev binds the newly transcribed full length RNA and the complex is exported from the nucleus into the cytoplasm. In the cytoplasm, the viral genome is translated and processed by the viral protease. The nucleocapsid and capsid surround the viral genome and the newly formed virion buds from the infected cells.

There are over 30 FDA-approved drugs for the treatment of HIV. The viral proteins successfully targeted by these drugs include RT, protease, gp41 and integrase. Inhibitors of the HIV RT and proteases are the most numerous of the FDA-approved drugs. They are part of the first and second line of treatment regimens[7-9]. The current evidence supports the combination of 2 nucleoside reverse transcriptase inhibitors (NRTIs) and a potent third agent from another class including non-nucleoside reverse transcriptase inhibitors (NNRTIs)[10]. The use of NRTIs and NNRTIs in PrEP has reduced transmission from an infected individual to non-infected individual[2,4-6]. Specifically, 1. Nevaripine, AZT and lamivudine have been shown to prevent transmission from mother-to-child[5]; and
2. Emtricidine and tenofovir have been shown to prevent infection in discordant sexual transmissions in an oral formulation in a cohort of men who have sex with men[2,4].

Drug resistance to the HIV anti-viral drugs is well documented and is summarized biannually[11]. In the absence of a preventative vaccine and/or cure, new infections and lifelong anti-retroviral therapy will be a reality and mandates new antiviral agents to combat therapy resistant viruses.

SUMMARY OF DISCLOSURE

Disclosed are certain compounds that prevent the replication of HIV-1. Compounds according to this disclosure have been identified that inhibit the replication of HIV-1 in a dose-dependent manner in cell culture assays, and confirmed to dose-dependently inhibit HIV replication in peripheral blood mononuclear cells (PBMC) utilizing a viral RT end-point.

In another embodiment of the present disclosure compounds are provided which inhibit HIV replication through a mechanism of action that involves inhibiting the viral RT enzyme. The compounds of the invention have activity against HIV-1$_{Ba-L}$.

In another embodiment of the present disclosure compounds are provided which inhibit the replication of HIV strains resistant to NNRTIs. Compounds in this disclosure inhibit, A17, an HIV-1 virus with mutations in the RT non-nucleoside binding pocket, K103N and Y181C, in a dose-dependent susceptibility testing manner. Compounds of the present disclosure exhibit good stability.

The disclosure provides compounds and compositions, and methods of using these compounds and compositions, as inhibitors of human immunodeficiency virus (HIV) replication. The disclosed compounds and compositions are useful for treating patients infected with HIV, the causative agent of acquired immunodeficiency syndrome (AIDS).

Thus, in one embodiment this disclosure provides compounds of Formula I:

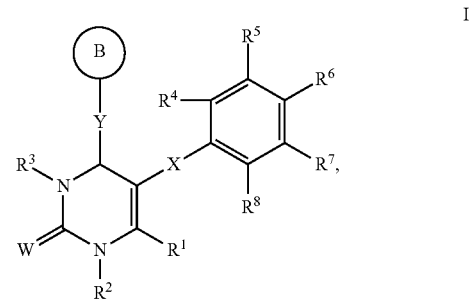

wherein B is selected from the group consisting of substituted or unsubstituted aryl, substituted or unsubstituted heteroaryl; W is O, S, or NR;

Y is a linker moiety selected from the group consisting of a direct bond, O, S, NR, $C_1$-$C_8$ alkyl, $C_2$-$C_8$ alkenyl, $C_2$-$C_8$ alkynyl, $C_1$-$C_8$ alkoxy, $C_1$-$C_8$ thioalkyl, $C_1$-$C_8$ alkylNR;

R, $R^1$, $R^2$, and $R^3$ are each individually selected from the group consisting of H, $C_1$-$C_8$ alkyl, $C_1$-$C_8$ haloalkyl, $C_1$-$C_8$ alkylaryl, $C_{2-8}$ alkenyl, $C_{2-8}$ alkynyl, cycloalkyl, substituted or unsubstituted aryl, substituted or unsubstituted heteroaryl, or heterocycle;

X is

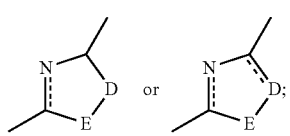

D and E are each individually selected from the group consisting of O, S, $NR^9$, CR or $CR^1R^2$;

$R^9$ is selected from the group consisting of H, $C_1$-$C_8$ alkyl, $C_1$-$C_8$ haloalkyl, $C_3$-$C_8$ cycloalkyl, $C_2$-$C_8$ alkenyl, $C_2$-$C_8$ alkynyl, $C_5$-$C_{10}$ aryl, $C_5$-$C_{10}$ heterocycle each of which is optionally substituted with halogen, —$OR^{10}$, —$NR^{11}R^{12}$, —$SR^{11}$, —$S(O)R^{11}$, —$S(O)_2R^{12}$, or —$S(O)_2NR^{11}R^{12}$;

$R^4$, $R^5$, $R^6$, $R^7$, and $R^8$ are each are independently selected from H, hydroxyl, halogen, cyano, $NO_2$, —$OR^{10}$, —$SR^{11}$, —$S(O)R^{11}$, —$S(O)_2R^{12}$, —$S(O)_2NR^{11}R^{12}$, $C_1$-$C_8$ haloalkyl, $COR^{13}$, —$C(O)OR^{12}$, —$C(O)NR^{11}R^{12}$, —$C(O)R^{12}$, —$NR^{11}R^{12}$, —$NR^{11}C(O)R^{12}$, —$NR^{11}S(O)_2R^{12}$, —$NR^{11}C(O)OR^{12}$, —$B(OH)_2$, $C_1$-$C_8$ alkyl, $C_3$-$C_8$ cycloalkyl, $C_2$-$C_8$ alkenyl, $C_2$-$C_8$ alkynyl, substituted or unsubstituted aryl, substituted or unsubstituted heteroaryl, -alkylC(O)—$OR^{12}$, -alkylC(O)$NR^{11}R^{12}$, -alkenylC(O)$OR^{12}$, -alkenylC(O)$NR^{11}R^{12}$, -aryl$(CH_2)_mX(O)OR^{12}$, -aryl$(CH_2)_mC(O)NR^{11}R^{12}$, —$(CH_2)_mC(O)NR^{11}S(O)_2R^{12}$, -aryl$(CH_2)_m$—$C(O)NR^{11}S(O)_2R^{12}$, —$(CH_2)_mS(O)_2NR^{11}C(O)R^{12}$, -aryl$(CH_2)_mS(O)_2NR^{11}C(O)R^{12}$, or substituted or unsubstituted heterocycle or substituted or unsubstituted heteroaryl containing 1 to 4 heteroatoms, optionally substituted with 1 to 2 substituents selected from the group consisting of H, hydroxyl, halogen, $CF_3$, $C_1$-$C_8$ alkyl, $C_1$-$C_8$ alkoxy, cyano, amino, $C_1$-$C_8$ alkylamino, and $C_1$-$C_8$ alkoxy$C_1$-$C_8$ alkylamino provided at least one of $R^4$, $R^5$, $R^6$, $R^7$, or $R^8$ is other than hydrogen;

$R^{10}$, $R^{11}$, $R^{12}$, and $R^{13}$ are each individually selected from the group consisting of H, $C_1$-$C_8$ alkyl, $C_1$-$C_8$ haloalkyl, $C_1$-$C_8$ alkylaryl, $C_{2-8}$ alkenyl, $C_{2-8}$ alkynyl, cycloalkyl, substituted or unsubstituted aryl, substituted or unsubstituted heteroaryl, or heterocycle;

m=0 to 6;

wherein alkyl, alkenyl, alkynyl, cycloalkyl, aryl, heteroaryl or heterocycle may be substituted or unsubstituted;

pharmaceutically acceptable salt thereof; solvate thereof and deuterated form thereof.

In another embodiment, the disclosure provides a method for inhibiting HIV-1 replication in patients by administering an effective HIV-1 replication inhibiting amount of a compound of Formula I, pharmaceutically acceptable salt thereof or solvate thereof to a subject in need thereof. According to this embodiment, the disclosure provides compounds that inhibit HIV-1 replication as demonstrated by reduction in virus released from Magi-CCR5 and PBMCs (RT end-point). Compounds of the invention act by inhibiting the HIV-1 RT as demonstrated by the ability to inhibit RT activity in a biochemical assay. Compounds of the present disclosure act by inhibiting HIV strains resistant to NNRTI's.

In another embodiment, the disclosure provides a method for treating patients infected with HIV/AIDS, either by administering a compound of Formula I, pharmaceutically acceptable salt thereof or solvates thereof to a subject in need thereof alone or in combination with existing standard of care treatments (NRTIs, NNRTIs, protease inhibitors, integrase inhibitors, CCR5 antagonists and the like).

In another embodiment, the disclosure provides a pre-exposure prophylaxis method for treating a patient and for the prevention of transmission from an infected person to an uninfected person by administering to a patient in need thereof a therapeutically effective amount of a compound of Formula I, pharmaceutically acceptable salt thereof or solvate thereof. Examples of prophylaxis treatments are treating a pregnant women or one in labor, who has been infected to protect the unborn; treating women who are nursing to protect the child, and prevention of infection in same sex and hetero sex relations.

Still other objects and advantages of the present disclosure will become readily apparent by those skilled in the art from the following detailed description, wherein it is shown and described only the preferred embodiments, simply by way of illustration of the best mode. As will be realized, the disclosure is capable of other and different embodiments, and its several details are capable of modifications in various obvious respects, without departing from the disclosure. Accordingly, the description is to be regarded as illustrative in nature and not as restrictive.

BEST AND VARIOUS MODES FOR CARRYING OUT DISCLOSURE

Figure 1:
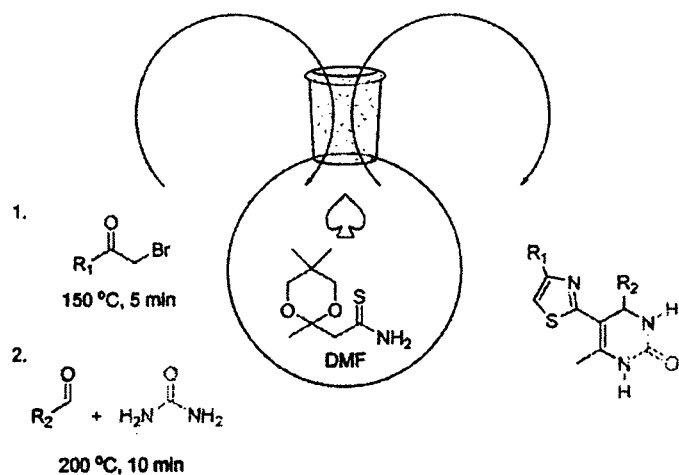
FIG. 1 illustrates Scheme 5, which is a one-pot synthesis of 5-(thiazol-2-yl)-3,4-dihydropyrimidin-2(1H)-ones.

Compounds according this disclosure can be represented by the following Formula I:

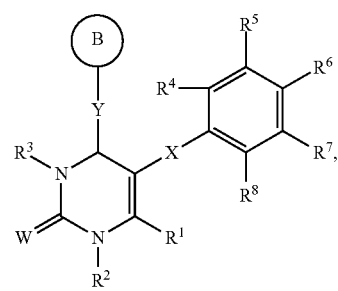

wherein B is selected from the group consisting of substituted or unsubstituted aryl, substituted or unsubstituted heteroaryl;

W is O, S, or NR;

Y is a linker moiety selected from the group consisting of a direct bond, O, S, NR, $C_1$-$C_8$ alkyl, $C_2$-$C_8$ alkenyl, $C_2$-$C_8$ alkynyl, $C_1$-$C_8$ alkoxy, $C_1$-$C_8$ thioalkyl, $C_1$-$C_8$ alkylNR;

R, $R^1$, $R^2$, and $R^3$ are each individually selected from the group consisting of H, $C_1$-$C_8$ alkyl, $C_1$-$C_8$ haloalkyl, $C_1$-$C_8$ alkylaryl, $C_{2-8}$ alkenyl, $C_{2-8}$ alkynyl, cycloalkyl, substituted or unsubstituted aryl, substituted or unsubstituted heteroaryl, or heterocycle;

X is

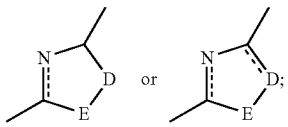

D and E are each individually selected from the group consisting of O, S, $NR^9$, CR or $CR^1R^2$;

$R^9$ is selected from the group consisting of H, $C_1$-$C_8$ alkyl, $C_1$-$C_8$ haloalkyl, $C_3$-$C_8$ cycloalkyl, $C_2$-$C_8$ alkenyl, $C_2$-$C_8$ alkynyl, $C_5$-$C_{10}$ aryl, $C_5$-$C_{10}$ heterocycle each of which is optionally substituted with halogen, $-OR^{10}$, $-NR^{11}R^{12}$, $-SR^{11}$, $-S(O)R^{11}$, $-S(O)_2R^{12}$, or $-S(O)_2NR^{11}R^{12}$;

$R^4$, $R^5$, $R^6$, $R^7$, and $R^8$ are each are independently selected from H, hydroxyl, halogen, cyano, $NO_2$, $-OR^{10}$, $-SR^{11}$, $-S(O)R^{11}$, $-S(O)_2R^{12}$, $-S(O)_2NR^{11}R^{12}$, $C_1$-$C_8$ haloalkyl, $COR^{13}$, $-C(O)OR^{12}$, $-C(O)NR^{11}R^{12}$, $-C(O)R^{12}$, $-NR^{11}R^{12}$, $-NR^{11}C(O)R^{12}$, $-NR^{11}S(O)_2R^{12}$, $-NR^{11}C(O)OR^{12}$, $-B(OH)_2$, $C_1$-$C_8$ alkyl, $C_3$-$C_8$ cycloalkyl, $C_2$-$C_8$ alkenyl, $C_2$-$C_8$ alkynyl, substituted or unsubstituted aryl, substituted or unsubstituted heteroaryl, -alkylC(O)$-OR^{12}$, -alkylC(O)$NR^{11}R^{12}$, -alkenylC(O)$OR^{12}$, -alkenylC(O)$NR^{11}R^{12}$, -aryl($CH_2$)$_m$C(O)$OR^{12}$, -aryl($CH_2$)$_m$C(O)$NR^{11}R^{12}$, $-(CH_2)_mC(O)NR^{11}S(O)_2R^{12}$, -aryl($CH_2$)$_m$$-$C(O)$NR^{11}S(O)_2R^{12}$, $-(CH_2)_mS(O)_2NR^{11}C(O)R^{12}$, -aryl $(CH_2)_mS(O)_2NR^{11}C(O)R^{12}$, or substituted or unsubstituted heterocycle or substituted or unsubstituted heteroaryl containing 1 to 4 heteroatoms, optionally substituted with 1 to 2 substituents selected from the group consisting of H, hydroxyl, halogen, $CF_3$, $C_1$-$C_8$ alkyl, $C_1$-$C_8$ alkoxy, cyano, amino, $C_1$-$C_8$ alkylamino, and $C_1$-$C_8$ alkoxy$C_1$-$C_8$ alkylamino provided at least one of $R^4$, $R^5$, $R^6$, $R^7$, or $R^8$ is other than hydrogen;

$R^{10}$, $R^{11}$, $R^{12}$, and $R^{13}$ are each individually selected from the group consisting of H, $C_1$-$C_8$ alkyl, $C_1$-$C_8$ haloalkyl, $C_1$-$C_8$ alkylaryl, $C_{2-8}$ alkenyl, $C_{2-8}$ alkynyl, cycloalkyl, substituted or unsubstituted aryl, substituted or unsubstituted heteroaryl, or heterocycle;

m=0 to 6;

wherein alkyl, alkenyl, alkynyl, cycloalkyl, aryl, heteroaryl or heterocycle may be substituted or unsubstituted;

pharmaceutically acceptable salt thereof; solvate thereof and deuterated form thereof.

According to certain more preferred embodiments, the present disclosure relates to compounds represented by formula II:

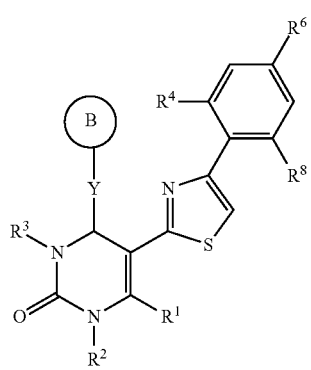

wherein B is selected from the group consisting of substituted or unsubstituted pyridinyl and when substituted the substitution is halo or $C_1$-$C_6$ alkoxy in the ortho position to the nitrogen in the pyridinyl ring or can be halo in the meta position when the nitrogen is in the 2-position; mono-substituted or unsubstituted quinolinyl and when substituted the substitution is hydroxyl; mono-substituted or unsubstituted indolyl and when substituted the substitution is $C_1$-$C_6$ alkyl; unsubstituted benzothiophenyl; unsubstituted thiophenyl; mono-substituted, or di-substituted or unsubstituted phenyl and when substituted the substitution is selected from the group consisting of hydroxyl, halo, CN, $CF_3$, $C_1$-$C_4$ alkoxy, and aryloxy; provided that when the phenyl is di-substituted the substitutions are located ortho to each other; and unsubstituted biphenyl;

Y is a direct bond or Y can be a $C_1$-$C_6$ alkyl when $R^5$ is CN;

$R^1$ is H, $C_1$-$C_6$ alkyl or $C_{3-8}$ cycloalkyl and more typically is H or $C_1$-$C_6$ alkyl;

$R^2$ is H, $C_1$-$C_6$ alkyl or $C_{3-8}$ cycloalkyl and more typically is H or $C_1$-$C_6$ alkyl;

$R^3$ is H;

each of $R^4$ and $R^8$ is independently H, $C_1$-$C_6$ alkyl or $C_{3-8}$ cycloalkyl and more typically is H or $C_1$-$C_6$ alkyl;

$R^6$ is selected from the group consisting of CN, $NO_2$, aryloxy, and halo;

pharmaceutically acceptable salts thereof solvates thereof and deuterated form thereof.

Still other aspects to the present disclosure relate to compounds represented by formula III:

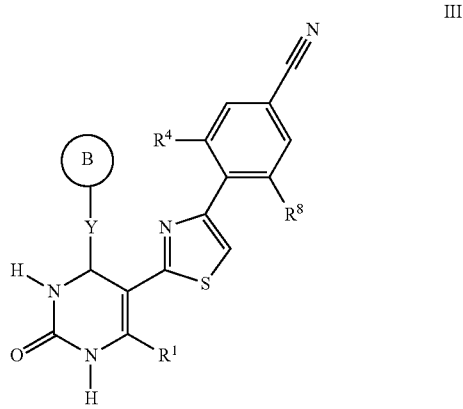

wherein $R^1$ is H, $C_1$-$C_6$ alkyl or $C_{3-8}$ cycloalkyl, more typically $C_1$-$C_6$ alkyl and even more typically methyl; $R^4$ and $R^8$ are each independently H, $C_1$-$C_6$ alkyl or $C_{3-8}$ cycloalkyl;

and B is selected from the group consisting of phenyl substituted with at least one member selected from the group consisting hydroxyl, halo, $C_1$-$C_6$ alkoxy, aryloxy; pyridyl substituted with at least one member selected from the group consisting halo and $C_1$-$C_6$ alkoxy and indolyl substituted with a $C_1$-$C_6$ alkyl group.

The term "alkyl" refers to straight or branched chain unsubstituted hydrocarbon groups of typically 1 to 22 carbon atoms, more typically 1 to 8 carbon atoms, even more typically 1 to 6 carbon atoms and even still more typically 1 to 4 carbon atoms.

Examples of suitable alkyl groups include methyl, ethyl and propyl. Examples of branched alkyl groups include isopropyl and t-butyl.

The alkoxy group typically contains 1 to 6 carbon atoms. Suitable alkoxy groups typically contain 1-6 carbon atoms and include methoxy, ethoxy, propoxy and butoxy.

Examples of halo groups are Cl, F, Br and I.

The term "aryl" refers to monocyclic or bicyclic aromatic hydrocarbon groups having 6 to 12 carbon atoms in the ring portion, such as phenyl, naphthyl, biphenyl, and diphenyl groups. The aryl can be optionally substituted as described above for aryl, including substituted with one or more substituents selected from hydroxyl, amino, alkylamino, arylamino, alkoxy, aryloxy, alkyl, heterocycle, halo, carboxy, acyl, acyloxy, amido, nitro, cyano, sulfonic acid, sulfate, phosphonic acid, phosphate, or phosphonate, either unprotected, or protected as necessary, as known to those skilled in the art, for example, as taught in Greene, et al., *Protective Groups in Organic Synthesis*, John Wiley and Sons, Second Edition, 1991.

The term "cycloalkyl" refers cyclic hydrocarbon ring systems typically containing 3-8 carbon atoms and more typically 3 to 6 carbon atoms, with typical examples being cyclopropyl, cyclobutyl, cyclopentyl, and cyclohexyl.

Suitable alkenyl groups typically contain 2-8 carbon atoms, more typically 2-6 carbon atoms and include ethenyl and propenyl.

Suitable alkynyl groups typically contain 2-8 carbon atoms, more typically 2-6 carbon atoms and include ethynyl and propynyl.

The terms "heterocycle", "heterocyclic" and "heterocyclo" refer to an optionally substituted, fully saturated or unsaturated, aromatic or nonaromatic cyclic group, for example, which is a 4 to 7 membered monocyclic, 7 to 11 membered bicyclic, or 10 to 15 membered tricyclic ring system, which has at least one heteroatom and at least one carbon atom in the ring. Each ring of the heterocyclic group containing a heteroatom may have 1, 2 or 3 heteroatoms selected from nitrogen atoms, oxygen atoms and sulfur atoms, where the nitrogen and sulfur heteroatoms may also optionally be oxidized and the nitrogen heteroatoms may also optionally be quaternized. The heterocyclic group may be attached at any heteroatom or carbon atom. Examples of heterocycles and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), piperidinyl, pyrrolidine, tetrahydrofuranyl, furyl, furanyl, pyridyl, pyrimidyl, thienyl, isothiazolyl, imidazolyl, tetrazolyl, pyrazinyl, benzofuranyl, benzothiophenyl, quinolyl, isoquinolyl, benzothienyl, isobenzofuryl, pyrazolyl, indolyl, isoindolyl, benzimidazolyl, purinyl, carbazolyl, oxazolyl, thiazolyl, isothiazolyl, 1,2,4-thiadiazolyl, isooxazolyl, pyrrolyl, quinazolinyl, cinnolinyl, phthalazinyl, xanthinyl, hypoxanthinyl, thiophene, furan, isopyrrole, 1,2,3-triazole, 1,2,4-triazole, oxazole, thiazole, pyrimidine, aziridines, thiazole, 1,2,3-oxadiazole, thiazine, pyrrolidine, oxaziranes, morpholinyl, pyrazolyl, pyridazinyl, pyrazinyl, quinoxalinyl, xanthinyl, hypoxanthinyl, pteridinyl, 5-azacytidinyl, 5-azauracilyl, triazolopyridinyl, imidazolopyridinyl, pyrrolopyrimidinyl, pyrazolopyrimidinyl, adenine, N6-alkylpurines, N6-benzylpurine, N6-halopurine, N6-vinypurine, N6-acetylenic purine, N6-acyl purine, N6-hydroxyalkyl purine, N6-thioalkyl purine, thymine, cytosine, 6-azapyrimidine, 2-mercaptopyrmidine, uracil, N5-alkyl-pyrimidines, N5-benzylpyrimidines, N5-halopyrimidines, N5-vinyl-pyrimidine, N5-acetylenic pyrimidine, N5-acyl pyrimidine, N5-hydroxyalkyl purine, and N6-thioalkyl purine, and isoxazolyl. The heteroaromatic and heterocyclic moieties can be optionally substituted as described above for aryl, including substituted with one or more substituents selected from hydroxyl, amino, alkylamino, arylamino, alkoxy, aryloxy, alkyl, heterocycle, halo, carboxy, acyl, acyloxy, amido, nitro, cyano, sulfonic acid, sulfate, phosphonic acid, phosphate, or phosphonate, either unprotected, or protected as necessary, as known to those skilled in the art, for example, as taught in Greene, et al., *Protective Groups in Organic Synthesis*, John Wiley and Sons, Second Edition, 1991.

The term "cyclic group" is used herein to refer to either aryl groups, non-aryl groups (i.e., cycloalkyl, heterocycloalkyl, cycloalkenyl, and heterocycloalkenyl groups), or both. Cyclic groups have one or more ring systems that can be substituted or unsubstituted. A cyclic group can contain one or more aryl groups, one or more non-aryl groups, or one or more aryl groups and one or more non-aryl groups. Also, the cyclic group can optionally be substituted as described above for aryl and heterocyclic.

It is understood that the compounds of the present disclosure relate to all optical isomers and stereo-isomers at the various possible atoms of the molecule, unless specified otherwise. Compounds may be separated or prepared as their pure enantiomers or diasteriomers by crystallization, chromatography or synthesis.

The deuterated forms contain heavy hydrogen including deuterium. The carbon labeled forms may contain carbon 13.

"Pharmaceutically acceptable salts" refer to derivatives of the disclosed compounds wherein the parent compound is modified by making acid or base salts thereof. The compounds of this disclosure form acid and base addition salts with a wide variety of organic and inorganic acids and bases and includes the physiologically acceptable salts which are often used in pharmaceutical chemistry. Such salts are also part of this disclosure. Typical inorganic acids used to form such salts include hydrochloric, hydrobromic, hydroiodic, nitric, sulfuric, phosphoric, hypophosphoric and the like. Salts derived from organic acids, such as aliphatic mono and dicarboxylic acids, phenyl substituted alkanoic acids, hydroxyalkanoic and hydroxyalkandioic acids, aromatic acids, aliphatic and aromatic sulfonic acids, may also be used. Such pharmaceutically acceptable salts thus include acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, naphthalene-2-benzoate, bromide, isobutyrate, phenylbutyrate, β-hydroxybutyrate, butyne-1,4-dioate, hexyne-1,4-dioate, cabrate, caprylate, chloride, cinnamate, citrate, formate, fumarate, glycollate, heptanoate, hippurate, lactate, malate, maleate, hydroxymaleate, malonate, mandelate, mesylate, nicotinate, isonicotinate, nitrate, oxalate, phthalate, teraphthalate, phosphate, monohydrogenphosphate, dihydrogenphosphate, metaphosphate, pyrophosphate, propiolate, propionate, phenylpropionate, salicylate, sebacate, succinate, suberate, sulfate, bisulfate, pyrosulfate, sulfite, bisulfite, sulfonate, benzene-sulfonate, p-bromobenzenesulfonate, chlorobenzenesulfonate, ethanesulfonate, 2-hydroxyethanesulfonate, methanesulfonate, naphthalene-1-sulfonate, naphthalene-2-sulfonate, p-toleunesulfonate, xylenesulfonate, tartarate, and the like.

Bases commonly used for formation of salts include ammonium hydroxide and alkali and alkaline earth metal hydroxides, carbonates, as well as aliphatic and primary, secondary and tertiary amines, aliphatic diamines. Bases especially useful in the preparation of addition salts include sodium hydroxide, potassium hydroxide, ammonium hydroxide, potassium carbonate, methylamine, diethylamine, and ethylene diamine.

"Solvates" refers to the compound formed by the interaction of a solvent and a solute and includes hydrates. Solvates are usually crystalline solid adducts containing solvent molecules within the crystal structure, in either stoichiometric or non-stoichiometric proportions.

The terms "effective amount" or "therapeutically effective amount" refer to an amount of the compound of the invention sufficient to provide a benefit in the treatment or prevention of viral disease, to delay or minimize symptoms associated with viral infection or viral-induced disease, or to cure or ameliorate the disease or infection or cause thereof. In particular, a therapeutically effective amount means an amount sufficient to provide a therapeutic benefit in vivo. Used in connection with an amount of a compound of the disclosure, the term preferably encompasses a non-toxic amount that improves overall therapy, reduces or avoids symptoms or causes of disease, or enhances the therapeutic efficacy of or synergies with another therapeutic agent.

The term "treating" refers to relieving the disease, disorder, or condition, i.e., causing regression of the disease, disorder, and/or condition. The term "preventing" refers to preventing a disease, disorder, or condition from occurring in a human or an animal that may be predisposed to the disease, disorder and/or condition, but has not yet been diagnosed as having it; and/or inhibiting the disease, disorder, or condition, i.e., arresting its development.

The compounds of the present invention may be prepared by those skilled in the art of chemical synthesis. For example, methods of preparing compounds of the present invention include, but are not limited to, the synthetic chemistry procedures shown in Schemes 1 and 2:

Scheme 2. Synthesis of substituted 5-(1,2,4-Oxadiazol-5-yl)-3,4-dihydropyrimidin-2(1H)-thiones.[13]

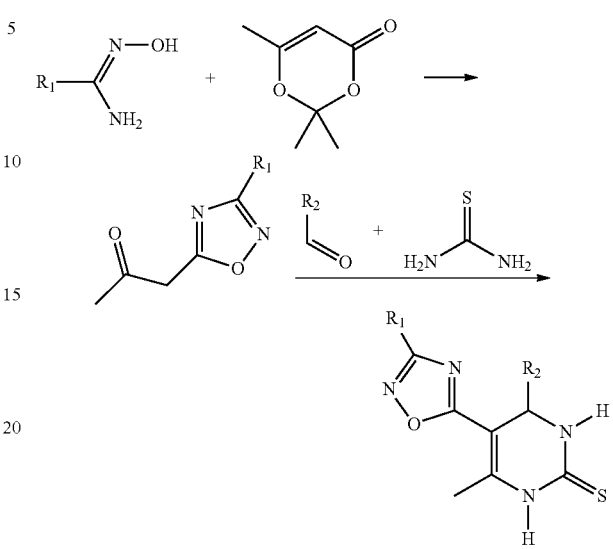

The following non-limiting examples are presented to further illustrate the present invention.

EXAMPLES

All reactions were carried out using oven-dried glassware and conducted under a positive pressure of nitrogen unless otherwise specified. NMR spectra were recorded on a JEOL Scheme 1. Synthesis of cyclohexyl-substituted 5-(thiazol-2-yl)-3,4-dihydropyrimidin-2(1H)-ones.[12]

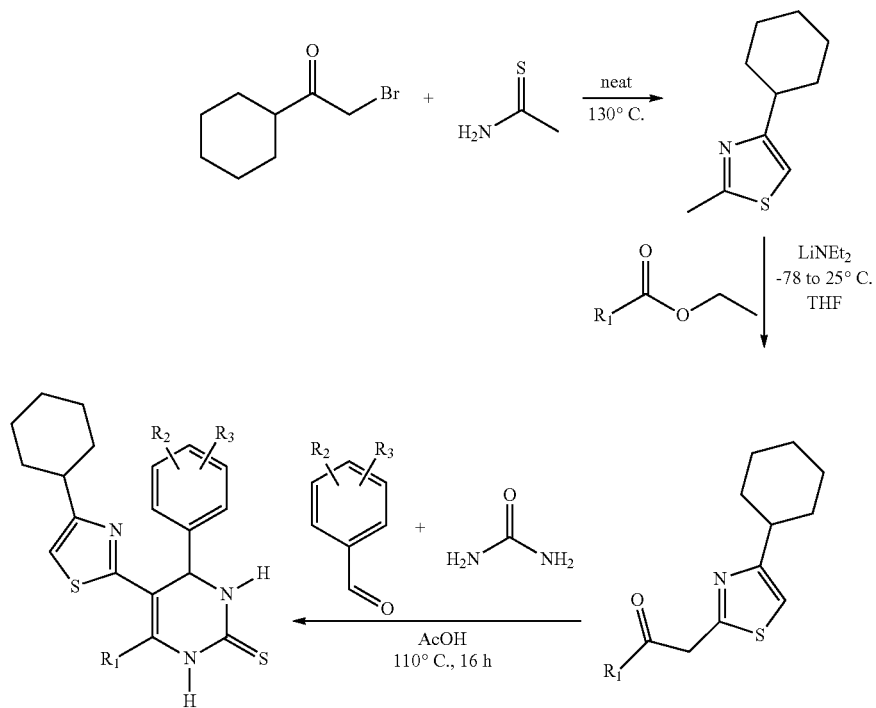

JNM-CS400 (400 MHz) spectrometer. High resolution mass spectra were obtained on an Agilent mass spectrometer using ESI-TOF at the Scripps Research Institute Mass Spectrometry Laboratory. LC/MS analyses were carried out on a Shimadzu LC/MS 2010 Series LC System with a Kromasil 100 5 micron C18 column (50×2.1 mmID). Silica gel purifications were accomplished using a CombiFlash $R_f$ system from Teledyne Isco using RediSep $R_f$ pre-packed columns. Preparative HPLC purifications were achieved using a Shimadzu SCL-10A system using either a Luna 5 micron C18 column (100×30 mmID) or a YMC 10 micron C18 column (150×20 mmID). All reagents as solvents were used as received from standard suppliers. Microfluidic experiments were conducted using a Syrris AFRICA® synthesis station.

A) the Following is an Overview for the Synthesis of 5-(Thiazol-2-Yl)-3,4-Dihydropyrimidin-2(1H)-ones

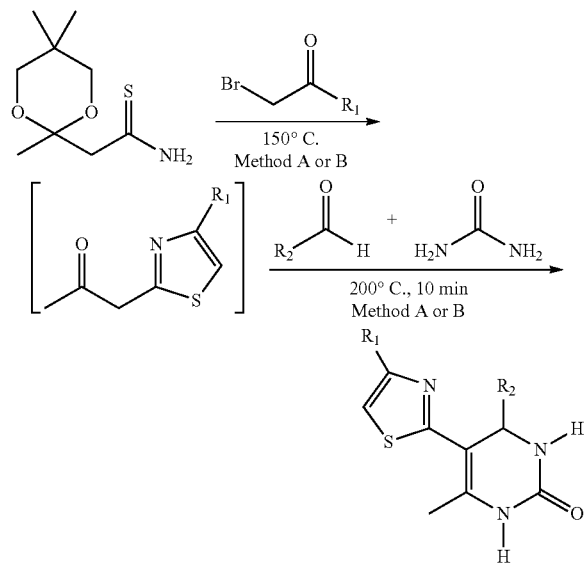

Scheme 3. Synthesis of 5-(thiazol-2-yl)-3,4-dihydropyrimidin-2(1H)-ones either by Method A (one-pot batch mode) or Method B (automated continuous flow)[14].

B) the Following is an Overview for the Synthesis of Ketal-Protected Thioamide

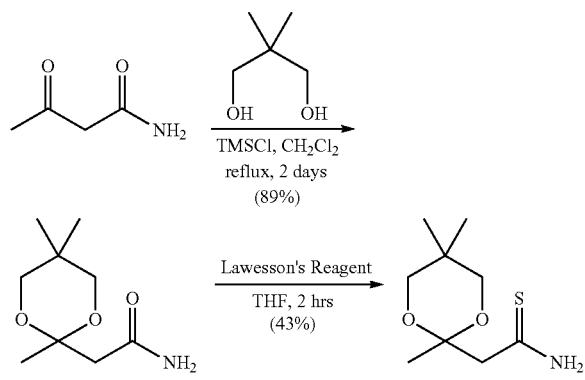

Scheme 4. Synthesis of ketal-protected thioamide building block.

C) Experimental Procedures for the Synthesis of Ketal-Protected Thioamide Including Characterization Data Example 1

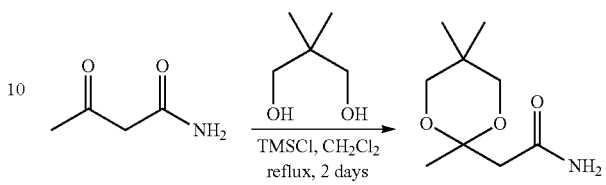

To a vacuum dried solid mixture of acetoacetamide (5.05 g, 50.0 mmol, 1 equiv) and neopentyl glycol (11.0 g, 110 mmol, 2.2 equiv) was added anhydrous $CH_2Cl_2$ (200 mL) followed by chlorotrimethylsilane (28.0 mL, 220 mmol, 4.4 equiv). The resulting clear solution was heated to reflux for 2 days. The resulting cloudy reaction mixture was cooled to 0° C., carefully quenched with portion-wise addition of saturated aqueous $NaHCO_3$, and the resulting biphasic mixture separated. Then, the organic layer was washed with brine, dried using $Na_2SO_4$, and concentrated to dryness in vacuo. The resulting clear oil was loaded onto a pre-packed silica gel column (120 g) using $CH_2Cl_2$ and chromatographed using $CH_2Cl_2$:MeOH (85 mL/min, 100% $CH_2Cl_2$ for 5 min, then ramping to 20% MeOH over 20 min). Following concentration of product eluents, the ketal-protected amide (8.35 g, 89%) was isolated as a clear oil which slowly became white crystals over time. $^1H$ NMR consistent with literature reported spectrum.[15]

Example 2

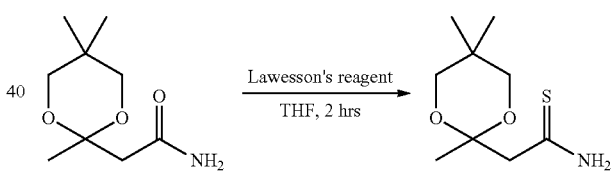

A solution of ketal-protected amide (5.81 g, 31.1 mmol, 1 equiv) in anhydrous THF was prepared and cooled to 0° C. Lawesson's reagent (6.91 g, 17.1 mmol, 0.55 equiv) was then added and the resulting yellow suspension was allowed to naturally warm to room temperature, stirring for a total of 2 hrs. The resulting yellow solution was concentrated in vacuo and re-dissolved in EtOAc. Then, the organic phase was washed with saturated aqueous $NaHCO_3$ followed by brine, dried using $Na_2SO_4$, and concentrated to dryness in vacuo. The crude material was adsorbed onto silica gel, loaded onto a pre-packed silica gel column (120 g), and chromatographed using hexanes:EtOAc (85 mL/min, 0% EtOAc to 30% EtOAc over 60 min). Following concentration of product eluents, the resulting white solid still required further purification. Thus, the chromatographed material was treated with toluene (50 mL), cooled to −20° C., and the resulting white precipitate collected to provide the ketal-protected thioamide (2.70 g, 43%) as white crystals. Mp 111-113° C. $^1H$ NMR (400 MHz, $CDCl_3$): δ (ppm) 8.25 (s, 1H), 7.85 (s, 1H), 3.63 (d, J=11.0 Hz, 2H), 3.44 (d, J=11.0 Hz, 2H), 3.16 (s, 2H), 1.46 (s, 3H), 1.06 (s, 3H), 0.84 (s, 3H). $^{13}C$ NMR (100 MHz, $CDCl_3$): δ (ppm) 205.0, 98.2, 54.0, 30.1, 23.1, 22.4, 18.8. HRMS (ESI): m/z calcd for $C_9H_{18}NO_2S$ $(M+H)^+$ 204.1053. found $(M+H)^+$ 204.1050.

D) General Experimental Procedure for the One-Pot Batch Mode Synthesis (Method A) of 5-(thiazol-2-yl)-3,4-dihydropyrimidin-2(1H)-ones and characterization data See FIG. 1, which is an illustration of Scheme 5, a One-pot synthesis of 5-(thiazol-2-yl)-3,4-dihydropyrimidin-2(1H)-ones.

General Procedure:

Reaction mixtures of ketal-protected thioamide (50 mg, 0.246 mmol, 1 equiv) and α-bromoketone (0.246 mmol) were prepared in 600 μL of DMF and heated to 150° C. for 5 min in sealed vials. After cooling, aldehyde (0.295 mmol, 1.2 equiv) and urea (0.295 mmol, 1.2 equiv) were added and the reaction mixtures heated to 200° C. for an additional 10 min. Once cooled, the crude reaction mixtures were adsorbed onto silica gel, loaded onto a pre-packed silica gel column (12 g), and chromatographed using hexanes:EtOAc (30 mL/min, 10% EtOAc to 100% EtOAc over 20 min). Then, an additional purification step using reverse-phase preparative HPLC was carried out on all compounds before screening for anti-HIV activity.

Example 3

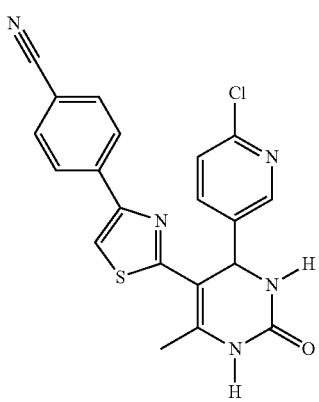 [SMILES: CC1=C(c2nc(-c3ccc(C#N)cc3)cs2)C(c2ccc(Cl)nc2)NC(=O)N1]

Title compound was isolated as a white solid (43 mg, 43%). $^1$H NMR (400 MHz, DMSO-$d_6$): δ (ppm) 9.27 (d, J=1.8 Hz, 1H), 8.41 (d, J=2.3 Hz, 1H), 8.23 (s, 1H), 8.08 (m, 2H), 7.88 (m, 3H), 7.78 (dd, J=8.2, 2.8 Hz, 1H), 7.47 (d, J=8.2 Hz, 1H), 5.71 (d, J=3.2 Hz, 1H), 2.34 (s, 3H).

Example 4

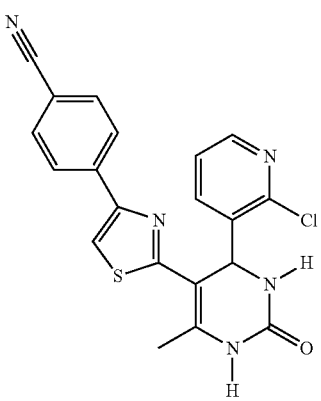 [SMILES: CC1=C(c2nc(-c3ccc(C#N)cc3)cs2)C(c2cccnc2Cl)NC(=O)N1]

Title compound was isolated as a yellow solid (35 mg, 35%). $^1$H NMR (400 MHz, DMSO-$d_6$): δ (ppm) 9.27 (d, J=1.4 Hz, 1H), 8.27 (dd, J=4.6, 1.8 Hz, 1H), 8.19 (s, 1H), 8.05 (m, 2H), 7.89 (m, 1H), 7.85 (m, 2H), 7.78 (dd, J=7.6, 2.1 Hz, 1H), 7.36 (dd, J=7.8, 4.6 Hz, 1H), 5.99 (d, J=3.2 Hz, 1H), 2.38 (s, 3H).

Example 5

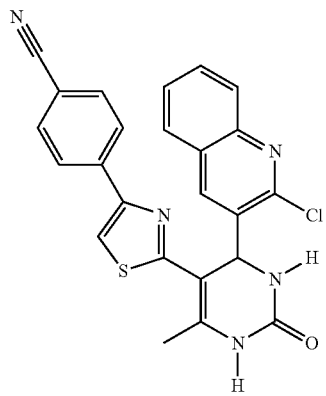 [SMILES: CC1=C(c2nc(-c3ccc(C#N)cc3)cs2)C(c2cc3ccccc3nc2Cl)NC(=O)N1]

Title compound was isolated as a yellow solid (26 mg, 23%). $^1$H NMR (400 MHz, DMSO-$d_6$): δ (ppm) 9.32 (d, J=1.8 Hz, 1H), 8.34 (s, 1H), 8.16 (s, 1H), 8.05-8.01 (m, 3H), 7.93-7.89 (m, 2H), 7.83 (m, 2H), 7.75 (ddd, J=8.5, 7.0, 1.5 Hz, 1H), 7.59 (ddd, J=8.3, 6.9, 1.4 Hz, 1H), 6.17 (d, J=2.3 Hz, 1H), 2.45 (s, 3H).

Example 6

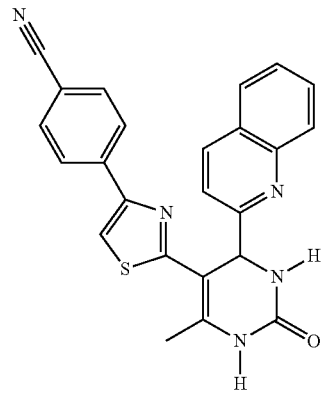 [SMILES: CC1=C(c2nc(-c3ccc(C#N)cc3)cs2)C(c2ccc3ccccc3n2)NC(=O)N1]

Title compound was isolated as an orange solid (19 mg, 18%). $^1$H NMR (400 MHz, DMSO-$d_6$): δ (ppm) 9.19 (d, J=1.8 Hz, 1H), 8.32 (d, J=8.2 Hz, 1H), 8.17 (s, 1H), 8.10-8.07 (m, 2H), 7.98 (d, J=7.3 Hz, 1H), 7.91-7.85 (m, 4H), 7.74 (ddd, J=8.5, 7.0, 1.5 Hz, 1H), 7.58-7.54 (m, 2H), 5.78 (d, J=2.8 Hz, 1H), 2.38 (s, 3H).

Example 7

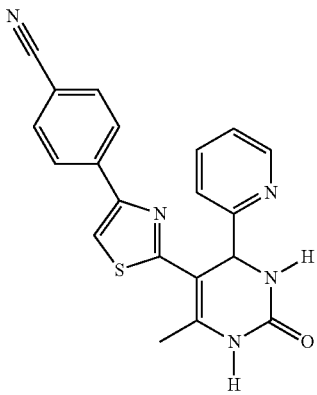 [SMILES: CC1=C(c2nc(-c3ccc(C#N)cc3)cs2)C(c2ccccn2)NC(=O)N1]

Title compound was isolated as a yellow solid (24 mg, 26%). $^1$H NMR (400 MHz, DMSO-d$_6$): δ (ppm) 9.03 (d, J=1.8 Hz, 1H), 8.46 (m, 1H), 8.14 (s, 1H), 8.06-8.04 (m, 2H), 7.85-7.83 (m, 2H), 7.70-7.65 (m, 2H), 7.35 (d, J=7.8 Hz, 1H), 7.19 (m, 1H), 5.56 (d, J=3.2 Hz, 1H), 2.29 (s, 3H).

Example 8

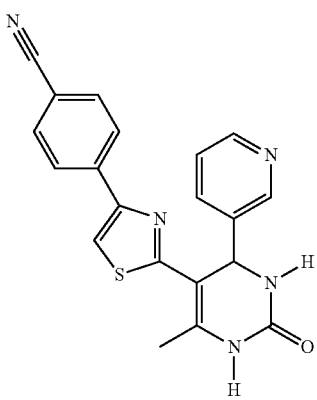 [SMILES: CC1=C(c2nc(-c3ccc(C#N)cc3)cs2)C(c2cccnc2)NC(=O)N1]

Title compound was isolated as a white solid (40 mg, 43%). $^1$H NMR (400 MHz, DMSO-d$_6$): δ (ppm) 9.22 (d, J=1.8 Hz, 1H), 8.59 (d, J=2.3 Hz, 1H), 8.42 (dd, J=4.6, 1.4 Hz, 1H), 8.22 (s, 1H), 8.09-8.07 (m, 2H), 7.90-7.85 (m, 3H), 7.72 (m, 1H), 7.34 (dd, J=7.8, 4.6 Hz, 1H), 5.67 (d, J=3.2 Hz, 1H), 2.36 (s, 3H).

Example 9

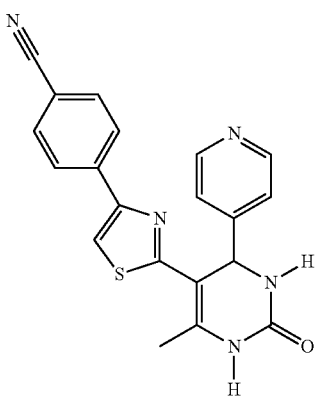 [SMILES: CC1=C(c2nc(-c3ccc(C#N)cc3)cs2)C(c2ccncc2)NC(=O)N1]

Title compound was isolated as a yellow solid (31 mg, 34%). $^1$H NMR (400 MHz, DMSO-d$_6$): δ (ppm) 9.22 (d, J=1.8 Hz, 1H), 8.49 (d, J=5.5 Hz, 1H), 8.23 (s, 1H), 8.09-8.06 (m, 2H), 7.92-7.86 (m, 3H), 7.33 (dd, J=4.6, 1.4 Hz, 2H), 5.64 (d, J=3.7 Hz, 1H), 2.33 (s, 3H).

Example 10

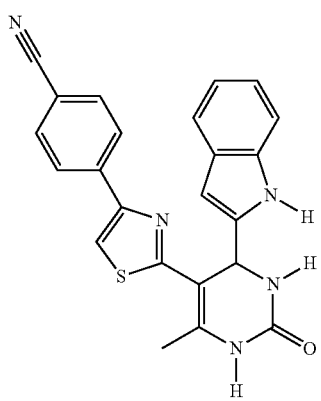 [SMILES: CC1=C(c2nc(-c3ccc(C#N)cc3)cs2)C(c2cc3ccccc3[nH]2)NC(=O)N1]

Title compound was isolated as a brown solid (directly purified, % yield n.d.). $^1$H NMR (400 MHz, DMSO-d$_6$): δ (ppm) 10.78 (s, 1H), 9.16 (d, J=1.8 Hz, 1H), 8.18 (s, 1H), 8.11-8.08 (m, 2H), 7.87-7.85 (m, 2H), 7.68 (m, 1H), 7.40 (d, J=7.8 Hz, 1H), 7.33 (d, J=7.8 Hz, 1H), 7.00 (ddd, J=8.0, 7.0, 1.0 Hz, 1H), 6.90 (m, 1H), 6.23 (d, J=2.3 Hz, 1H), 5.74 (d, J=3.2 Hz, 1H), 2.39 (s, 3H).

Example 11

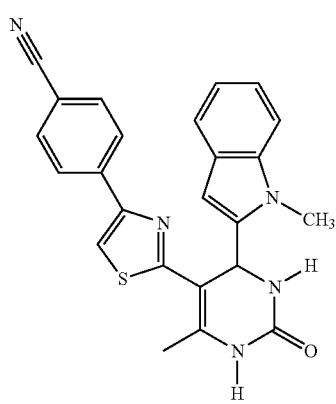 [SMILES: CC1=C(c2nc(-c3ccc(C#N)cc3)cs2)C(c2cc3ccccc3n2C)NC(=O)N1]

Title compound was isolated as a yellow solid (31 mg, 30%). $^1$H NMR (400 MHz, DMSO-d$_6$): δ (ppm) 9.21 (d, J=1.4 Hz, 1H), 8.15 (s, 1H), 8.05-8.03 (m, 2H), 7.92 (m, 1H), 7.86-7.84 (m, 2H), 7.44 (d, J=8.2 Hz, 1H), 7.40 (d, J=7.8 Hz, 1H), 7.08 (ddd, J=8.2, 7.1, 1.1 Hz, 1H), 6.94 (ddd, J=7.8, 6.9, 0.9 Hz, 1H), 6.27 (s, 1H), 5.89 (d, J=3.7 Hz, 1H), 3.91 (s, 3H), 2.39 (s, 3H).

Example 12

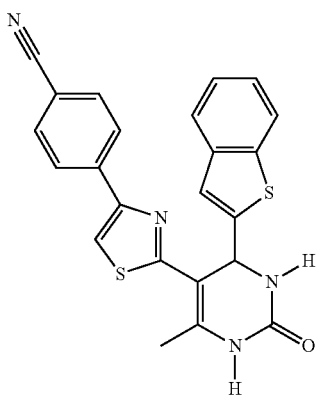 [SMILES: CC1=C(c2nc(-c3ccc(C#N)cc3)cs2)C(c2cc3ccccc3s2)NC(=O)N1]

Title compound was isolated as a yellow solid (37 mg, 35%). $^1$H NMR (400 MHz, DMSO-$d_6$): δ (ppm) 9.30 (d, J=1.8 Hz, 1H), 8.27 (s, 1H), 8.17-8.15 (m, 2H), 8.04 (m, 1H), 7.91-7.89 (m, 2H), 7.81 (d, J=7.8 Hz, 1H), 7.76 (d, J=7.8 Hz, 1H), 7.31-7.23 (m, 3H), 6.00 (d, J=3.7 Hz, 1H), 2.31 (s, 3H).

Example 13

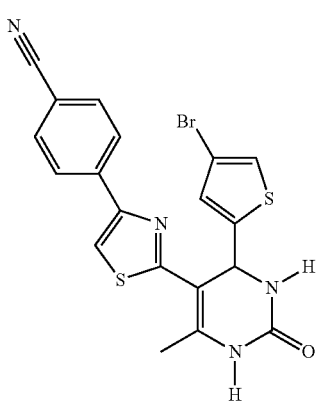 [SMILES: CC1=C(c2nc(-c3ccc(C#N)cc3)cs2)C(c2cc(Br)cs2)NC(=O)N1]

Title compound was isolated as a yellow solid (39 mg, 35%). $^1$H NMR (400 MHz, DMSO-$d_6$): δ (ppm) 9.26 (d, J=1.4 Hz, 1H), 8.23 (s, 1H), 8.11-8.08 (m, 2H), 7.97 (m, 1H), 7.88-7.85 (m, 2H), 7.66 (d, J=3.2 Hz, 1H), 7.54 (d, J=3.2 Hz, 1H), 5.94 (d, J=3.7 Hz, 1H), 2.26 (s, 3H).

Example 14

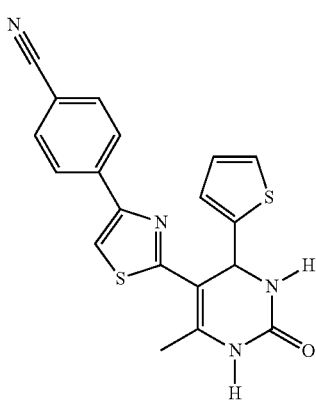 [SMILES: CC1=C(c2nc(-c3ccc(C#N)cc3)cs2)C(c2cccs2)NC(=O)N1]

Title compound was isolated as an orange solid (18 mg, 19%). $^1$H NMR (400 MHz, DMSO-$d_6$): δ (ppm) 9.31 (d, J=1.8 Hz, 1H), 8.29 (s, 1H), 8.16-8.14 (m, 2H), 7.99 (m, 1H), 7.92-7.90 (m, 2H), 7.47 (d, J=1.4 Hz, 1H), 6.94 (m, 1H), 6.52 (s, 1H), 5.91 (d, J=3.7 Hz, 1H), 2.30 (s, 3H).

Example 15

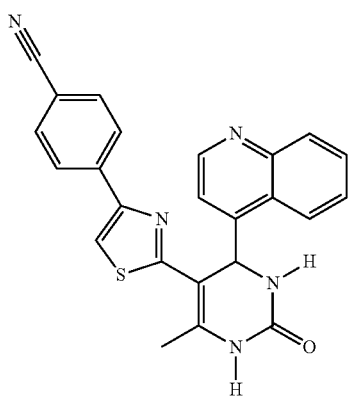 [SMILES: CC1=C(c2nc(-c3ccc(C#N)cc3)cs2)C(c2ccnc3ccccc23)NC(=O)N1]

Title compound was isolated as a brown solid (38 mg, 37%). $^1$H NMR (400 MHz, DMSO-$d_6$): δ (ppm) 9.29 (d, J=1.4 Hz, 1H), 8.81 (d, J=4.6 Hz, 1H), 8.59 (d, J=7.8 Hz, 1H), 8.10 (s, 1H), 8.02 (dd, J=8.2, 0.9 Hz, 1H), 7.95 (m, 1H), 7.81-7.69 (m, 6H), 7.44 (d, J=4.6 Hz, 1H), 6.51 (d, J=3.2 Hz, 1H), 2.44 (s, 3H).

Example 16

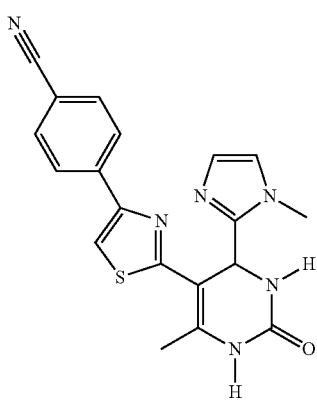 [SMILES: CC1=C(c2nc(-c3ccc(C#N)cc3)cs2)C(c2nccn2C)NC(=O)N1]

Title compound was isolated as a brown solid (directly purified, % yield n.d.). $^1$H NMR (400 MHz, DMSO-$d_6$): δ (ppm) 9.14 (s, 1H), 8.15 (s, 1H), 8.02 (d, J=8.2 Hz, 2H), 7.57 (d, J=8.2 Hz, 2H), 7.71 (s, 1H), 7.02 (s, 1H), 6.73 (s, 1H), 5.78 (s, 1H), 3.80 (s, 3H), 2.44 (s, 3H).

Example 17

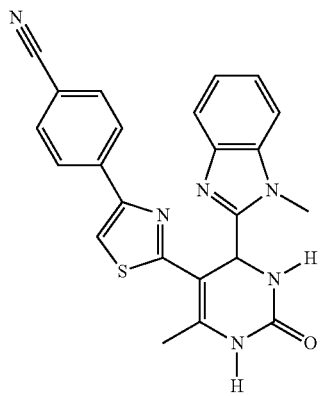 [SMILES: CC1=C(c2nc(-c3ccc(C#N)cc3)cs2)C(c2nc3ccccc3n2C)NC(=O)N1]

Title compound was isolated as a brown solid (directly purified, % yield n.d.). $^1$H NMR (400 MHz, DMSO-d$_6$): δ (ppm) 9.25 (s, 1H), 8.15 (s, 1H), 7.98-7.84 (m, 5H), 7.54 (m, 2H), 7.21-7.10 (m, 2H), 6.08 (s, 1H), 4.00 (s, 3H), 2.36 (s, 3H).

Example 18

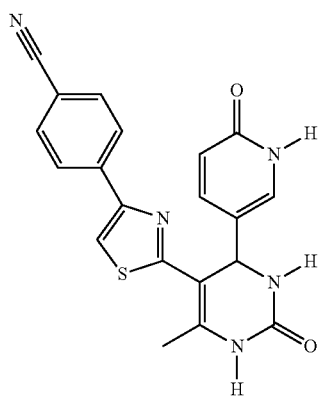 [SMILES: CC1=C(c2nc(-c3ccc(C#N)cc3)cs2)C(c2ccc(=O)[nH]c2)NC(=O)N1]

Title compound was isolated as a yellow solid (directly purified, % yield n.d.). $^1$H NMR (400 MHz, DMSO-d$_6$): δ (ppm) 11.42 (s, 1H), 9.14 (s, 1H), 8.22 (s, 1H), 8.11 (d, J=8.2 Hz, 2H), 7.88 (d, J=8.2 Hz, 2H), 7.67 (s, 1H), 7.41 (dd, J=9.6, 2.8 Hz, 1H), 7.22 (s, 1H), 6.31 (d, J=9.6 Hz, 1H), 5.33 (d, J=2.8 Hz, 1H), 2.34 (s, 3H).

Example 19

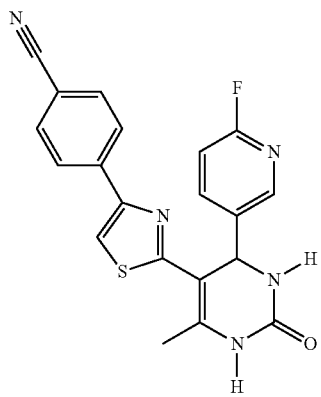 [SMILES: CC1=C(c2nc(-c3ccc(C#N)cc3)cs2)C(c2ccc(F)nc2)NC(=O)N1]

Title compound was isolated as a yellow solid (62 mg, 65%). $^1$H NMR (400 MHz, DMSO-d$_6$): δ (ppm) 9.24 (d, J=1.8 Hz, 1H), 8.22 (m, 2H), 8.09-8.06 (m, 2H), 7.93-7.85 (m, 4H), 7.13 (dd, J=8.5, 2.5 Hz, 1H), 5.70 (d, J=3.2 Hz, 1H), 2.34 (s, 3H).

Example 20

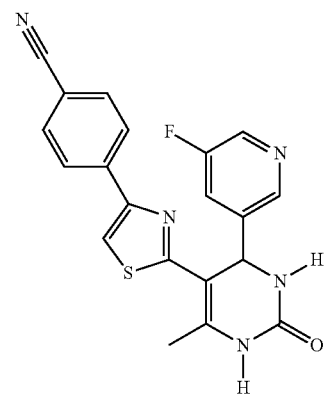 [SMILES: CC1=C(c2nc(-c3ccc(C#N)cc3)cs2)C(c2cncc(F)c2)NC(=O)N1]

Title compound was isolated as a yellow solid (51 mg, 53%). $^1$H NMR (400 MHz, DMSO-d$_6$): δ (ppm) 9.27 (s, 1H), 8.46 (m, 2H), 8.24 (s, 1H), 8.08 (d, J=8.2 Hz, 2H), 7.92 (s, 1H), 7.88 (d, J=8.2 Hz, 2H), 7.60 (d, J=9.6 Hz, 1H), 5.76 (d, J=2.8 Hz, 1H), 2.36 (s, 3H

Example 21

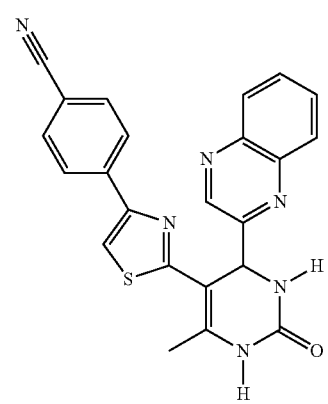

Title compound was isolated as an orange solid (directly purified, % yield n.d.). $^1$H NMR (400 MHz, DMSO-d$_6$): δ (ppm) 9.30 (s, 1H), 9.07 (s, 1H), 8.20 (s, 1H), 8.08 (d, J=8.2 Hz, 2H), 8.03 (d, J=7.8 Hz, 2H), 7.88-7.80 (m, 5H), 6.02 (d, J=2.3 Hz, 1H), 2.34 (s, 3H).

Example 22

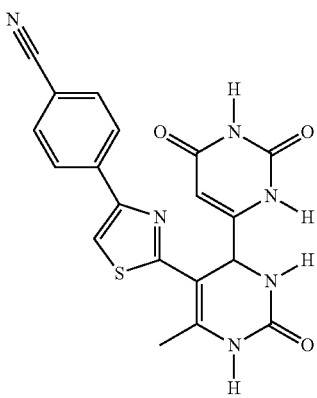 [SMILES: CC1=C(c2nc(-c3ccc(C#N)cc3)cs2)C(c2cc(=O)[nH]c(=O)[nH]2)NC(=O)N1]

Title compound was isolated as a tan solid (directly purified, % yield n.d.). ¹H NMR (400 MHz, DMSO-d$_6$): δ (ppm) 11.02 (s, 1H), 8.66 (s, 1H), 8.22 (d, J=8.7 Hz, 2H), 7.96 (d, J=8.2 Hz, 2H), 7.57 (s, 1H), 7.30 (s, 1H), 5.78 (d, J=1.4 Hz, 1H), 2.06 (s, 3H). Two N—H's not observed.

Example 23

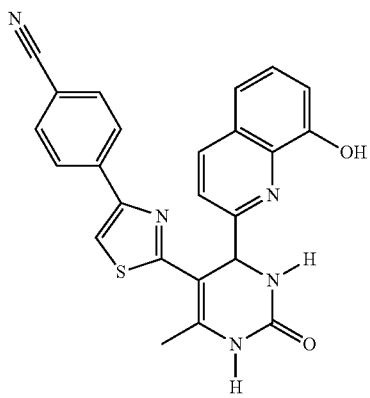 [SMILES: CC1=C(c2nc(-c3ccc(C#N)cc3)cs2)C(c2ccc3cccc(O)c3n2)NC(=O)N1]

Title compound was isolated as a tan solid (directly purified, % yield n.d.). ¹H NMR (400 MHz, DMSO-d$_6$): δ (ppm) 9.31 (s, 1H), 9.23 (s, 1H), 8.24 (s, 1H), 8.22 (d, J=2.3 Hz, 1H), 8.07 (d, J=8.7 Hz, 2H), 8.01 (s, 1H), 7.82 (d, J=8.7 Hz, 2H), 7.43 (m, 1H), 7.38 (d, J=7.8 Hz, 1H), 7.32 (m, 1H), 7.10 (dd, J=7.3, 1.4 Hz, 1H), 5.83 (d, J=2.3 Hz, 1H), 2.38 (s, 3H).

Example 24

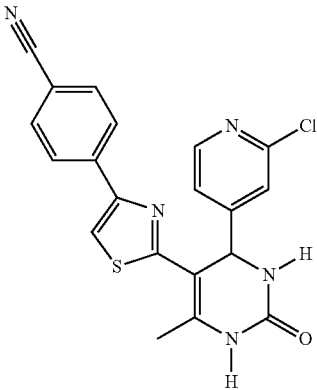 [SMILES: CC1=C(c2nc(-c3ccc(C#N)cc3)cs2)C(c2ccnc(Cl)c2)NC(=O)N1]

Title compound was isolated as a yellow solid (42 mg, 42%). ¹H NMR (400 MHz, DMSO-d$_6$): δ (ppm) 9.30 (d, J=1.8 Hz, 1H), 8.35 (d, J=5.0 Hz, 1H), 8.26 (s, 1H), 8.10-8.07 (m, 2H), 7.97 (m, 1H), 7.90-7.87 (m, 2H), 7.45 (d, J=1.4 Hz, 1H), 7.36 (dd, J=5.0, 1.4 Hz, 1H), 5.70 (d, J=3.7 Hz, 1H), 2.34 (s, 3H).

Example 25

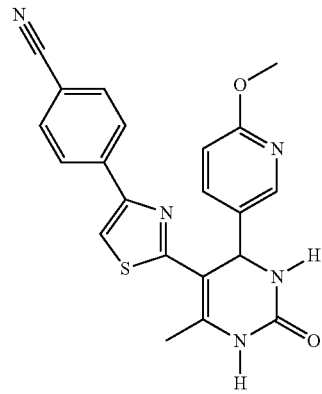 [SMILES: COc1ccc(C2NC(=O)NC(C)=C2c2nc(-c3ccc(C#N)cc3)cs2)cn1]

Title compound was isolated as a white solid (48 mg, 48%). ¹H NMR (400 MHz, DMSO-d$_6$): δ (ppm) 9.17 (d, J=1.8 Hz, 1H), 8.21 (s, 1H), 8.12 (d, J=2.3 Hz, 1H), 8.11-8.08 (m, 2H), 7.90-7.87 (m, 2H), 7.77 (m, 1H), 7.64 (dd, J=8.5, 2.5 Hz, 1H), 6.77 (d, J=8.2 Hz, 1H), 5.58 (d, J=2.8 Hz, 1H), 3.77 (s, 3H), 2.36 (s, 3H).

Example 26

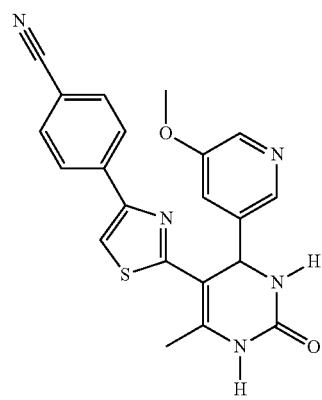 [SMILES: COc1cncc(C2NC(=O)NC(C)=C2c2nc(-c3ccc(C#N)cc3)cs2)c1]

Title compound was isolated as a yellow solid (47 mg, 47%). ¹H NMR (400 MHz, DMSO-d$_6$): δ (ppm) 9.21 (d, J=1.8 Hz, 1H), 8.21 (s, 1H), 8.17 (s, 1H), 8.15 (d, J=2.8 Hz, 1H), 8.11-8.08 (m, 2H), 7.89-7.85 (m, 3H), 7.28 (m, 1H), 5.67 (d, J=3.2 Hz, 1H), 3.76 (s, 3H), 2.35 (s, 3H).

Example 27

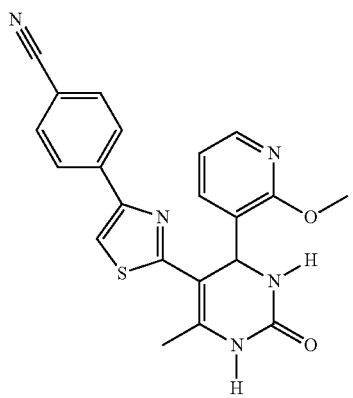 [SMILES: COc1ncccc1C1NC(=O)NC(C)=C1c1nc(-c2ccc(C#N)cc2)cs1]

Title compound was isolated as a yellow solid (24 mg, 24%). ¹H NMR (400 MHz, DMSO-$d_6$): δ (ppm) 9.12 (d, J=1.4 Hz, 1H), 8.15 (s, 1H), 8.05-8.02 (m, 3H), 7.88-7.86 (m, 2H), 7.55 (m, 1H), 7.51 (dd, J=7.3, 1.8 Hz, 1H), 6.89 (dd, J=7.3, 4.6 Hz, 1H), 5.79 (d, J=3.2 Hz, 1H), 3.94 (s, 3H), 2.39 (s, 3H).

Example 28

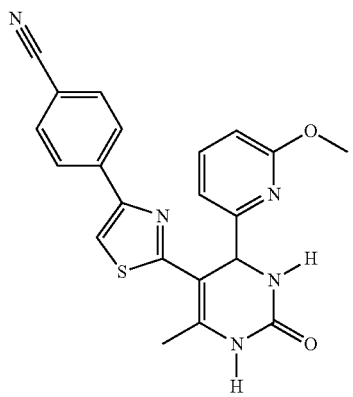 [SMILES: COc1cccc(C2NC(=O)NC(C)=C2c2nc(-c3ccc(C#N)cc3)cs2)n1]

Title compound was isolated as a tan solid (37 mg, 37%). ¹H NMR (400 MHz, DMSO-$d_6$): δ (ppm) 9.10 (d, J=1.4 Hz, 1H), 8.19 (s, 1H), 8.12-8.10 (m, 2H), 7.89-7.87 (m, 2H), 7.64 (s, 1H), 7.60 (dd, J=7.3, 7.3 Hz, 1H), 6.94 (d, J=6.9 Hz, 1H), 6.63 (d, J=7.8 Hz, 1H), 5.51 (d, J=3.2 Hz, 1H), 3.73 (s, 3H), 2.30 (s, 3H).

Example 29

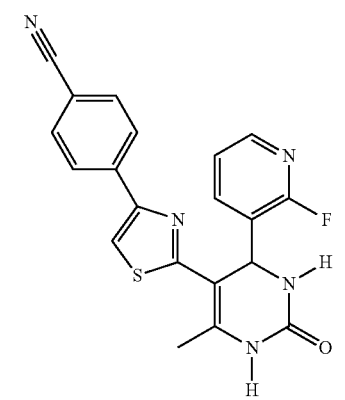 [SMILES: CC1=C(c2nc(-c3ccc(C#N)cc3)cs2)C(c2cccnc2F)NC(=O)N1]

Title compound was isolated as a brown solid (directly purified, % yield n.d.). ¹H NMR (400 MHz, DMSO-$d_6$): δ (ppm) 9.26 (d, J=1.4 Hz, 1H), 8.19 (s, 1H), 8.09 (s, 1H), 8.05 (d, J=8.2 Hz, 2H), 7.90-7.85 (m, 4H), 7.29 (m, 1H), 5.85 (d, J=3.2 Hz, 1H), 2.35 (s, 3H).

Example 30

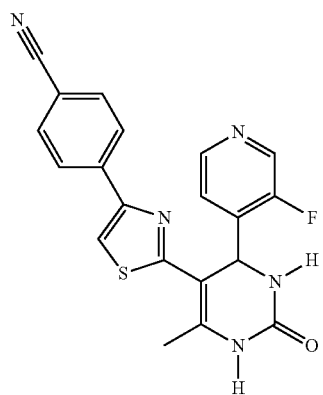 [SMILES: CC1=C(c2nc(-c3ccc(C#N)cc3)cs2)C(c2ccncc2F)NC(=O)N1]

Title compound was isolated as a tan solid (directly purified, % yield n.d.). ¹H NMR (400 MHz, DMSO-$d_6$): δ (ppm) 9.31 (s, 1H), 8.53 (s, 1H), 8.35 (d, J=5.0 Hz, 1H), 8.21 (s, 1H), 8.04 (d, J=8.2 Hz, 2H), 7.89-7.87 (m, 3H), 7.40 (m, 1H), 5.94 (d, J=2.8 Hz, 1H), 2.35 (s, 3H).

Example 31

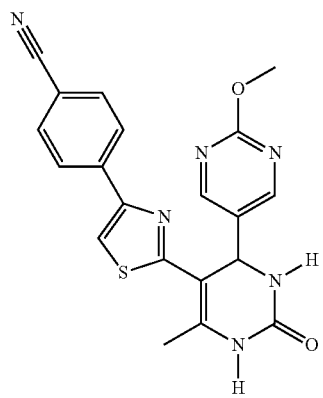 [SMILES: COc1ncc(C2NC(=O)NC(C)=C2c2nc(-c3ccc(C#N)cc3)cs2)cn1]

Title compound was isolated as a yellow solid (directly purified, % yield n.d.). ¹H NMR (400 MHz, DMSO-$d_6$): δ (ppm) 9.26 (d, J=1.4 Hz, 1H), 8.54 (s, 2H), 8.23 (s, 1H), 8.09-8.07 (m, 2H), 7.88-7.86 (m, 2H), 7.82 (m, 1H), 5.68 (d, J=2.8 Hz, 1H), 3.83 (s, 3H), 2.34 (s, 3H).

Example 32

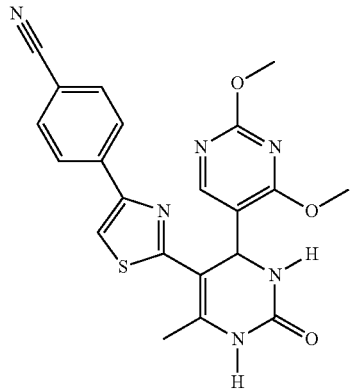 [SMILES: COc1ncc(C2NC(=O)NC(C)=C2c2nc(-c3ccc(C#N)cc3)cs2)c(OC)n1]

Title compound was isolated as a yellow solid (directly purified, % yield n.d.). $^1$H NMR (400 MHz, DMSO-$d_6$): δ (ppm) 9.16 (s, 1H), 8.18 (s, 1H), 8.12 (s, 1H), 8.05 (d, J=8.2 Hz, 2H), 7.88 (d, J=8.7 Hz, 2H), 7.54 (m, 1H), 5.72 (d, J=2.8 Hz, 1H), 3.96 (s, 3H), 3.81 (s, 3H), 2.34 (s, 3H).

Figure 2:
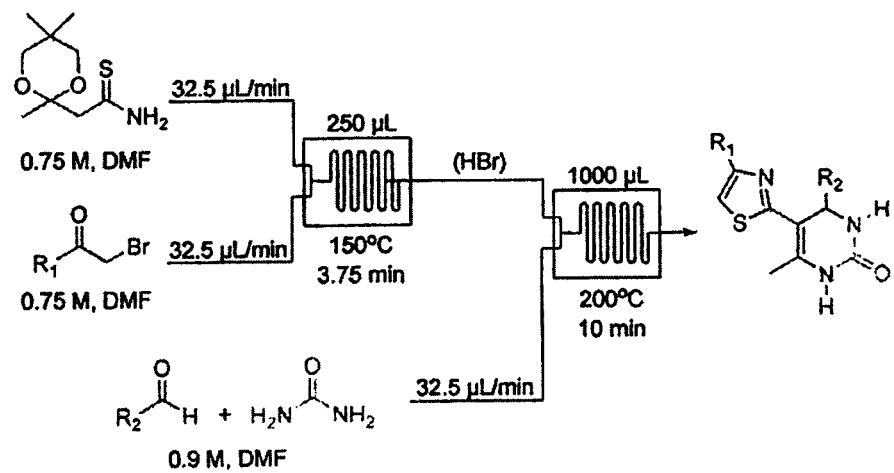
FIG. 2 illustrates Scheme 6, which is a continuous flow synthesis of 5-(thiazol-2-yl)-3,4-dihydropyrimidin-2(1H)-ones.

E) General Experimental Procedure for the Continuous Flow Synthesis (Method B) of 5-(thiazol-2-yl)-3,4-dihydropyrimidin-2(1H)-ones See FIG. 2, which is an illustration of Scheme 6, a Continuous flow synthesis of 5-(thiazol-2-yl)-3,4-dihydropyrimidin-2(1H)-ones.

All reactions were conducted in DMF under a positive pressure of nitrogen. Streams of the ketal-protected thioamide (32.5 µL/min, 0.75 M, DMF, 1 equiv) and a solution of α-bromoketones (32.5 µL/min, 0.75 M, DMF, 1 equiv) were mixed in a 250 µL, glass reactor heated to 150° C. (3.75 min). After exiting the chip, the combined flow (65.0 µL/min) was introduced to a single steam (32.5 µL/min, 0.9 M, DMF, 1.2 equiv) of aldehyde and urea in a 1000 µL, glass reactor heated to 200° C. (10 min). The reaction flow was then collected (1250 µL) after passing though the back pressure regulator. These reactions were carried out with a back pressure of 6.0 bar.

Figure 3:
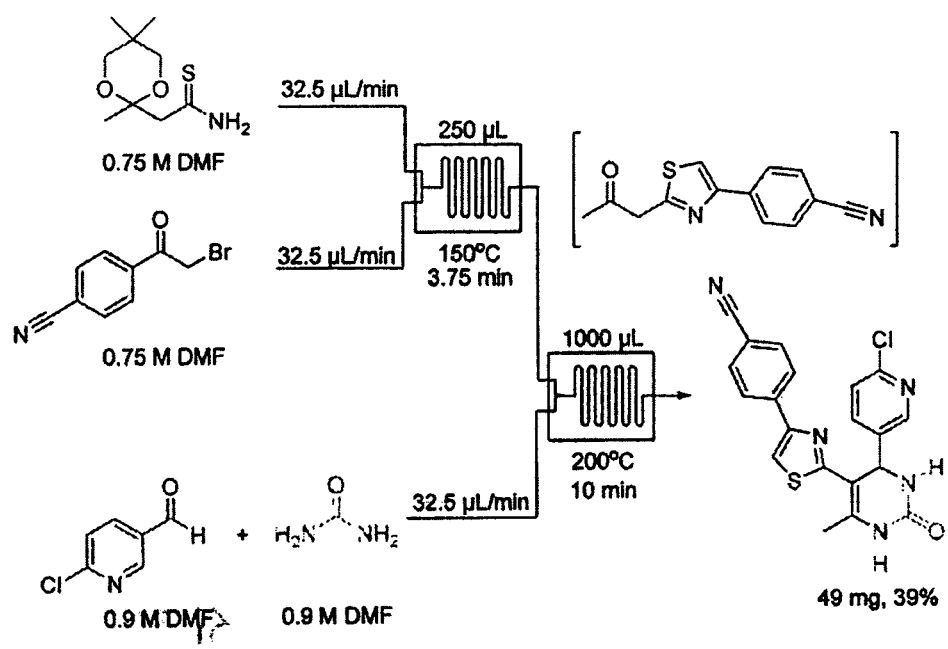
FIG. 3 illustrates Scheme 7, which is another example of a continuous flow synthesis.

See FIG. 3, which is an illustration of Scheme 7, another example of continuous flow synthesis.

F) Table of Additional 5-(thiazol-2-yl)-3,4-dihydropyrimidin-2(1H)-ones Prepared.

Example 33

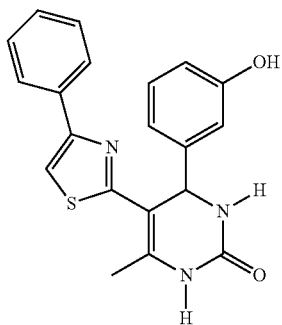 [SMILES: CC1=C(c2nc(-c3ccccc3)cs2)C(c2cccc(O)c2)NC(=O)N1]

Example 34

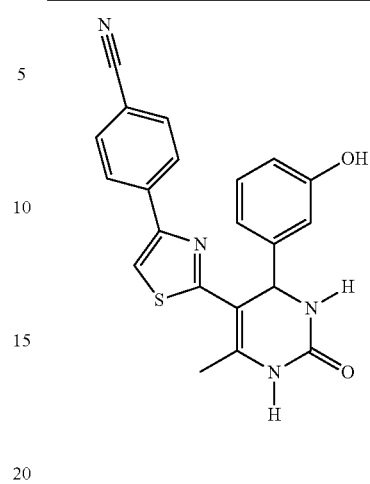

Example 35

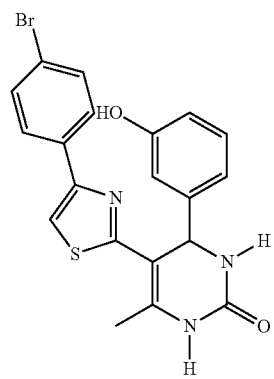 [SMILES: CC1=C(c2nc(-c3ccc(Br)cc3)cs2)C(c2cccc(O)c2)NC(=O)N1]

Example 36

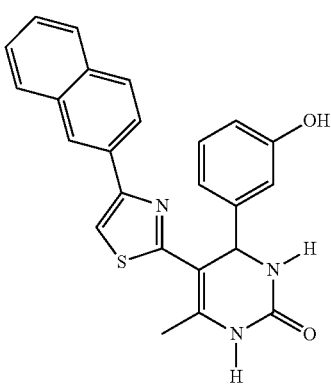 [SMILES: CC1=C(c2nc(-c3ccc4ccccc4c3)cs2)C(c2cccc(O)c2)NC(=O)N1]

Example 37

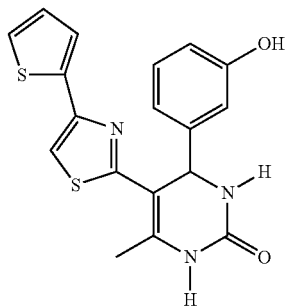 [SMILES: CC1=C(c2nc(-c3cccs3)cs2)C(c2cccc(O)c2)NC(=O)N1]

-continued
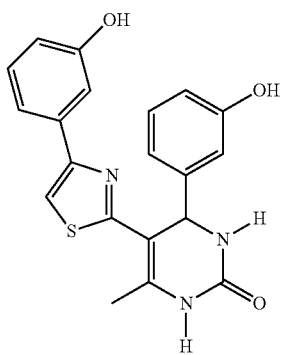 [SMILES: CC1=C(c2nc(-c3cccc(O)c3)cs2)C(c2cccc(O)c2)NC(=O)N1]
Example 38
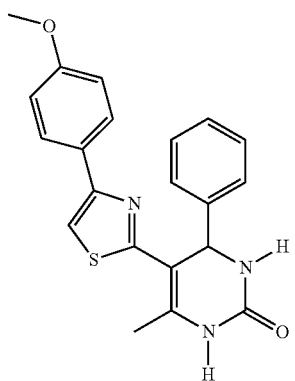 [SMILES: COc1ccc(-c2csc(C3=C(C)NC(=O)NC3c3ccccc3)n2)cc1]
Example 39
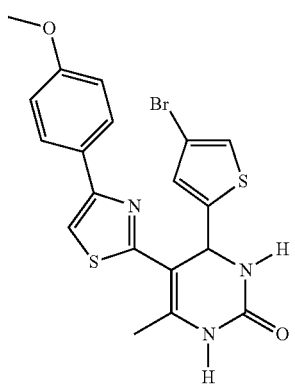 [SMILES: COc1ccc(-c2csc(C3=C(C)NC(=O)NC3c3cc(Br)cs3)n2)cc1]
Example 40
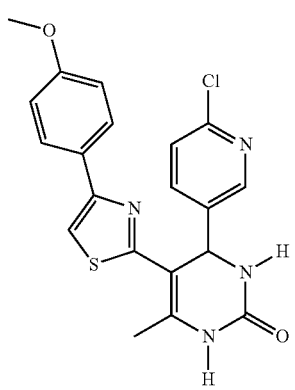 [SMILES: COc1ccc(-c2csc(C3=C(C)NC(=O)NC3c3ccc(Cl)nc3)n2)cc1]
Example 41
-continued
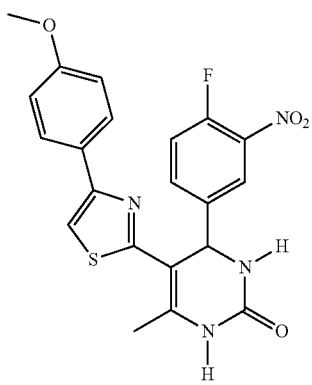 [SMILES: COc1ccc(-c2csc(C3=C(C)NC(=O)NC3c3ccc(F)c([N+](=O)[O-])c3)n2)cc1]
Example 42
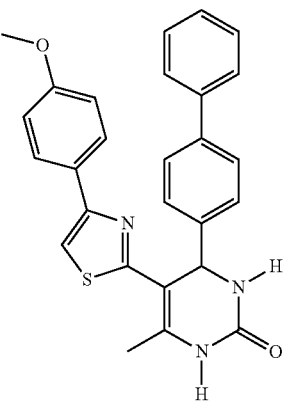 [SMILES: COc1ccc(-c2csc(C3=C(C)NC(=O)NC3c3ccc(-c4ccccc4)cc3)n2)cc1]
Example 43
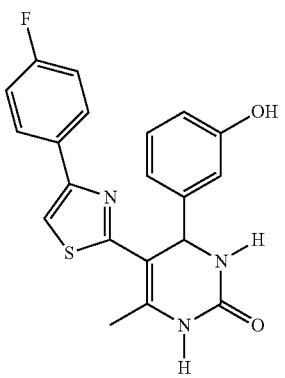 [SMILES: CC1=C(c2nc(-c3ccc(F)cc3)cs2)C(c2cccc(O)c2)NC(=O)N1]
Example 44
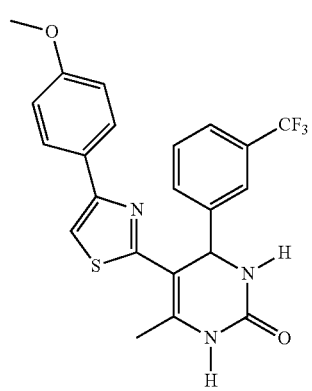 [SMILES: COc1ccc(-c2csc(C3=C(C)NC(=O)NC3c3cccc(C(F)(F)F)c3)n2)cc1]
Example 45

-continued
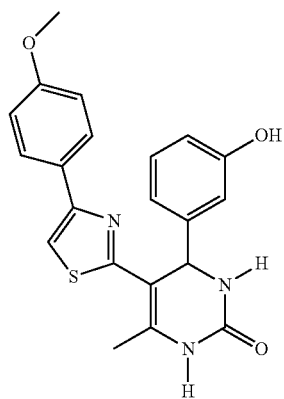 [SMILES: COc1ccc(-c2csc(C3=C(C)NC(=O)NC3c3cccc(O)c3)n2)cc1]
Example 46
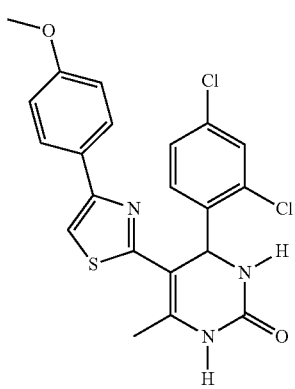 [SMILES: COc1ccc(-c2csc(C3=C(C)NC(=O)NC3c3ccc(Cl)cc3Cl)n2)cc1]
Example 47
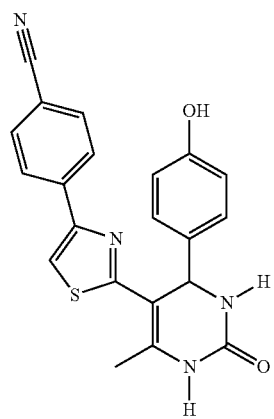 [SMILES: CC1=C(c2nc(-c3ccc(C#N)cc3)cs2)C(c2ccc(O)cc2)NC(=O)N1]
Example 48
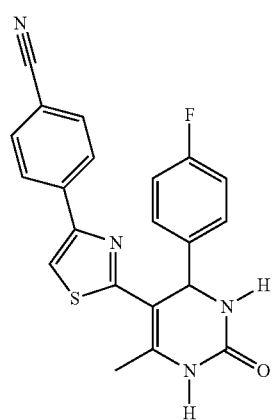 [SMILES: CC1=C(c2nc(-c3ccc(C#N)cc3)cs2)C(c2ccc(F)cc2)NC(=O)N1]
Example 49
-continued
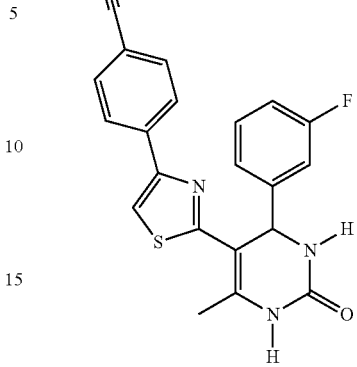
Example 50
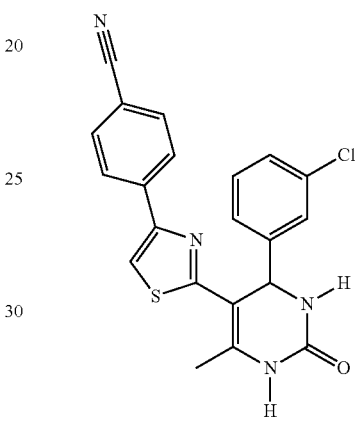
Example 51
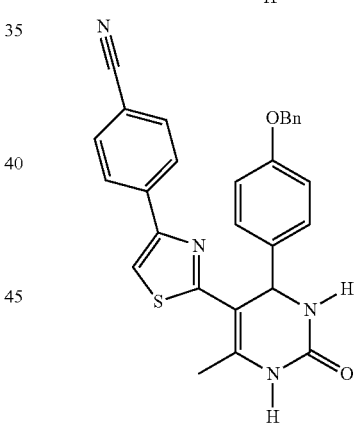
Example 52
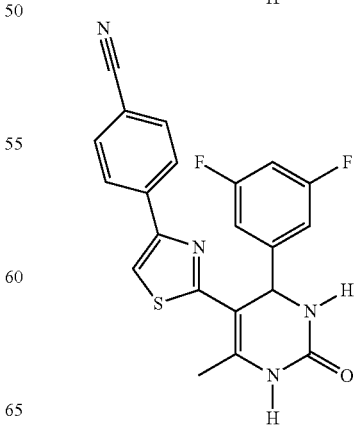
Example 53

| | |
|---|---|
| Example 54 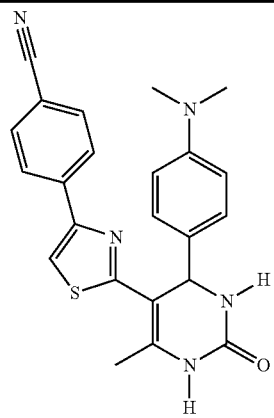 | Example 58 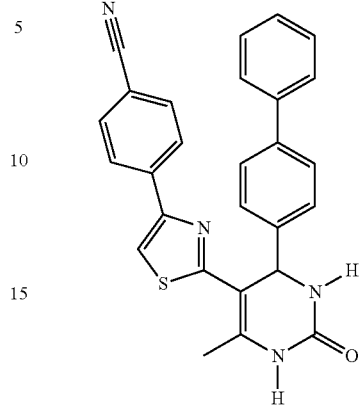 |
| Example 55 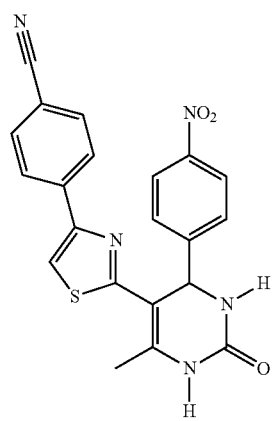 | Example 59 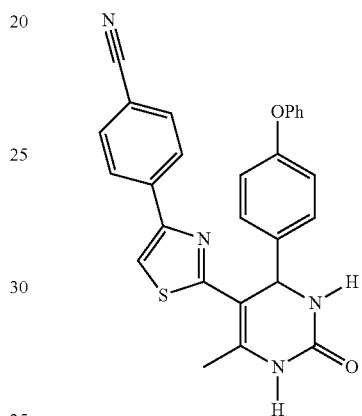 |
| Example 56 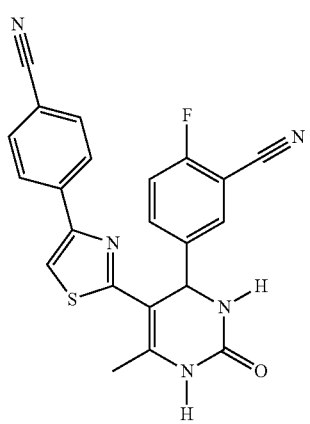 | Example 60 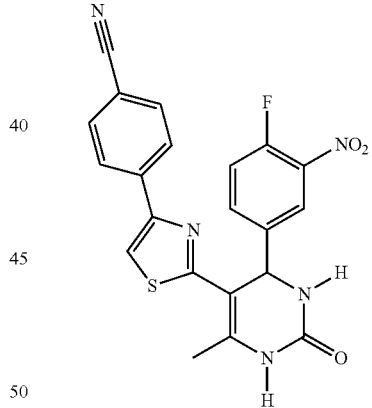 |
| Example 57 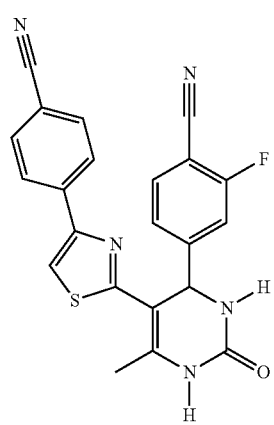 | Example 61 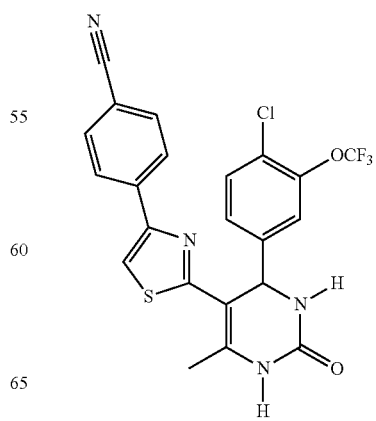 |

| | |
|---|---|
| 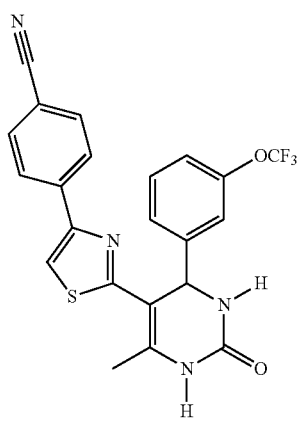 Example 62 | 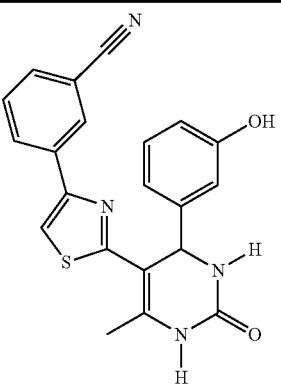 Example 66 |
| 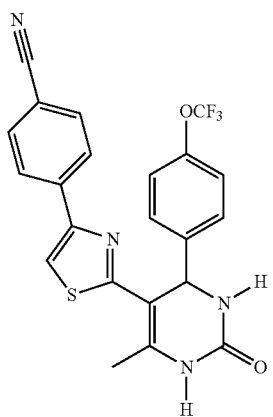 Example 63 | 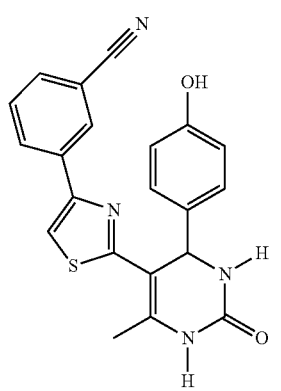 Example 67 |
| 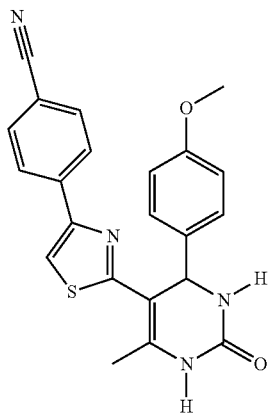 Example 64 | 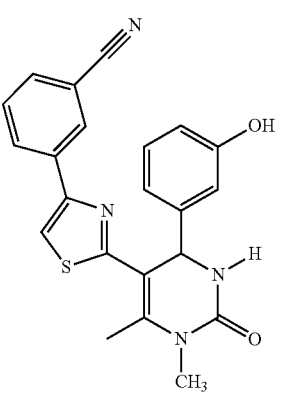 Example 68 |
| 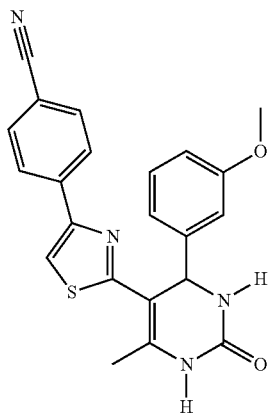 Example 65 | 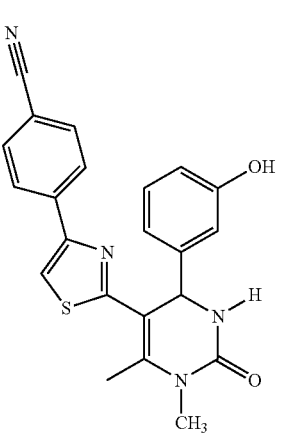 Example 69 |

| | |
|---|---|
| Example 70 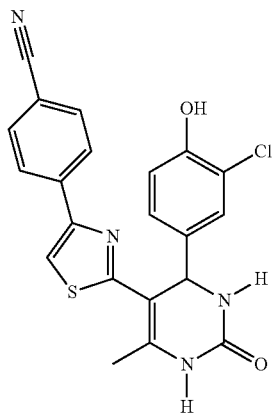 | Example 74 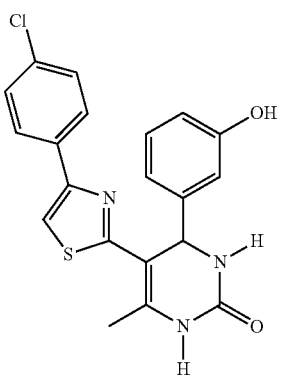 |
| Example 71 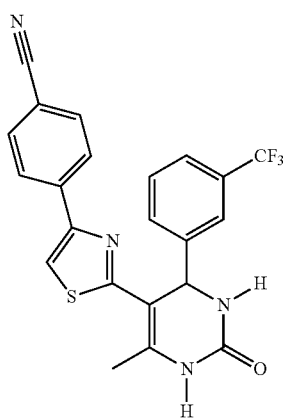 | Example 75 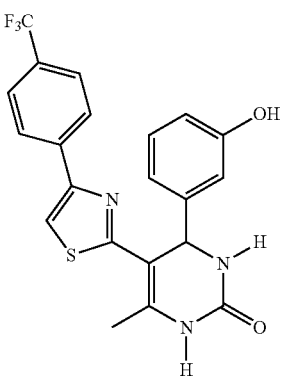 |
| Example 72 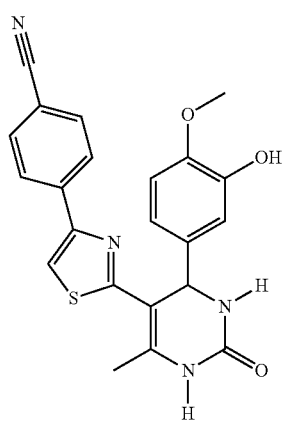 | Example 76 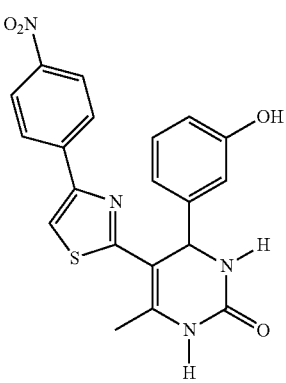 |
| Example 73 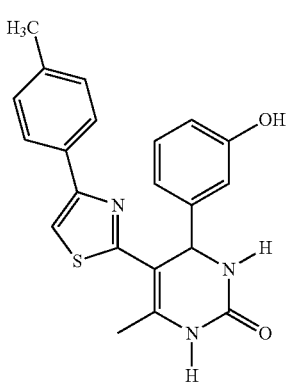 | Example 77 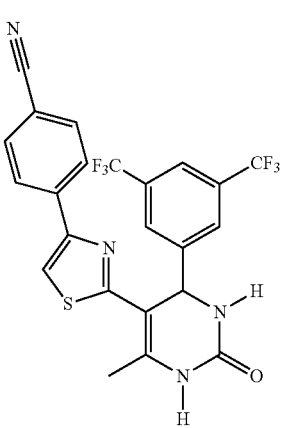 |

-continued
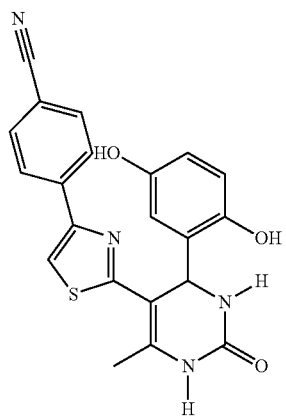
Example 78
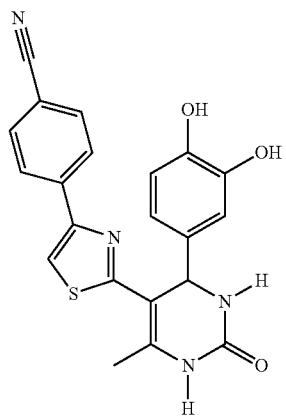
Example 79
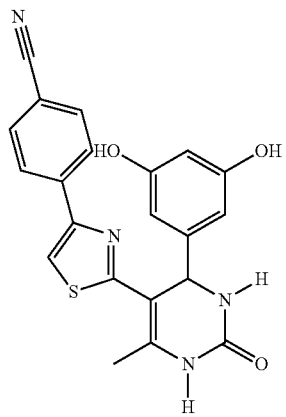
Example 80
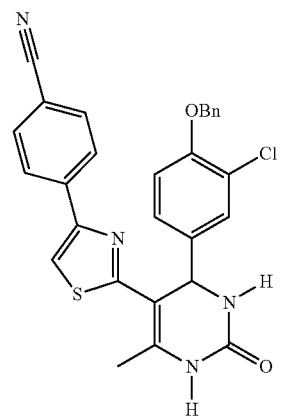
Example 81
-continued
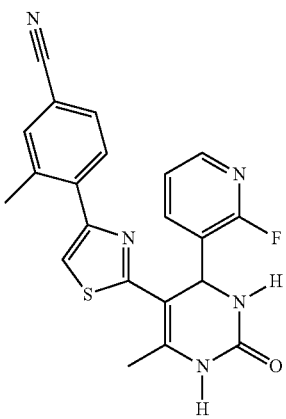
Example 82
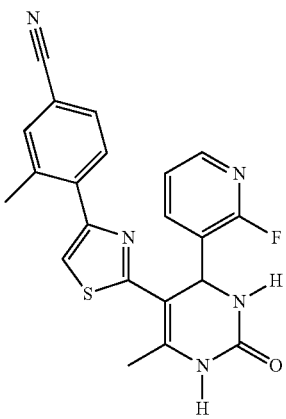
Example 83
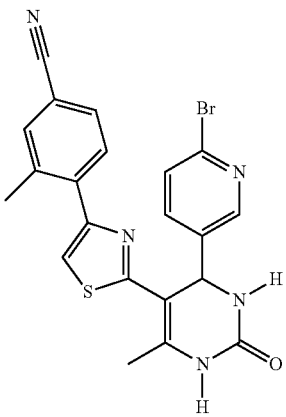
Example 84
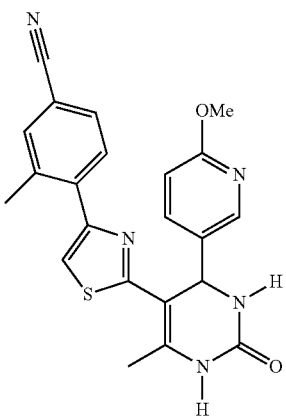
Example 85

Example 86
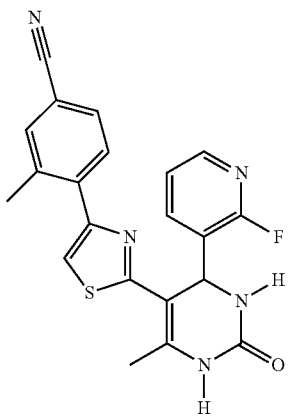
Example 87
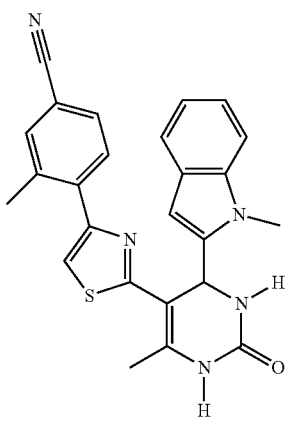
Example 88
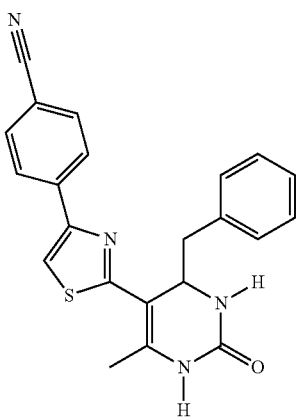
Example 89
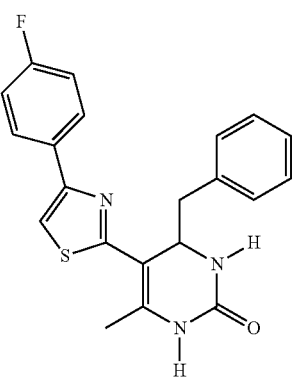
Example 90
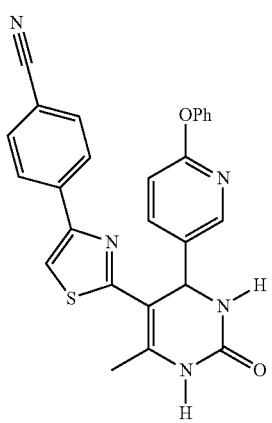
Example 91
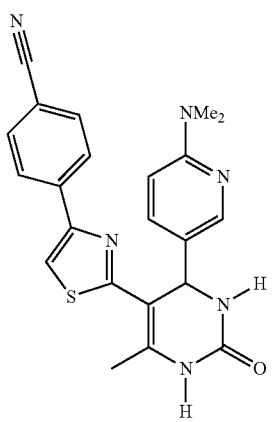
Example 92
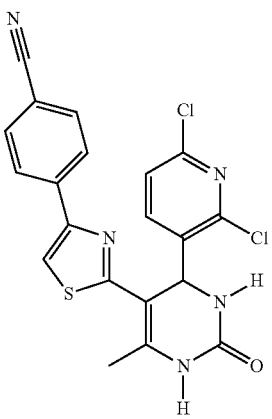
Example 93
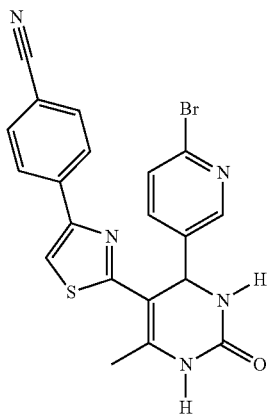

-continued

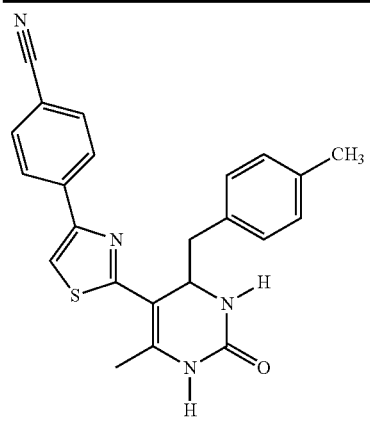

Example 94

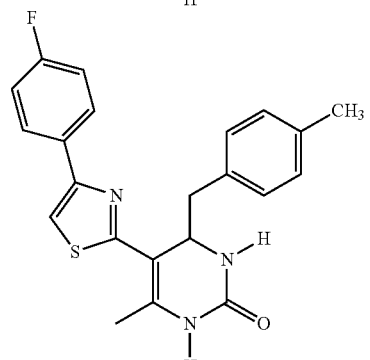

Example 95

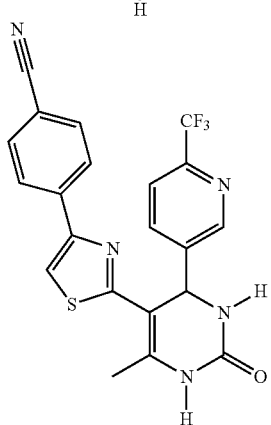

Example 96

G) Evaluation of Dihydropyrimidines in Anti-viral Assays

The anti-viral activity of dihydropyrimidines was shown by inhibition of virus replication in MAGI-CCR5 cells. MAGI-CCR5 cells are derived from HeLa-CD4-LTR-β-galactosidase cells. The cells have been engineered to express high levels of CD4 and CCR5 and contain one copy of the HIV-1 LTR promoter driving expression of the β-galactosidase gene upon HIV-1 Tat transactivation. On the day preceding the assay, the cells were plated at $1.0 \times 10^4$ cells per well and maintained at 37° C. and 5% $CO_2$ in a humidified incubator. Total cell count and viability was visually assessed using a hemacytometer and trypan blue exclusion.

Compounds were evaluated at six concentrations (triplicate wells/concentration). On the day of assay setup, compound dilutions were prepared at two-times (2×) the final concentrations. Media was decanted and wells were replenished with 50 µl of 2× compounds, followed by the addition of 50 µl of diluted virus. Identical uninfected assays were prepared for parallel cytotoxicity testing. The cultures were incubated for 48 hours after which efficacy was measured by the inhibition of β-galactosidase reporter expression and cytotoxicity was measured by MTS staining.

Evaluation of Dihydropyrimidines vs. HIV-$1_{Ba-L}$ in MAGI-CCR5 Cells

A=$IC_{50} \leq 1.0$ µM, B>1.0 to 5.0 µM, C>5.0 µM to 100 µM and D>100 µM

A=$TC_{50} \geq 100.0$ µM, B<100.0 to 50 µM and C<50 µM

A=TI ($TC_{50}/IC_{50}$)≥100.0, B<100.0-50.0, C<50.0-10.0 and D<10.0

| Compound | $IC_{50}$ (µM) | $TC_{50}$ (µM) | TI ($TC_{50}/IC_{50}$) |
|---|---|---|---|
| Example 3 | B | A | A |
| Example 4 | B | A | C |
| Example 5 | C | A | D |
| Example 6 | B | A | C |
| Example 7 | B | A | C |
| Example 8 | B | A | C |
| Example 9 | B | A | C |
| Example 10 | B | C | C |
| Example 11 | A | A | A |
| Example 12 | B | A | C |
| Example 13 | C | A | D |
| Example 14 | C | A | C |
| Example 15 | B | A | B |
| Example 16 | D | A | D |
| Example 18 | D | A | D |
| Example 19 | B | A | B |
| Example 20 | A | A | A |
| Example 21 | D | A | D |
| Example 22 | D | A | D |
| Example 23 | A | B | A |
| Example 24 | C | A | C |
| Example 25 | A | A | A |
| Example 26 | C | A | D |
| Example 27 | C | A | C |
| Example 28 | B | A | B |
| Example 29 | A | A | A |
| Example 30 | D | A | D |
| Example 31 | B | A | C |
| Example 32 | C | A | D |
| Example 33 | C | A | D |
| Example 34 | A | A | A |
| Example 35 | B | B | C |
| Example 36 | C | B | D |
| Example 37 | C | A | D |
| Example 38 | C | B | D |
| Example 39 | C | A | D |
| Example 40 | D | A | D |
| Example 41 | C | B | D |
| Example 42 | D | A | D |
| Example 43 | D | A | D |
| Example 44 | B | B | C |
| Example 45 | D | A | D |
| Example 46 | C | A | D |
| Example 48 | A | A | A |
| Example 49 | B | A | C |
| Example 50 | B | A | C |
| Example 51 | C | A | C |
| Example 52 | B | A | C |
| Example 53 | B | A | C |
| Example 54 | C | B | C |
| Example 55 | C | A | C |
| Example 56 | C | A | C |
| Example 57 | C | A | C |
| Example 58 | B | A | C |
| Example 59 | A | A | A |
| Example 60 | C | A | C |
| Example 61 | C | A | D |
| Example 62 | C | A | D |
| Example 63 | C | A | D |
| Example 64 | A | C | B |
| Example 65 | B | A | C |
| Example 66 | C | B | D |
| Example 67 | C | B | D |
| Example 68 | C | A | D |
| Example 69 | B | A | B |
| Example 71 | B | A | B |
| Example 72 | A | A | A |

-continued

| Compound | IC$_{50}$ (µM) | TC$_{50}$ (µM) | TI (TC$_{50}$/IC$_{50}$) |
|---|---|---|---|
| Example 73 | C | B | D |
| Example 74 | B | B | C |
| Example 75 | C | C | D |
| Example 76 | A | A | A |
| Example 77 | D | A | D |
| Example 78 | C | A | D |
| Example 79 | A | A | A |
| Example 80 | D | A | D |
| Example 81 | B | A | B |
| Example 82 | A | B | A |
| Example 83 | A | C | B |
| Example 84 | A | C | B |
| Example 85 | A | C | B |
| Example 86 | A | A | A |
| Example 87 | A | A | A |
| Example 88 | B | A | C |
| Example 89 | D | A | D |
| Example 90 | A | A | A |
| Example 91 | A | A | A |
| Example 92 | A | A | A |
| Example 93 | A | A | A |
| Example 94 | B | B | C |
| Example 95 | D | A | D |
| Example 96 | A | A | A |
| TAK 779 | 0.004 | >10.0 | 2902.7 |
| AMD 3100 | >10.0 | >10.0 | N/A |
| AZT | 0.08 | >1.0 | >36.5 |
| Raltegravir | 0.026 | >100.0 | >3.85 |
| Maraviroc | 0.0006 | >1.0 | >2004.2 |
| TMC-125 (Etravirine) | 0.003 | >100.0 | >37,500.0 |

A = IC$_{50}$ ≤ 1.0 µM, B > 1.0 to 5.0 µM, C > 5.0 µM to 100 µM and D > 100 µM
A = TC$_{50}$ ≥ 100.0 µM, B < 100.0 to 50 µM and C < 50 µM
A = TI (TC$_{50}$/IC$_{50}$) ≥ 100.0, B < 100.0-50.0, C < 50.0 to 10.0 and D < 10.0

The dihydropyrimidine analogs are shown to inhibit the activity of the HIV-1 RT enzyme as shown in biochemical RT assay.

Evaluation of Dihydropyrimidines vs. HIV-1$_{Ba-L}$ in Peripheral Blood Mononuclear Cells (PBMCs)

Cultures of pooled phytohemagglutinin stimulated peripheral blood mononuclear cells (PBMC) were seeded into a 96-well plate at plating density of 5×10$^4$ cells/well. Compounds were serially diluted into media in ½-log increments using a high test of 100 mM and 100 ml of each concentration (nine total concentrations). Cells were infected with HIV strains HIV-1$_{Ba-L}$ and NL4-3 at an MOI=0.1. The PBMCs were cultured for seven days in an humidified incubator maintained at 37° C., 5% CO$_2$ atmosphere. At the assay end-point, the supernatant was collected and analyzed for reverse transcriptase activity. For the RT assay, tritiated thymidine triphosphate (3H-TTP, 80 Ci/mmol) was diluted 1:1 dH$_2$O:Ethanol at 1 mCi/ml. Poly rA:oligo dT template:primer was prepared as a stock solution by combining 150 µl poly rA (20 mg/ml) with 0.5 mL oligo dT (20 units/ml) and 5.35 ml sterile dH$_2$O followed by aliquoting (1.0 ml) and storage at −20° C. The RT reaction buffer contained of 125 ml 1.0 M EGTA, 125 ml dH$_2$O, 125 ml 20% Triton X100, 50 ml 1.0 M Tris (pH 7.4), 50 ml 1.0 M DTT, and 40 ml 1.0 M MgCl$_2$. The final reaction mixture was prepared by combining 1 part 3H-TTP, 4 parts dH$_2$O, 2.5 parts poly rA:oligo dT stock and 2.5 parts reaction buffer. To each well, ten microliters of the reaction mixture and 15 µl of virus containing supernatant were added. The plates were incubated at 37° C. for 60 minutes. Following incubation, the reaction volume was spotted onto DE81 filtermats, washed 5 times for 5 minutes each in a 5% sodium phosphate buffer or 2×SSC. PBMCs were washed 2 times for 1 minute each in distilled water, 2 times for 1 minute each in 70% ethanol, and then dried. Incorporated radioactivity (counts per minute, CPM) was quantified using standard liquid scintillation techniques.

Cytotoxicity was assessed by MTS staining. At assay endpoint, PBMC were stained with the addition of 20 ml/well of the soluble tetrazolium-based dye MTS to determine cell viability and quantify compound toxicity. The plates were incubated 4 to 6 hrs at 37° C. Following incubation, the activity was assessed by reading absorbance values at 490/650 nm.

A=IC$_{50}$≤1.0 µM, B>1.0 to 5.0 µM, C>5.0 µM to 100 µM and D>100 µM
A=TC$_{50}$≥100.0 µM, B<100.0 to 50 µM and C<50 µM
A=TI (TC$_{50}$/IC$_{50}$)≥100.0, B<100.0-50.0, C<50.0-10.0 and D<10.0

| Compound | IC$_{50}$ (µM) | TC$_{50}$ (µM) | TI (TC$_{50}$/IC$_{50}$) |
|---|---|---|---|
| Example 3 | A | A | A |
| Example 10 | B | B | C |
| Example 11 | A | A | A |
| Example 15 | B | A | B |
| Example 18 | D | A | D |
| Example 19 | A | A | A |
| Example 21 | D | A | D |
| Example 23 | A | A | A |
| Example 25 | A | A | A |
| Example 26 | B | A | C |
| Example 28 | B | A | B |
| Example 29 | A | A | A |
| Example 30 | D | A | D |
| Example 33 | C | B | D |
| Example 34 | A | B | A |
| Example 34 (enantiomer) | C | A | D |
| Example 35 | B | B | C |
| Example 36 | C | C | D |
| Example 38 | C | B | D |
| Example 40 | C | A | D |
| Example 42 | C | A | D |
| Example 43 | C | A | D |
| Example 44 | C | B | D |
| Example 48 | A | A | A |
| Example 50 | A | A | A |
| Example 59 | A | A | A |
| Example 64 | A | A | A |
| Example 68 | C | B | D |
| Example 69 | B | A | C |
| Example 71 | C | A | C |
| Example 74 | B | B | C |
| Example 80 | B | A | B |
| Example 81 | A | A | A |
| Example 86 | A | A | A |
| Example 87 | A | A | A |
| Example 89 | C | A | D |
| Example 90 | B | B | C |
| Example 91 | B | A | B |
| Example 92 | B | B | C |
| Example 93 | A | A | A |
| Example 96 | A | A | A |
| TAK 779 | 0.35 | >10.0 | >29.9 |
| AMD 3100 | >10.0 | >10.0 | N/A |
| AZT | 0.02 | >1.0 | >54.9 |
| Indinavir | 0.048 | >1.0 | >21.0 |
| Raltegravir | 0.003 | >1.0 | >371.0 |
| Maraviroc | 0.009 | >1.0 | >231.2 |
| TMC-125 (Etravirine) | 0.003 | >1.0 | >325.0 |

A = IC$_{50}$ ≤ 1.0 µM, B > 1.0 to 5.0 µM, C > 5.0 µM to 100 µM and D > 100 µM
A = TC$_{50}$ ≥ 100.0 µM, B < 100.0 to 50 µM and C < 50 µM
A = TI (TC$_{50}$/IC$_{50}$) ≥ 100.0, B < 100.0-50.0, C < 50.0-10.0 and D < 10.0

The dihydropyrimidine analogs are shown to inhibit the activity of the HIV-1 RT enzyme as shown in biochemical RT assay.

Enantiomers of Example 34 were created and utilized to assess the activity of the compounds in a biochemical reverse transcriptase assay. Purified recombinant HIV$_{NL4-3}$ heterodimeric (p66/p51) Reverse Transcriptase (RT) was used in experiments. RT activity was determined by the incorporation of radiolabeled deoxyribonucleotides into the newly synthesized DNA strand. The standard RT reaction mixture contained a synthetic homopolymeric template/primer [poly (rA)/oligo(dT)] or in vitro transcribed viral RNA derived from the HIV-1$_{NL4-3}$ 5'-LTR region (nucleotide residues 454 to 652) and a primer complementary to the primer binding site (PBS, nucleotide residues 636 to 652), radiolabeled deoxyribonucleotide, dNTPs and RT. The reaction was carried out in a volume of 40 μl containing 50 mM Tris HCl, pH 7.8, 50 mM KCl, 5 mM MgCl$_2$, 1 mM DTT, 50 μM each of dATP, dCTP, dGTP, 50 nM dTTP, 1 μCi of [$^3$H] dTTP (70-90 Ci/mM) and 5 nM template/primer. The reaction was initiated by the addition of 10 nM RT. For compound screening, serially diluted test articles were added to the reaction followed by the addition of RT. The reaction mixture was incubated at 37° C. for 1 h, then quenched by the addition of ice-cold trichloroacetic acid (TCA) to the final concentration of 10%. The plate was incubated at 4° C. for 1 h to precipitate the synthesized DNA, then rinsed 3-times with 10% TCA and 1 time with 70% ethanol. After addition of 25 μl scintillation fluid to completely dried wells, radioactivity is counted by MicroBeta scintillation counter. The reduction of radioactivity represents the potency of compound inhibition.

Activity of Example 34 Enantiomers Against HIV RT in a Biochemical Assay

A=IC$_{50}$≤1.0 μM, B>1.0 to 5.0 μM, C>5.0 μM to 100 μM and D>100 μM

| Compound Name | High-Test (μM) | 5'LTR/dPR IC$_{50}$(μM) |
|---|---|---|
| Nevirapine | 10.0 | 0.29 |
| | | 0.19 |
| Efavirenz | 10.0 | 0.01 |
| | | 0.01 |
| AZT-TP | 1.0 | 0.009 |
| | | 0.01 |
| TMC-125 (Etravirine) | 250 | 0.19 |
| Example 34 | 250 | A |
| Example 34 (enantiomer) | 250 | D |

In addition, viral resistance to DHPMs is demonstrated by the abolishment of antiviral activity against viruses where amino acids in the NNRTI binding pocket are changed relative to wild type. Changes in the binding site amino acids K103 to an Asparagine and Y181 to cysteine were shown to inhibit the anti-viral activity of Example 11 and Example 19. The asparagine variation at residue 103 and the cysteine variation at residue 181 are known to inhibit the activity of the NNRTI's.

Evaluation Dihydropyrimidines vs. HIV-1$_{Ba-L}$ and HIV-1 K103N, Y181C in PBMCs

| Compound | Virus | IC$_{50}$ (μM) | TC$_{50}$ (μm) | TI (TC$_{50}$/IC$_{50}$) |
|---|---|---|---|---|
| Example 10 | Ba-L | B | A | B |
| | A17 | C | A | D |
| Example 11 | Ba-L | A | A | A |
| | A17 | D | A | D |
| Example 19 | Ba-L | A | A | A |
| | A17 | D | A | D |
| Example 21 | Ba-L | D | A | D |
| | A17 | D | A | D |
| Example 42 | Ba-L | C | A | D |
| | A17 | C | A | D |
| Example 86 | Ba-L | A | A | A |
| | A17 | C | A | D |
| Example 87 | Ba-L | A | A | A |
| | A17 | C | A | C |
| Example 89 | Ba-L | D | A | D |
| | A17 | D | A | D |
| Example 93 | Ba-L | A | A | A |
| | A17 | D | A | D |
| Example 96 | Ba-L | A | A | A |
| | A17 | C | A | D |
| Etravirine | Ba-L | 0.003 | >1.0 | >402.0 |
| (TMC-125) | A17 | 0.010 | >1.0 | >101.0 |
| AZT | Ba-L | 0.011 | >1.0 | >88.6 |
| | A17 | 0.0016 | >1.0 | >629.0 |

A = IC$_{50}$ ≤ 1.0 μM, B > 1.0 to 5.0 μM, C > 5.0 μM to 100 μM and D > 100 μM
A = TC$_{50}$ ≥ 100.0 μM, B < 100.0 to 50 μM and C < 50 μM
A = TI (TC$_{50}$/IC$_{50}$) ≥ 100.0, B < 100.0-50.0, C < 50.0-10.0 and D < 10.0

Compatibility of Dihydropyrimidines in Combination with the Current Standard of Care The dihydropyrimidines were tested in combination with two FDA-approved drugs that are used in the first line regimen. Three dihydropyrimidines were each tested in combination with tenofovir to assess the impact to cytotoxicity in CEM-SS and antiviral activity against HIV$_{IIIB}$. Tenofovir (a nucleoside reverse transcriptase inhibitor; NRTI) in combination with Emtricitabine (NRTI) and Tenofovir in combination with Efavirenz (a non-nucleoside reverse transcriptase inhibitor; NNRTI) were the standard of care references.

The compounds were diluted in ½-log increments. The high test concentrations for the drugs were 100 μM for the DHPM, 50 μM for Tenofovir (TFV), 500 nM for Emtricitabine (FTC), 100 nM for Efavirenz (EFV), 20 μM for Stavudine, and 10 μM for Ribavirin (Rib). There were 6-dilutions of Drug A and 9-dilutions of Drug B, and there were three efficacy plates set up and 2 cytotoxicity plates set up. The plates were set up as shown below Plate Map for Drug Testing with Two Drugs in Combination

| Drug A (nM) | | 1 | 2 | 3 | 4 | 5 | 6 | 7 | 8 | 9 | 10 | 11 | 12 |
|---|---|---|---|---|---|---|---|---|---|---|---|---|---|
| | A | | | | | | | | | | | | |
| | B | | | | | | | | | | Cell Control | | |
| 50 | C | | | | | | | | | | Cell Control | | |
| 16 | D | | | | | | | | | | Cell Control | | |
| 5 | E | | | | | | | | | | Virus Control | | |
| 1.6 | F | | | | | | | | | | Virus Control | | |
| 0.5 | G | | | | | | | | | | Virus Control | | |
| 0 | H | | | | | | | | | | | | |
| Drug B (μM) | | 0 | 0.032 | 0.1 | 0.32 | 1 | 3.2 | 10 | 32 | 100 | | | |

FIG. 1: Plate Map for Drug Testing with Two Drug Combinations: Areas shaded gray contain media only. Areas shaded orange contain CEM-SS cells only. Areas shaded blue contain CEM-SS cells infected with HIVIIIB. Areas colored white contain cells infected with virus and different concentrations of the two drugs. For example, well C2 would contain 50 nM Drug A and 0.032 mM Drug B.

MacSynergy was used to assess the effect on potency and cytotoxicity when combining two drugs in an experiment. MacSynergy calculates an expected effect for each well using the Bliss Independence model. This model assumes the two drugs are acting independently to affect virus replication. Bliss independence can be expressed as Z=X+Y(1−X). For example, if drug A inhibits virus replication by 60% and drug B by 25% then using the model would predict the combination to inhibit virus replication by 70% in an experimental system [0.6+0.25(1.0−0.6)=0.7]. Data are graphed using the surface function in excel. The independent data are plotted on the X and Y axis (the concentrations of the two drugs); the x-axis contains the concentration of drug A the y-axis the concentration of drug B. The dependent variable (the biological effect) is plotted on the z-axis; the percent inhibition observed relative to the expected value. The volume of the 3D dose surface is calculated. Synergy is defined as greater than the expected effect, and antagonism is defined as less than the expected effect. The extent to which a combination is synergistic or antagonistic is defined in Table 2.

TABLE 1

Synergy and Antagonism Legend

| Volume | Interpretation |
|---|---|
| A | Compound interactions highly synergize efficacy or cytotoxicity |
| B | Compound interactions slightly synergize efficacy or cytotoxicity |
| C | Additive |
| D | Compound interactions slightly antagonize efficacy or cytotoxicity |
| E | Compound interactions highly antagonize efficacy or cytotoxicity |

The dihydropyrimidines were tested in combination with Tenofovir in uninfected CEM-SS cells to assess the impact of combining these compounds on cytotoxicity. The results are shown in Table 4.

TABLE 2

Experimental Synergy and Antagonism Volumes Observed

| CID | | Antiviral | | Cytotoxicity | |
|---|---|---|---|---|---|
| Drug A | Drug B | Synergy | Antagonism | Synergy | Antagonism |
| d4T | Ribavirin | C | E | C | C |
| Tenofovir | FTC | C | C | C | C |
| Tenofovir | Efavirenz | C | C | C | C |
| Tenofovir | Example 48 | B | C | C | C |
| Tenofovir | Example 25 | C | C | C | D |
| Tenofovir | Example 64 | C | C | B | C |

1 = Maximum percent inhibition above expected effect for synergy. (See Table 1 for explanation of values).
2 = Maximum percent inhibition below expected effect for antagonism. (See Table 1 for explanation of values).
* Cytotoxicity adjusted values These studies show that the dihydropyrimidines do not adversely affect Tenofovir in combination.

Exemplary embodiments of the present disclosure include:

Embodiment 1

A compound represented by the following Formula I:

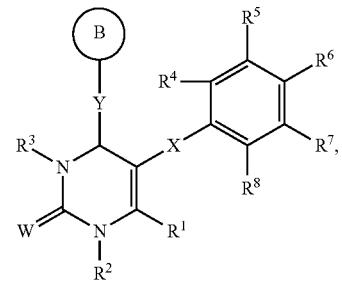

wherein B is selected from the group consisting of substituted or unsubstituted aryl, substituted or unsubstituted heteroaryl;
W is O, S, or NR;
Y is a linker moiety selected from the group consisting of a direct bond, O, S, NR, $C_1$-$C_8$ alkyl, $C_2$-$C_8$ alkenyl, $C_2$-$C_8$ alkynyl, $C_1$-$C_8$ alkoxy, $C_1$-$C_8$ thioalkyl, $C_1$-$C_8$ alkylNR;
R, $R^1$, $R^2$, and $R^3$ are each individually selected from the group consisting of H, $C_1$-$C_8$ alkyl, $C_1$-$C_8$ haloalkyl, $C_1$-$C_8$ alkylaryl, $C_{2-8}$ alkenyl, $C_{2-8}$ alkynyl, cycloalkyl, substituted or unsubstituted aryl, substituted or unsubstituted heteroaryl, or heterocycle;
X is

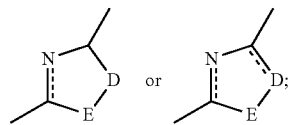

D and E are each individually selected from the group consisting of O, S, $NR^9$, CR or $CR^1R^2$;
$R^9$ is selected from the group consisting of H, $C_1$-$C_8$ alkyl, $C_1$-$C_8$ haloalkyl, $C_3$-$C_8$ cycloalkyl, $C_2$-$C_8$ alkenyl, $C_2$-$C_8$ alkynyl, $C_5$-$C_{10}$ aryl, $C_5$-$C_{10}$ heterocycle each of which is optionally substituted with halogen, —$OR^{10}$, —$NR^{11}R^{12}$, —$SR^{11}$, —$S(O)R^{11}$, —$S(O)_2R^{12}$, or —$S(O)_2NR^{11}R^{12}$;
$R^4$, $R^5$, $R^6$, $R^7$, and $R^8$ are each are independently selected from H, hydroxyl, halogen, cyano, $NO_2$, —$OR^{10}$, —$SR^{11}$, —$S(O)R^{11}$, —$S(O)_2R^{12}$, —$S(O)_2NR^{11}R^{12}$, $C_1$-$C_8$ haloalkyl, $COR^{13}$, —$C(O)OR^{12}$, —$C(O)NR^{11}R^{12}$, —$C(O)R^{12}$, —$NR^{11}R^{12}$, —$NR^{11}C(O)R^{12}$, —$NR^{11}S(O)_2R^{12}$, —$NR^{11}C(O)OR^{12}$, —$B(OH)_2$, $C_1$-$C_8$ alkyl, $C_3$-$C_8$ cycloalkyl, $C_2$-$C_8$ alkenyl, $C_2$-$C_8$ alkynyl, substituted or unsubstituted aryl, substituted or unsubstituted heteroaryl, -alkylC(O)—$OR^{12}$, -alkylC(O)$NR^{11}R^{12}$, -alkenylC(O)$OR^{12}$, -alkenylC(O)$NR^{11}R^{12}$, -aryl$(CH_2)_mC(O)OR^{12}$, -aryl$(CH_2)_mC(O)NR^{11}R^{12}$, —$(CH_2)_mC(O)NR^{11}S(O)_2R^{12}$, -aryl$(CH_2)_m$—C(O)$NR^{11}S(O)_2R^{12}$, —$(CH_2)_mS(O)_2NR^{11}C(O)R^{12}$, -aryl$(CH_2)_mS(O)_2NR^{11}C(O)R^{12}$, or substituted or unsubstituted heterocycle or substituted or unsubstituted heteroaryl containing 1 to 4 heteroatoms, optionally substituted with 1 to 2 substituents selected from the group consisting of H, hydroxyl, halogen, $CF_3$, $C_1$-$C_8$ alkyl, $C_1$-$C_8$ alkoxy, cyano, amino, $C_1$-$C_8$ alkylamino, and $C_1$-$C_8$ alkoxy$C_1$-$C_8$ alkylamino provided at least one of $R^4$, $R^5$, $R^6$, $R^7$, or $R^8$ is other than hydrogen;

$R^{10}$, $R^{11}$, $R^{12}$, and $R^{13}$ are each individually selected from the group consisting of H, $C_1$-$C_8$ alkyl, $C_1$-$C_8$ haloalkyl, $C_1$-$C_8$ alkylaryl, $C_{2-8}$ alkenyl, $C_{2-8}$ alkynyl, cycloalkyl, substituted or unsubstituted aryl, substituted or unsubstituted heteroaryl, or heterocycle;

m=0 to 6;

wherein alkyl, alkenyl, alkynyl, cycloalkyl, aryl, heteroaryl or heterocycle may be substituted or unsubstituted;

pharmaceutically acceptable salt thereof; solvate thereof and deuterated form thereof.

Embodiment 2

A compound according to Embodiment 1, wherein B is selected from the group consisting of aryl or substituted aryl.

Embodiment 3

A compound according to Embodiment 1, wherein B is selected from the group consisting of heteroaryl and substituted heteroaryl.

Embodiment 4

A compound according to any one of Embodiments 1-3, wherein Y is a direct bond.

Embodiment 5

A compound according to any one of Embodiments 1-4, wherein W is O.

Embodiment 6

A compound according to any one of Embodiments 1-5, wherein X is

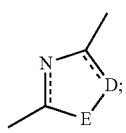

D is CH and E is S.

Embodiment 7

A compound according to any one of Embodiments 1-6, wherein $R^6$ is selected from the group consisting of CN, NO$_2$, $C_1$-$C_6$ alkyl, aryloxy and halo; each of $R^4$ and $R^8$ is independently H or a $C_1$-$C_6$ alkyl; and each of $R^5$ and $R^7$ is H.

Embodiment 8

A compound according to Embodiment 1 being represented by the formula II

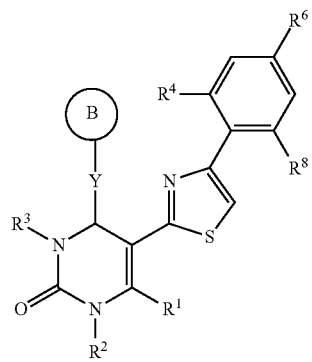

wherein B is selected from the group consisting of substituted or unsubstituted pyridinyl and when substituted the substitution is halo or $C_1$-$C_6$ alkoxy in the ortho position to the nitrogen in the pyridinyl ring or can be halo in the meta position when the nitrogen is in the 2-position; mono-substituted or unsubstituted quinolinyl and when substituted the substitution is hydroxyl; mono-substituted or unsubstituted indolyl and when substituted the substitution is $C_1$-$C_6$ alkyl; unsubstituted benzothiopheneyl; unsubstituted thiopheneyl; mono-substituted, or di-substituted or unsubstituted phenyl and when substituted the substitution is selected from the group consisting of hydroxyl, halo, CN, CF$_3$, $C_1$-$C_4$ alkoxy, and aryloxy; provided that when the phenyl is di-substituted the substitutions are located ortho to each other; and unsubstituted biphenyl;

Y is a direct bond or Y can be a $C_1$-$C_6$ alkyl when $R^5$ is CN;
$R^1$ is H, $C_1$-$C_6$ alkyl or $C_{3-8}$ cycloalkyl;
$R^2$ is H, $C_1$-$C_6$ alkyl or $C_{3-8}$ cycloalkyl;
$R^3$ is H;
each of $R^4$ and $R^8$ is independently H, $C_1$-$C_6$ alkyl or $C_{3-8}$ cycloalkyl;
$R^6$ is selected from the group consisting of CN, NO$_2$, aryloxy, and halo;
pharmaceutically acceptable salts thereof; solvates thereof and deuterated form thereof.

Embodiment 9

A compound according to Embodiment 1 represented by the formula III

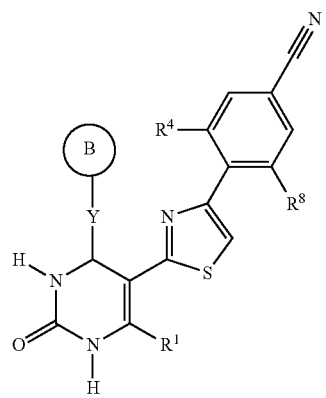

Wherein $R^1$ is H, $C_1$-$C_6$ alkyl or $C_{3-8}$ cycloalkyl; $R^4$ and $R^8$ are each independently H, $C_1$-$C_6$ alkyl or $C_{3-8}$ cycloalkyl;

and B is selected from the group consisting of phenyl substituted with at least one member selected from the group consisting hydroxyl, halo, $C_1$-$C_6$ alkoxy, aryloxy; pyridyl substituted with at least one member selected from the group consisting halo and $C_1$-$C_6$ alkoxy and indolyl substituted with a $C_1$-$C_6$ alkyl group; pharmaceutically acceptable salts thereof; solvates thereof and deuterated form thereof.

Embodiment 10

A compound according to Embodiment 1 being selected from the group consisting of

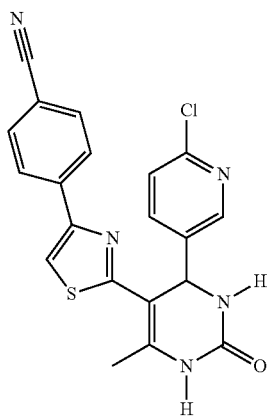

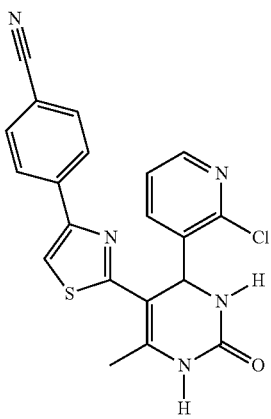

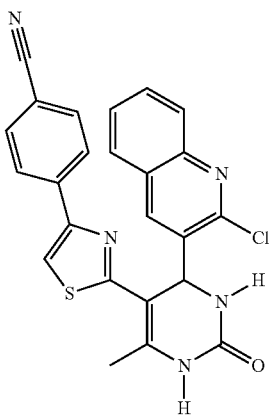

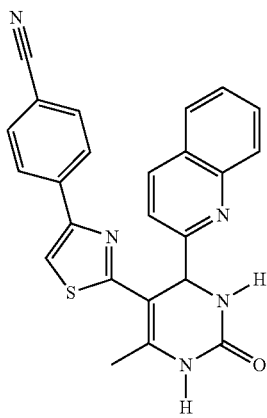

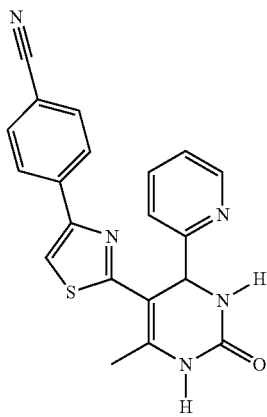

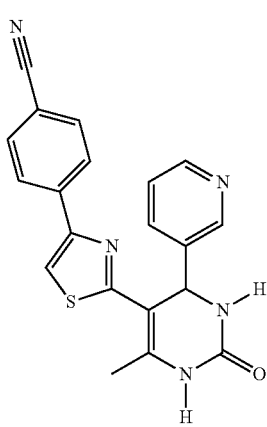 [SMILES: CC1=C(c2nc(-c3ccc(C#N)cc3)cs2)C(c2cccc(F)c2)NC(=O)N1]

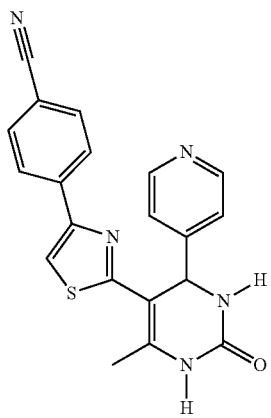
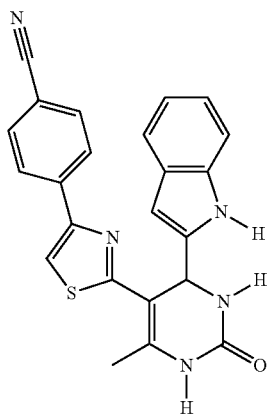
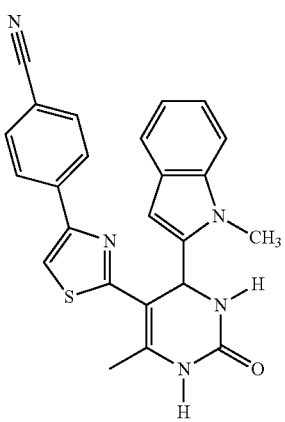
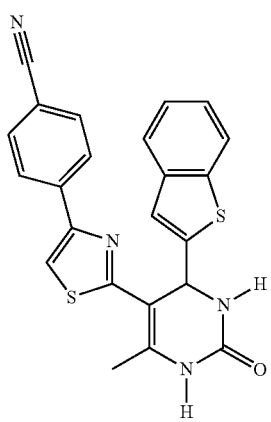
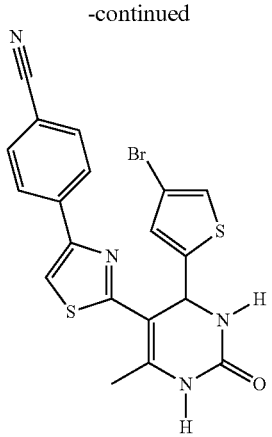
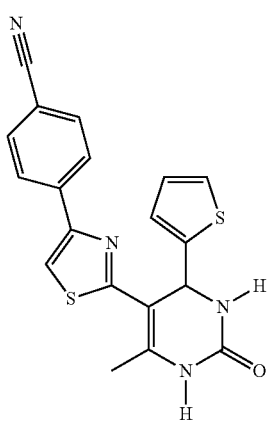
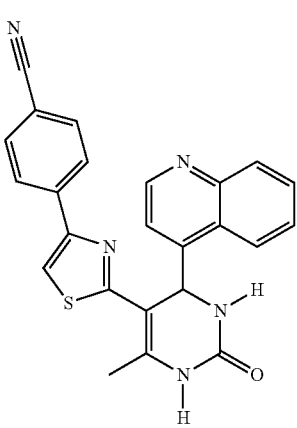
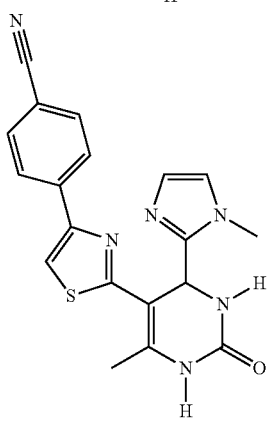

55
-continued
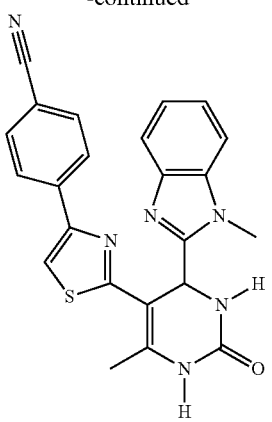
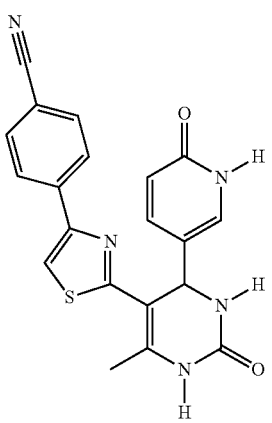
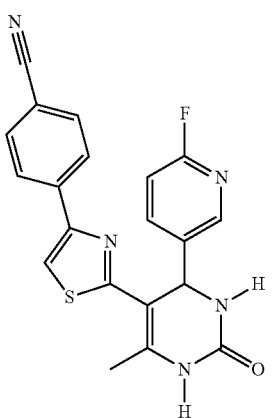
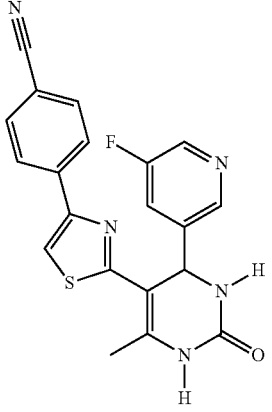
56
-continued
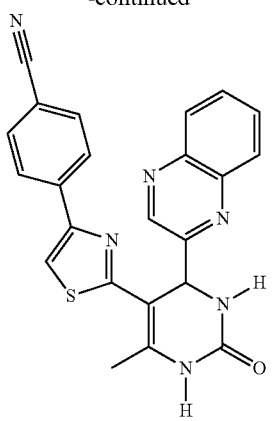
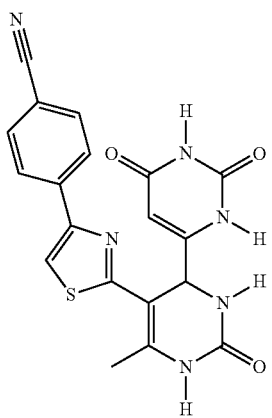
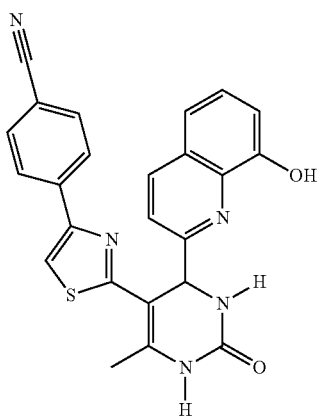
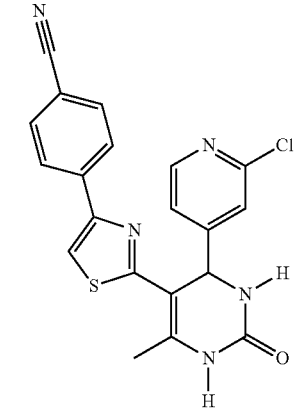 [SMILES: CC1=C(c2nc(-c3ccc(C#N)cc3)cs2)C(c2cccc(Cl)c2)NC(=O)N1]

57
-continued
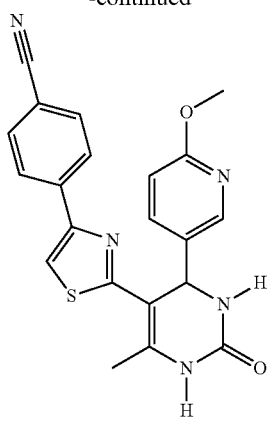
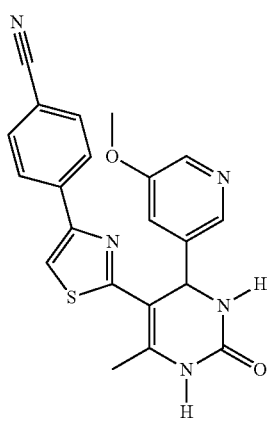
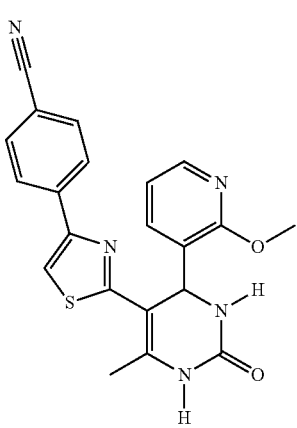
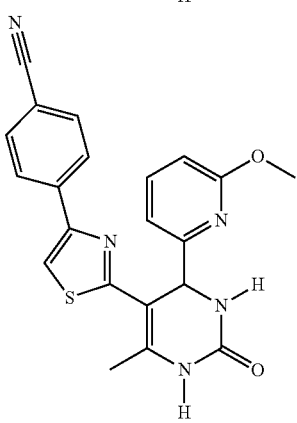
58
-continued
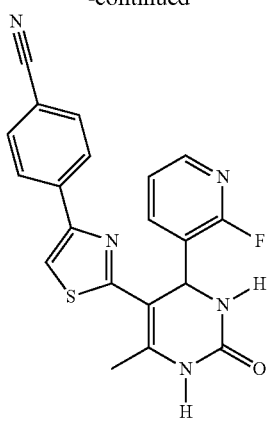
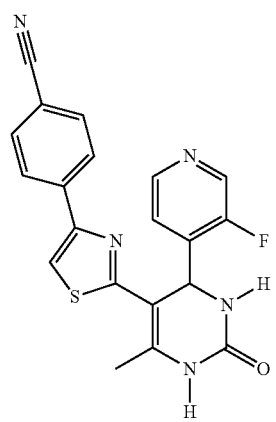
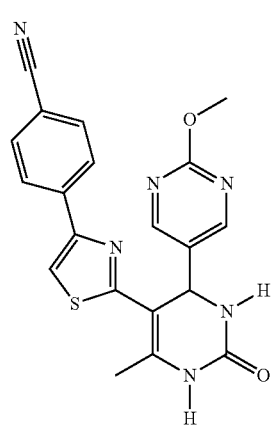
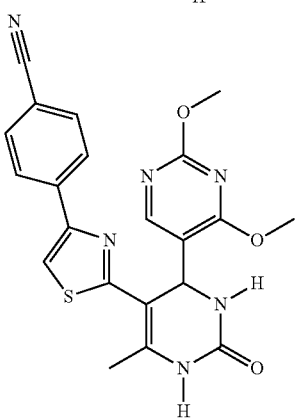

59
-continued
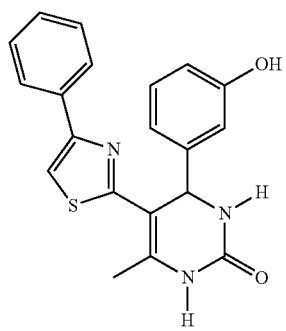
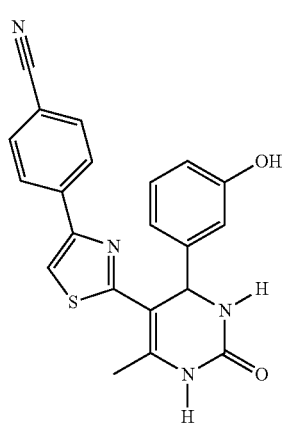
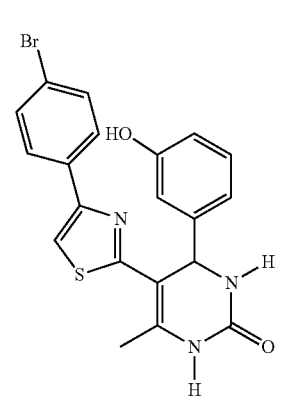
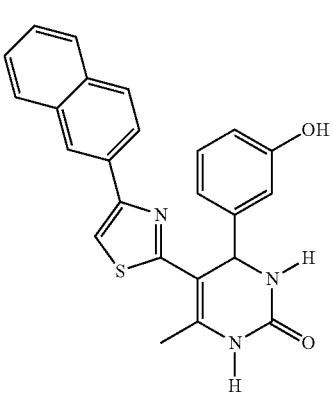
60
-continued
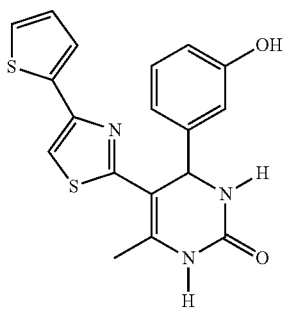
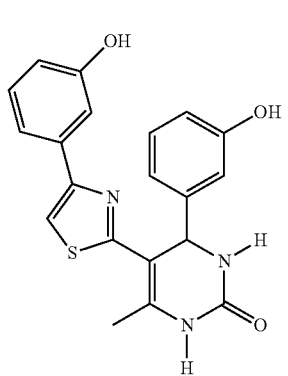
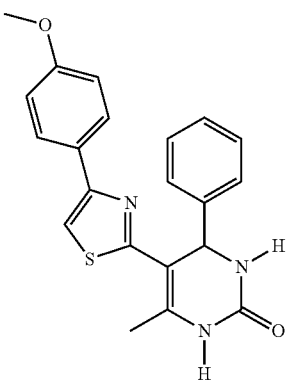
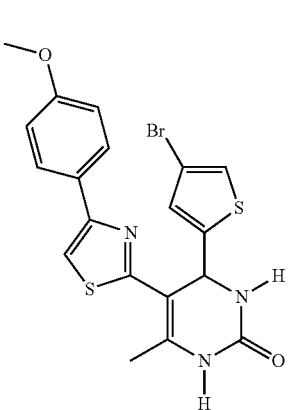

-continued
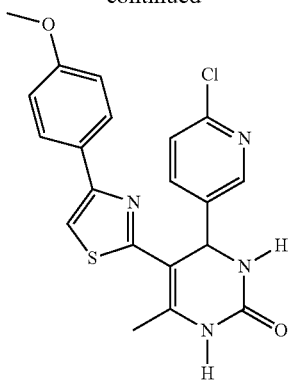
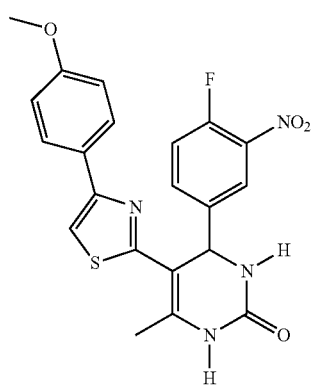
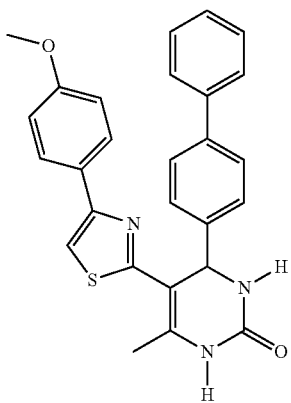
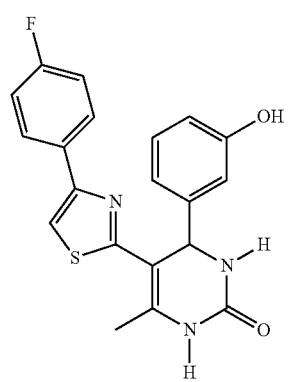
-continued
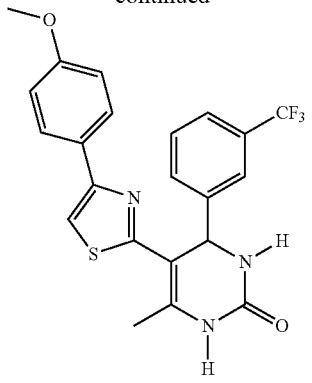
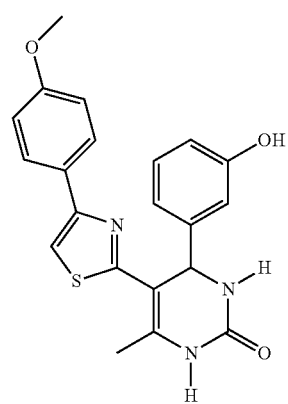
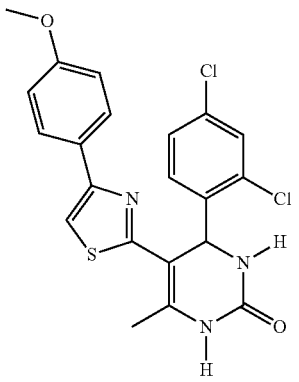
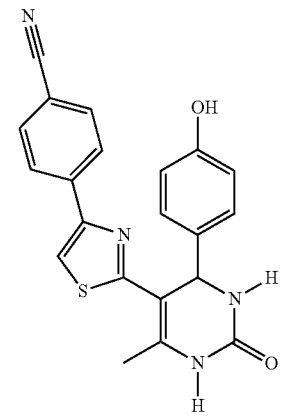

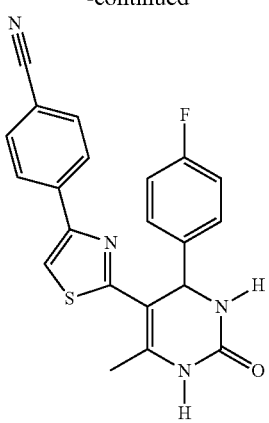
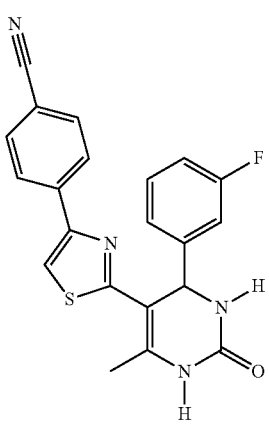
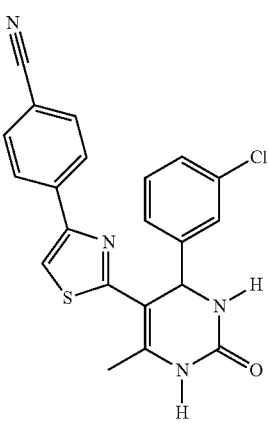
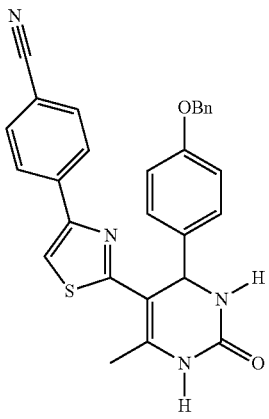 [SMILES: CC1=C(c2nc(-c3ccc(C#N)cc3)cs2)C(c2ccc(OCc3ccccc3)cc2)NC(=O)N1]
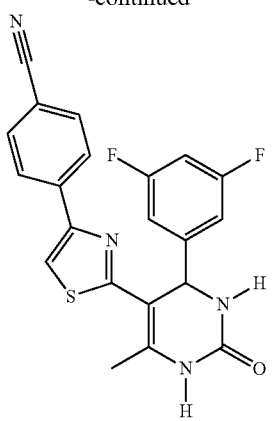

65
-continued
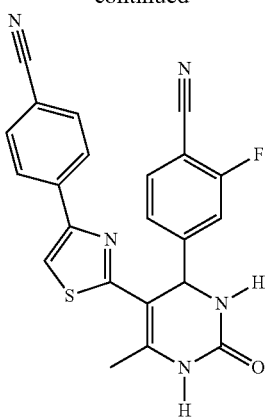
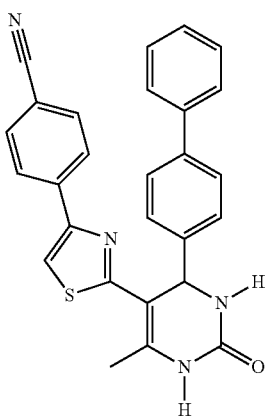 [SMILES: CC1=C(c2nc(-c3ccc(C#N)cc3)cs2)C(c2ccc(-c3ccccc3)cc2)NC(=O)N1]
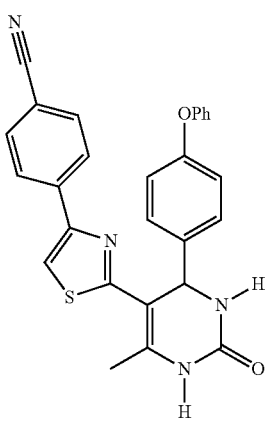 [SMILES: CC1=C(c2nc(-c3ccc(C#N)cc3)cs2)C(c2ccc(Oc3ccccc3)cc2)NC(=O)N1]
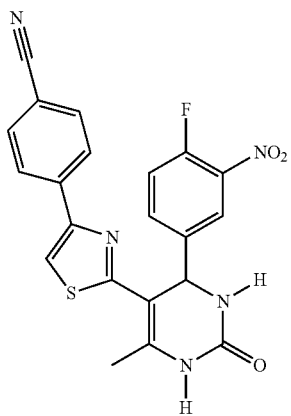 [SMILES: CC1=C(c2nc(-c3ccc(C#N)cc3)cs2)C(c2ccc(F)c([N+](=O)[O-])c2)NC(=O)N1]
66
-continued
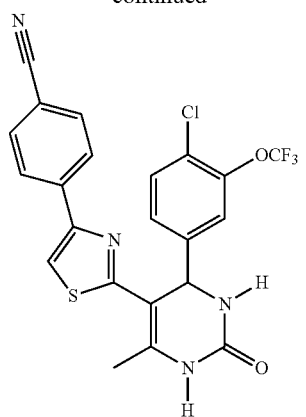
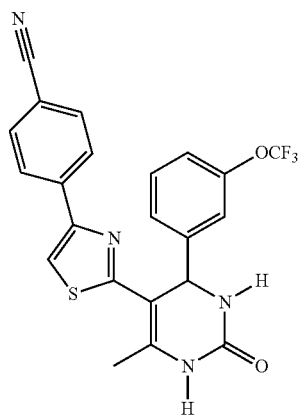 [SMILES: CC1=C(c2nc(-c3ccc(C#N)cc3)cs2)C(c2cccc(OC(F)(F)F)c2)NC(=O)N1]
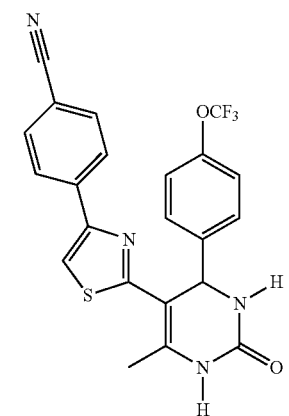 [SMILES: CC1=C(c2nc(-c3ccc(C#N)cc3)cs2)C(c2ccc(OC(F)(F)F)cc2)NC(=O)N1]
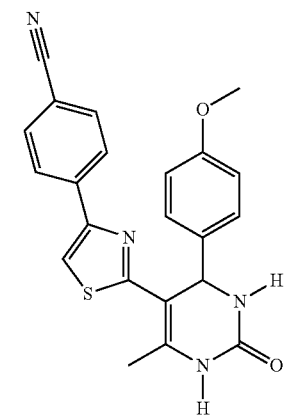 [SMILES: COc1ccc(C2NC(=O)NC(C)=C2c2nc(-c3ccc(C#N)cc3)cs2)cc1]

67
-continued
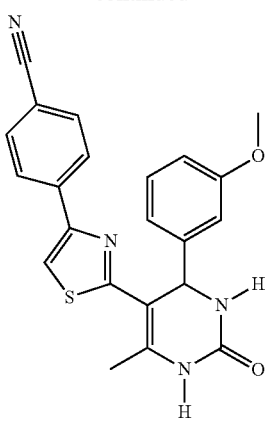 [SMILES: COc1cccc(C2NC(=O)NC(C)=C2c2nc(-c3ccc(C#N)cc3)cs2)c1]
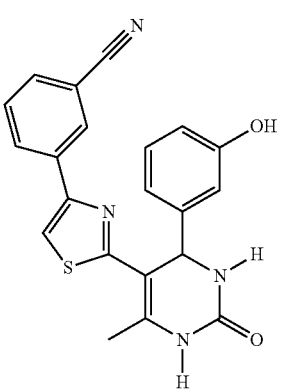 [SMILES: CC1=C(c2nc(-c3cccc(C#N)c3)cs2)C(c2cccc(O)c2)NC(=O)N1]
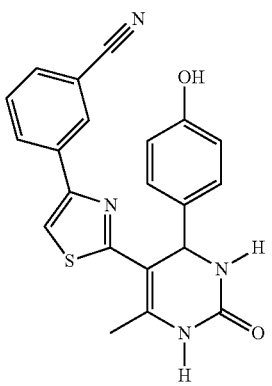 [SMILES: CC1=C(c2nc(-c3cccc(C#N)c3)cs2)C(c2ccc(O)cc2)NC(=O)N1]
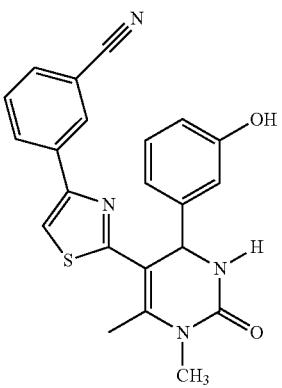 [SMILES: CC1=C(c2nc(-c3cccc(C#N)c3)cs2)C(c2cccc(O)c2)NC(=O)N1C]
68
-continued
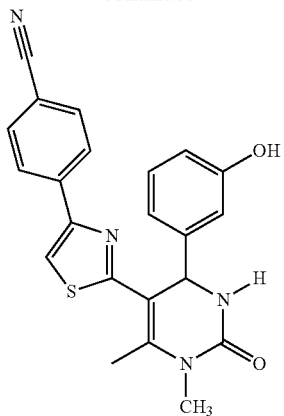 [SMILES: CC1=C(c2nc(-c3ccc(C#N)cc3)cs2)C(c2cccc(O)c2)NC(=O)N1C]
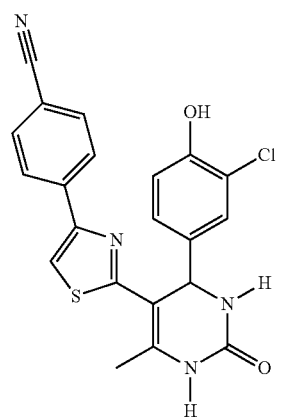 [SMILES: CC1=C(c2nc(-c3ccc(C#N)cc3)cs2)C(c2ccc(O)c(Cl)c2)NC(=O)N1]
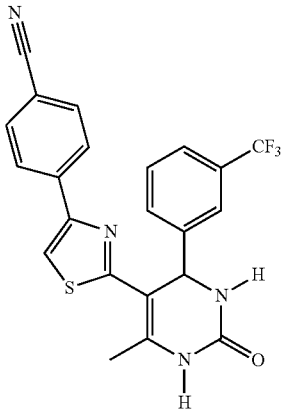 [SMILES: CC1=C(c2nc(-c3ccc(C#N)cc3)cs2)C(c2cccc(C(F)(F)F)c2)NC(=O)N1]
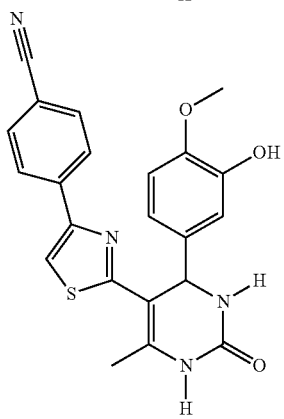

69
-continued
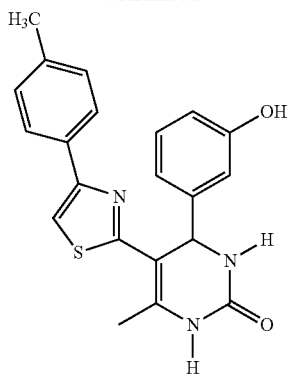
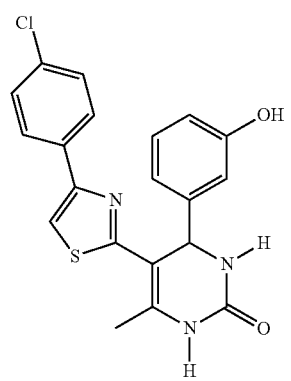 [SMILES: CC1=C(c2nc(-c3ccc(Cl)cc3)cs2)C(c2cccc(O)c2)NC(=O)N1]
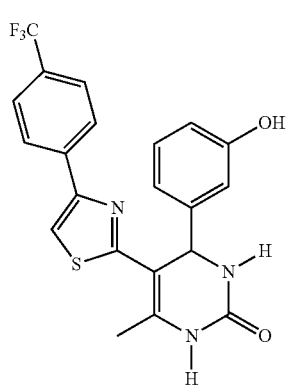 [SMILES: CC1=C(c2nc(-c3ccc(C(F)(F)F)cc3)cs2)C(c2cccc(O)c2)NC(=O)N1]
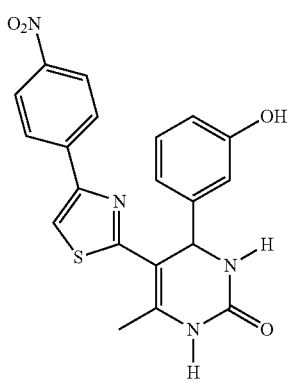 [SMILES: CC1=C(c2nc(-c3ccc([N+](=O)[O-])cc3)cs2)C(c2cccc(O)c2)NC(=O)N1]
70
-continued
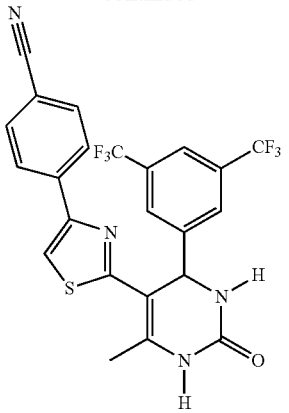 [SMILES: CC1=C(c2nc(-c3ccc(C#N)cc3)cs2)C(c2cc(C(F)(F)F)cc(C(F)(F)F)c2)NC(=O)N1]
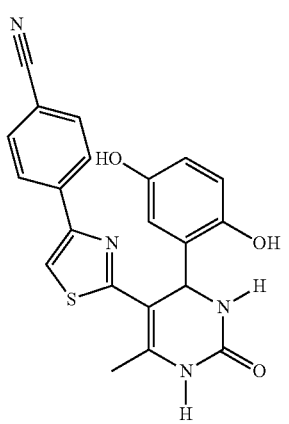 [SMILES: CC1=C(c2nc(-c3ccc(C#N)cc3)cs2)C(c2cc(O)ccc2O)NC(=O)N1]
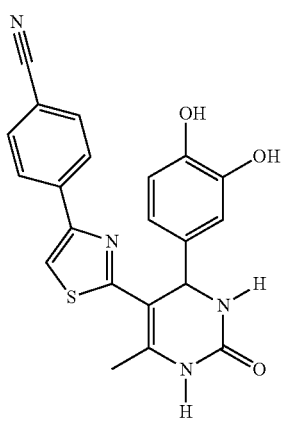 [SMILES: CC1=C(c2nc(-c3ccc(C#N)cc3)cs2)C(c2ccc(O)c(O)c2)NC(=O)N1]
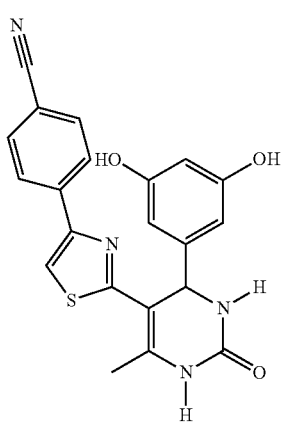 [SMILES: CC1=C(c2nc(-c3ccc(C#N)cc3)cs2)C(c2cc(O)cc(O)c2)NC(=O)N1]

-continued
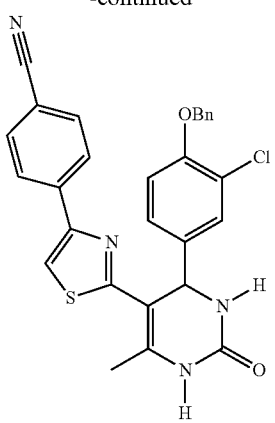
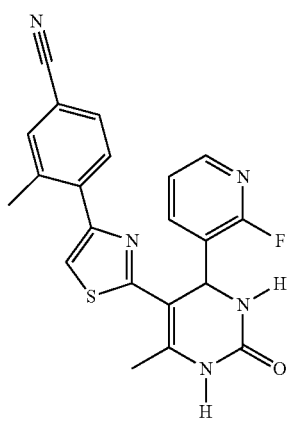
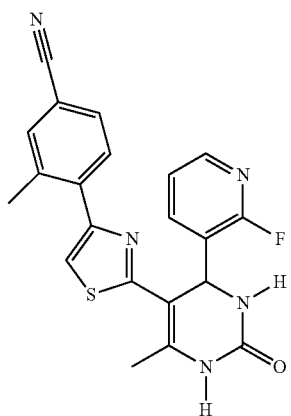
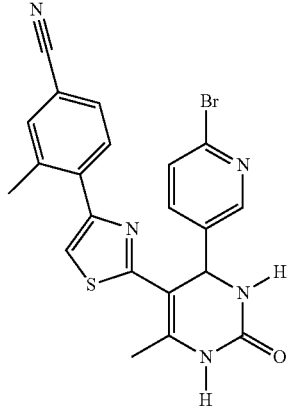
-continued
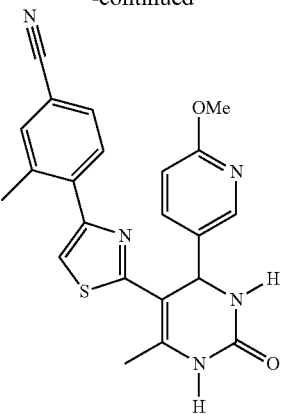
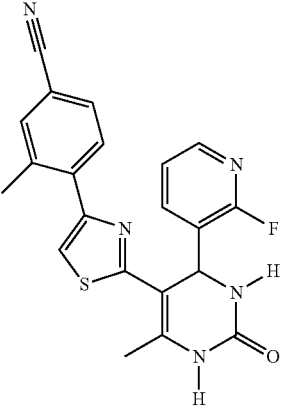
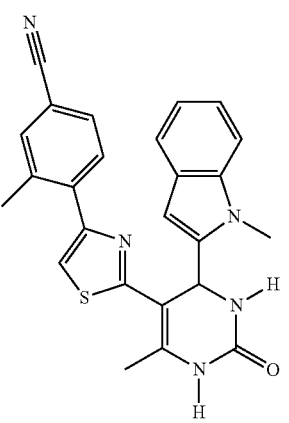
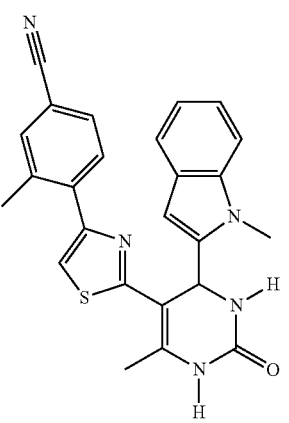

-continued
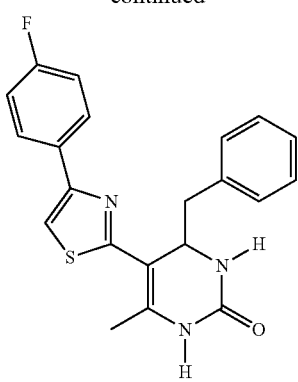
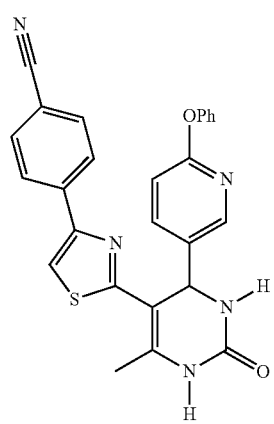
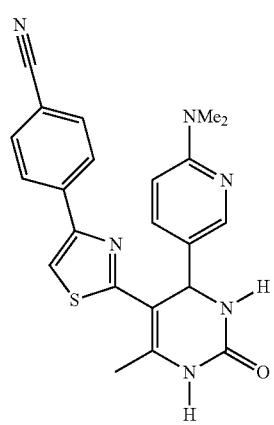
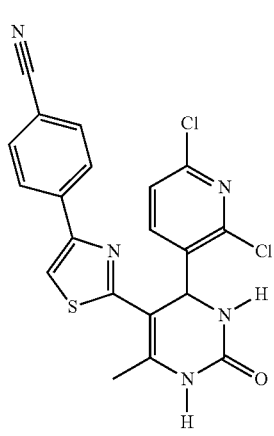
-continued
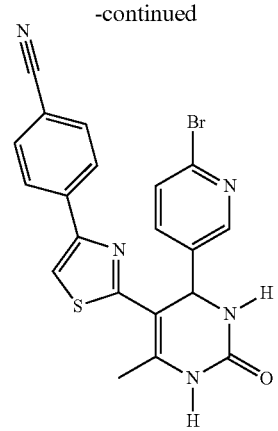
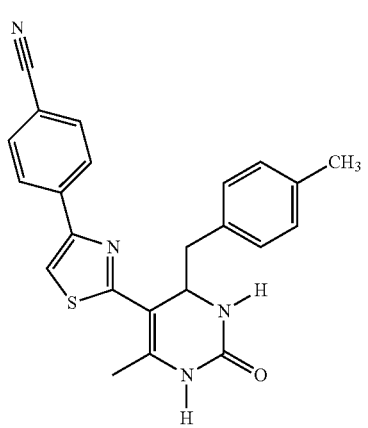
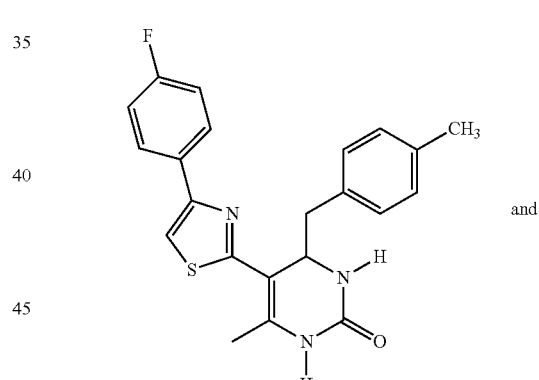
and
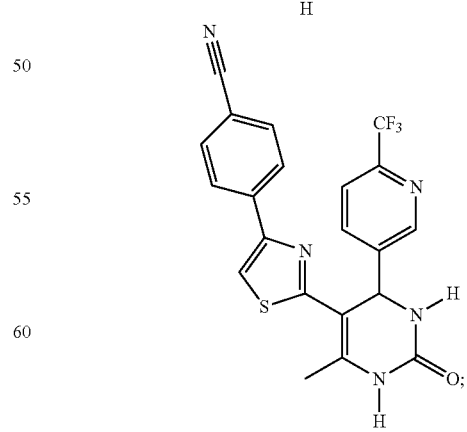
pharmaceutically acceptable salts thereof; solvates thereof and deuterated form thereof.

Embodiment 12
A compound according to Embodiment 1 being selected from the group consisting of
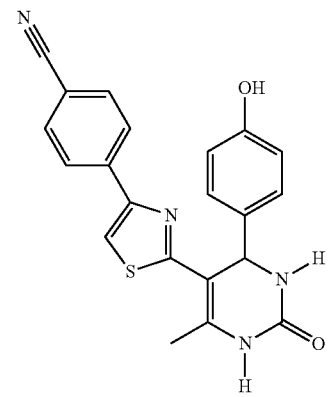
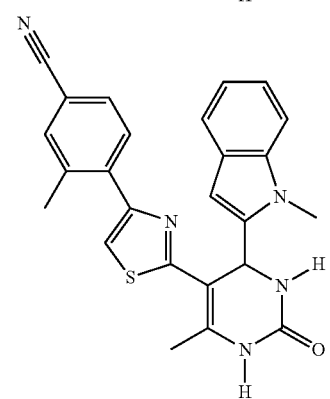
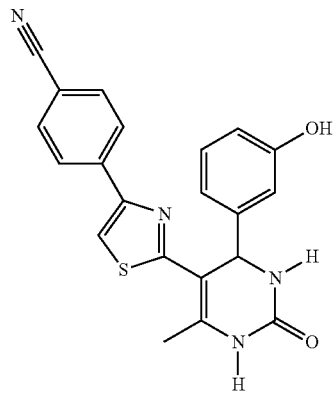
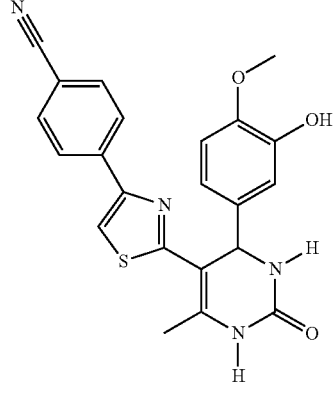
-continued
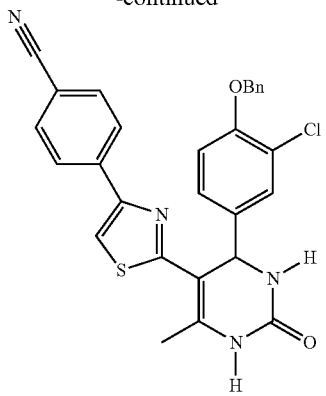
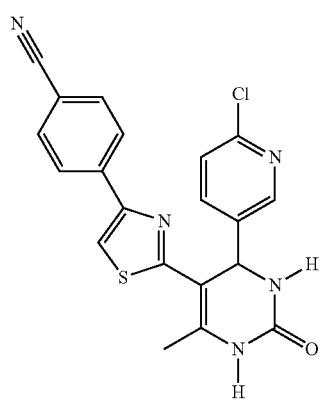
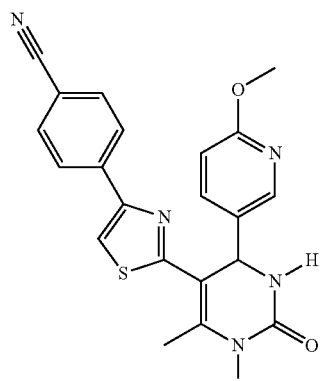
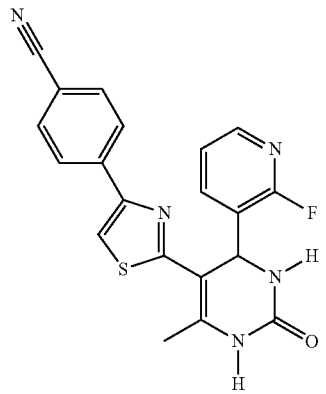

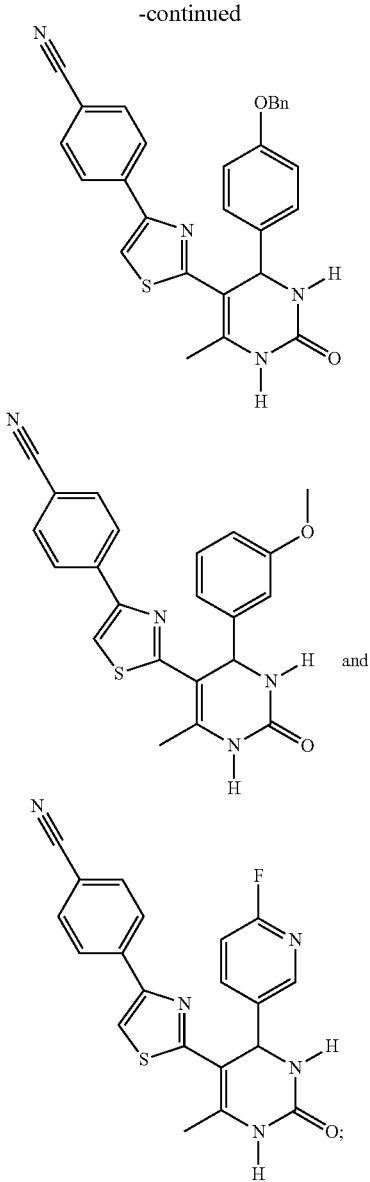

pharmaceutically acceptable salts thereof; solvates thereof and deuterated form thereof.

Embodiment 13

A composition comprising a compound according to any one of Embodiment 1-12, pharmaceutically acceptable salt thereof or solvate thereof and pharmaceutically acceptable carrier.

Embodiment 14

A composition comprising a compound according to any one of Embodiments 1-12, pharmaceutically acceptable salt thereof or solvate thereof and another therapeutic agent.

Embodiment 15

A composition according to Embodiment 14, wherein said therapeutic agent is selected from the group consisting of NRTIs, NNRTIs, protease inhibitors, integrase inhibitors, and CCR5 antagonists.

Embodiment 16

A composition according to Embodiment 14, wherein said therapeutic agent is tenofovir.

Embodiment 17

A method for inhibiting HIV-1 replication in patients by administering an effective HIV-1 replication inhibiting amount of a compound according to any one of Embodiments 1-12, pharmaceutically acceptable salt thereof or solvate thereof to a subject in need thereof or a composition according to any one of Embodiments 13-16.

Embodiment 18

The method according to Embodiment 17, which comprises inhibiting the viral RT enzyme.

Embodiment 19

The method according to Embodiment 17, which comprises inhibiting HIV strains resistant to NNRTIs.

Embodiment 20

A method for treating patients infected with HIV/AIDS, by administering a compound according to any one of Embodiments 1-12, pharmaceutically acceptable salt thereof or solvate thereof to a subject in need thereof or a composition according to any one of Embodiments 13-16.

Embodiment 21

A pre-exposure prophylaxis method for treating a patient and for the prevention of transmission from an infected person to an uninfected person by administering to a patient in need thereof a therapeutically effective amount of a compound of according to any one of Embodiments 1-12, pharmaceutically acceptable salt thereof or solvate thereof to a subject in need thereof or a composition according to any one of Embodiments 13-16.

The compounds of the present disclosure can be administered by any conventional means available for use in conjunction with pharmaceuticals, either as individual therapeutic agents or in a combination of therapeutic agents. They can be administered alone, but generally administered with a pharmaceutical carrier selected on the basis of the chosen route of administration and standard pharmaceutical practice. The compounds can also be administered in conjunction with other therapeutic agents, such as with existing standard of care treatments (NRTIs, NNRTIs, protease inhibitors, integrase inhibitors, CCR5 antagonists and the like), with one particular example being Tenofovir.

The pharmaceutically acceptable carriers described herein, for example, vehicles, adjuvants, excipients, or diluents, are well-known to those who are skilled in the art. Typically, the pharmaceutically acceptable carrier is chemically inert to the active compounds and has no detrimental side effects or toxicity under the conditions of use. The pharmaceutically acceptable carriers can include polymers and polymer matrices.

The dosage administered will, of course, vary depending upon known factors, such as the pharmacodynamics characteristics of the particular agent and its mode and route of administration; the age, health and weight of the recipient; the nature and extent of the symptoms; the kind of concurrent treatment; the frequency of treatment; and the effect desired. A daily dosage of active ingredient can be expected to be about 0.001 to 1000 milligrams (mg) per kilogram (kg) of body weight, with the preferred dose being 0.1 to about 30 mg/kg.

Dosage forms (compositions suitable for administration) typically contain from about 1 mg to about 500 mg of active ingredient per unit. In these pharmaceutical compositions, the active ingredient will ordinarily be present in an amount of about 0.5-95% weight based on the total weight of the composition.

The active ingredient can be administered orally in solid dosage forms, such as capsules, tablets, and powders, or in liquid dosage forms, such as elixirs, syrups and suspensions. It can also be administered parenterally, in sterile liquid dosage forms. Other dosage forms are potentially possible such as administration transdermally, via patch mechanism or ointment.

Formulations suitable for oral administration can comprise (a) liquid solutions, such as an effective amount of the compound dissolved in diluents, such as water, saline, or orange juice; (b) capsules, sachets, tablets, lozenges, and troches, each containing a predetermined amount of the active ingredient, as solids or granules; (c) powders; (d) suspensions in an appropriate liquid; and (e) suitable emulsions. Liquid formulations may include diluents, such as water and alcohols, for example, ethanol, benzyl alcohol, propylene glycol, glycerin, and the polyethylene alcohols, either with or without the addition of a pharmaceutically acceptable surfactant, suspending agent, or emulsifying agent. Capsule forms can be of the ordinary hard- or soft-shelled gelatin type containing, for example, surfactants, lubricants, and inert fillers, such as lactose, sucrose, calcium phosphate, and corn starch. Tablet forms can include one or more of the following: lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible carriers. Lozenge forms can comprise the active ingredient in a flavor, usually sucrose and acacia or tragacanth, as well as pastilles comprising the active ingredient in an inert base, such as gelatin and glycerin, or sucrose and acadia, emulsions, and gels containing, in addition to the active ingredient, such carriers as are known in the art; and mouthwashes.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The compound can be administered in a physiologically acceptable diluent in a pharmaceutical carrier, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol such as poly(ethyleneglycol) 400, glycerol ketals, such as 2,2-dimethyl-1,3-dioxolane-4-methanol, ethers, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils, which can be used in parenteral formulations include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters. Suitable soaps for use in parenteral formulations include fatty alkali metal, ammonium, and triethanolamine salts, and suitable detergents include (a) cationic detergents such as, for example, dimethyldialkylammonium halides, and alkylpyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylene polypropylene copolymers, (d) amphoteric detergents such as, for example, alkyl β-aminopropionates, and 2-alkylimidazoline quaternary ammonium salts, and (e) mixtures thereof.

The parenteral formulations typically contain from about 0.5% to about 25% by weight of the active ingredient in solution. Suitable preservatives and buffers can be used in such formulations. In order to minimize or eliminate irritation at the site of injection, such compositions may contain one or more nonionic surfactants having a hydrophile-lipophile balance (HLB) of from about 12 to about 17. The quantity of surfactant in such formulations ranges from about 5% to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol.

Formulations for topical administration include those pharmaceutical forms in which the compound is applied externally by direct contact with the skin surface to be treated. Conventional pharmaceutical forms for this purpose include ointments, lotions, pastes, jellies, sprays, aerosols, and the like. The term "ointment" embraces formulations (including creams) having oleaginous, absorption, water-soluble and emulsion-type bases, e.g., petrolatum, lanolin, polyethylene glycols, as well as mixtures of these. These compositions may also be dissolved in conventional solvents such as dimethylsulfoxide (DMSO), acetonitrile, dimethylformamide (DMF), dimethylacetamide (DMA), and propylene glycol/ethanol/water.

Pharmaceutically acceptable excipients are also well-known to those who are skilled in the art. The choice of excipient will be determined in part by the particular compound, as well as by the particular method used to administer the composition. Accordingly, there is a wide variety of suitable formulations of the pharmaceutical composition of the present disclosure. The following methods and excipients are merely exemplary and are in no way limiting. The pharmaceutically acceptable excipients preferably do not interfere with the action of the active ingredients and do not cause adverse side-effects. Suitable carriers and excipients include solvents such as water, alcohol, and propylene glycol, solid absorbants and diluents, surface active agents, suspending agent, tableting binders, lubricants, flavors, and coloring agents.

The formulations can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets. The requirements for effective pharmaceutical carriers for injectable compositions are well known to those of ordinary skill in the art. See *Pharmaceutics and Pharmacy Practice*, J.B. Lippincott Co., Philadelphia, Pa., Banker and Chalmers, Eds., 238-250 (1982) and *ASHP Handbook on Injectable Drugs*, Toissel, 4th ed., 622-630 (1986).

Additionally, formulations suitable for rectal administration may be presented as suppositories by mixing with a variety of bases such as emulsifying bases or water-soluble bases. Formulations suitable for vaginal administration may be presented as pessaries, tampons, creams, gels, pastes, foams such as spermicidal foams, or spray formulas containing, in addition to the active ingredient, such carriers as are known in the art to be appropriate.

Suitable pharmaceutical carriers are described in Remington's Pharmaceutical Sciences, Mack Publishing Company, a standard reference text in this field.

The dose administered to an animal, particularly a human, in the context of the present disclosure should be sufficient to affect a therapeutic response in the animal over a reasonable time frame. One skilled in the art will recognize that dosage will depend upon a variety of factors including a condition of the animal, the body weight of the animal, as well as the severity and stage of the condition being treated.

A suitable dose is that which will result in a concentration of the active agent in a patient which is known to affect the desired response. The preferred dosage is the amount which results in maximum inhibition of the condition being treated, without unmanageable side effects.

The size of the dose also will be determined by the route, timing and frequency of administration as well as the existence, nature, and extend of any adverse side effects that might accompany the administration of the compound and the desired physiological effect.

Useful pharmaceutical dosage forms for administration of the compounds according to the present disclosure can be illustrated as follows:

Hard Shell Capsules

A large number of unit capsules are prepared by filling standard two-piece hard gelatine capsules each with 100 mg of powdered active ingredient, 150 mg of lactose, 50 mg of cellulose and 6 mg of magnesium stearate.

Soft Gelatin Capsules

A mixture of active ingredient in a digestible oil such as soybean oil, cottonseed oil or olive oil is prepared and injected by means of a positive displacement pump into molten gelatin to form soft gelatin capsules containing 100 mg of the active ingredient. The capsules are washed and dried. The active ingredient can be dissolved in a mixture of polyethylene glycol, glycerin and sorbitol to prepare a water miscible medicine mix.

Tablets

A large number of tablets are prepared by conventional procedures so that the dosage unit was 100 mg of active ingredient, 0.2 mg. of colloidal silicon dioxide, 5 mg of magnesium stearate, 275 mg of microcrystalline cellulose, 11 mg. of starch, and 98.8 mg of lactose. Appropriate aqueous and non-aqueous coatings may be applied to increase palatability, improve elegance and stability or delay absorption.

Immediate Release Tablets/Capsules

These are solid oral dosage forms made by conventional and novel processes. These units are taken orally without water for immediate dissolution and delivery of the medication. The active ingredient is mixed in a liquid containing ingredient such as sugar, gelatin, pectin and sweeteners. These liquids are solidified into solid tablets or caplets by freeze drying and solid state extraction techniques. The drug compounds may be compressed with viscoelastic and thermoelastic sugars and polymers or effervescent components to produce porous matrices intended for immediate release, without the need of water.

Moreover, the compounds of the present disclosure can be administered in the form of nose drops, or metered dose and a nasal or buccal inhaler. The drug is delivered from a nasal solution as a fine mist or from a powder as an aerosol.

The term "comprising" (and its grammatical variations) as used herein is used in the inclusive sense of "having" or "including" and not in the exclusive sense of "consisting only of." The terms "a" and "the" as used herein are understood to encompass the plural as well as the singular.

All publications, patents and patent applications cited in this specification are herein incorporated by reference, and for any and all purpose, as if each individual publication, patent or patent application were specifically and individually indicated to be incorporated by reference. In the case of inconsistencies, the present disclosure will prevail.

The foregoing description of the disclosure illustrates and describes the present disclosure. Additionally, the disclosure shows and describes only the preferred embodiments but, as mentioned above, it is to be understood that the disclosure is capable of use in various other combinations, modifications, and environments and is capable of changes or modifications within the scope of the concept as expressed herein, commensurate with the above teachings and/or the skill or knowledge of the relevant art.

The embodiments described herein above are further intended to explain best modes known of practicing it and to enable others skilled in the art to utilize the disclosure in such, or other, embodiments and with the various modifications required by the particular applications or uses. Accordingly, the description is not intended to limit it to the form disclosed herein. Also, it is intended that the appended claims be construed to include alternative embodiments.

REFERENCES

1. Global report: UNAIDS report on the global AIDS epidemic 2010: Joint United Nations Programme on HIV/AIDS (UNAIDS); 2010 2010.
2. Interim guidance: preexposure prophylaxis for the prevention of HIV infection in men who have sex with men. MMWR Morb Mortal Wkly Rep 2011; 60:65-8.
3. Grosskurth H, Mosha F, Todd J, et al. Impact of improved treatment of sexually transmitted diseases on HIV infection in rural Tanzania: randomised controlled trial. Lancet 1995; 346:530-6.
4. Grant R M, Lama J R, Anderson P L, et al. Preexposure chemoprophylaxis for HIV prevention in men who have sex with men. N Engl J Med 2010; 363:2587-99.
5. Chasela C S, Hudgens M G, Jamieson D J, et al. Maternal or infant antiretroviral drugs to reduce HIV-1 transmission. N Engl J Med 2010; 362:2271-81.
6. Achievements in public health. Reduction in perinatal transmission of HIV infection—United States, 1985-2005. MMWR Morb Mortal Wkly Rep 2006; 55:592-7.
7. MacArthur R D, Novak R M, Peng G, et al. A comparison of three highly active antiretroviral treatment strategies consisting of non-nucleoside reverse transcriptase inhibitors, protease inhibitors, or both in the presence of nucleoside reverse transcriptase inhibitors as initial therapy (CPCRA 058 FIRST Study): a long-term randomised trial. Lancet 2006; 368:2125-35.

8. Oversteegen L, Shah M, Rovini H. HIV combination products. Nat Rev Drug Discov 2007; 6:951-2.
9. Hammer S M, Eron J J, Jr., Reiss P, et al. Antiretroviral treatment of adult HIV infection: 2008 recommendations of the International AIDS Society-USA panel. JAMA 2008; 300:555-70.
10. Thompson M A, Aberg J A, Cahn P, et al. Antiretroviral treatment of adult HIV infection: 2010 recommendations of the International AIDS Society-USA panel. JAMA 2010; 304:321-33.
11. Johnson V A, Brun-Vezinet F, Clotet B, et al. Update of the drug resistance mutations in HIV-1: December 2010. Top HIV Med 2010; 18:156-63.
12. Kim, J.; Cechetto, J.; No, Z.; Christophe, T.; Kim, T.; Taehee, N.; Nam, J. Y.; So, W.; Jo, M.; Ok, T.; Park, C.; Seo, M. J.; Sohn, J.- H.; Sommer, P.; Boese, A. S.; Han, S.- J.; Park, Y. S.; Kim, H. P. WO 2010046780, 2010.
13. Kharchenko, J. V.; Detistov, O. S.; Orlov, V. D. *J. Comb. Chem.* 2009, 11, 216-219.
14. Pagano, N. Herath, A., Cosford, N. D. P. *J. Flow Chem.* 2011, 1, 1-4.
15. For similar reaction conditions, see: Zamir, L. O.; Nguyen, C. *J. Labelled Compd. Radiopharm.* 1988, 25, 1189-1196. For characterization data, see: Paquette, L. A.; Efremov, I. *J. Am. Chem. Soc.* 2001, 123, 4492-4501.

What is claimed is:

1. A compound represented by the following Formula I:

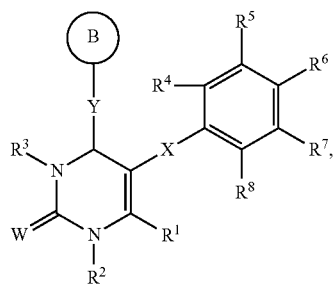

I wherein B is selected from the group consisting of substituted or unsubstituted heteroaryl;
W is O, S, or NR;
Y is a linker moiety selected from the group consisting of a direct bond, O, S, NR, $C_1$-$C_8$ alkyl, $C_2$-$C_8$ alkenyl, $C_2$-$C_8$ alkynyl, $C_1$-$C_8$ alkoxy, $C_1$-$C_8$ thioalkyl, $C_1$-$C_8$ alkylNR;
R, $R^1$, $R^2$, and $R^3$ are each individually selected from the group consisting of H, $C_1$-$C_8$ alkyl, $C_1$-$C_8$ haloalkyl, $C_1$-$C_8$ alkylaryl, $C_{2-8}$ alkenyl, $C_{2-8}$ alkynyl, cycloalkyl, substituted or unsubstituted aryl, substituted or unsubstituted heteroaryl, or heterocycle;
X is

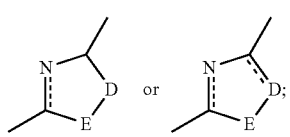

D and E are each individually selected from the group consisting of O, S, $NR^9$, CR or $CR^1R^2$;
$R^9$ is selected from the group consisting of H, $C_1$-$C_8$ alkyl, $C_1$-$C_8$ haloalkyl, $C_3$-$C_8$ cycloalkyl, $C_2$-$C_8$ alkenyl, $C_2$-$C_8$ alkynyl, $C_5$-$C_{10}$ aryl, $C_5$-$C_{10}$ heterocycle each of which is optionally substituted with halogen, —$OR^{10}$, —$NR^{11}R^{12}$, —$SR^{11}$, —$S(O)R^{11}$, —$S(O)_2R^{12}$, or —$S(O)R^{11}R^{12}$;
$R^4$, $R^5$, $R^6$, $R^7$, and $R^8$ are each are independently selected from H, hydroxyl, halogen, cyano, $NO_2$, —$OR^{10}$, —$SR^{11}$, —$S(O)R^{11}$, —$S(O)_2R^{12}$, —$S(O)_2NR^{11}R^{12}$, $C_1$-$C_8$ haloalkyl, $COR^{13}$, —$C(O)OR^{12}$, —$C(O)NR^{11}R^{12}$, —$C(O)R^{12}$, —$NR^{11}R^{12}$, —$NR^{11}C(O)R^{12}$, —$NR^{11}S(O)_2R^{12}$, —$NR^{11}C(O)OR^{12}$, —$B(OH)_2$, $C_1$-$C_8$ alkyl, $C_3$-$C_8$ cycloalkyl, $C_2$-$C_8$ alkenyl, $C_2$-$C_8$ alkynyl, substituted or unsubstituted aryl, substituted or unsubstituted heteroaryl, -alkylC(O)—$OR^{12}$, -alkylC(O)$NR^{11}R^{12}$, -alkenylC(O)$OR^{12}$, -alkenylC(O)$NR^{11}R^{12}$, -aryl$(CH_2)_mC(O)OR^{12}$, -aryl$(CH_2)_mC(O)NR^{11}R^{12}$, —$(CH_2)_mC(O)NR^{11}S(O)_2R^{12}$, -aryl$(CH_2)_m$—$C(O)NR^{11}S(O)_2R^{12}$, —$(CH_2)_mS(O)_2NR^{11}C(O)R^{12}$, -aryl$(CH_2)_mS(O)_2NR^{11}C(O)R^{12}$, or substituted or unsubstituted heterocycle or substituted or unsubstituted heteroaryl containing 1 to 4 heteroatoms, optionally substituted with 1 to 2 substituents selected from the group consisting of H, hydroxyl, halogen, $CF_3$, $C_1$-$C_8$ alkyl, $C_1$-$C_8$ alkoxy, cyano, amino, $C_1$-$C_8$ alkylamino, and $C_1$-$C_8$ alkoxy$C_1$-$C_8$ alkylamino provided at least one of $R^4$, $R^5$, $R^6$, $R^7$, or $R^8$ is other than hydrogen;
$R^{10}$, $R^{11}$, $R^{12}$, and $R^{13}$ are each individually selected from the group consisting of H, $C_1$-$C_8$ alkyl, $C_1$-$C_8$ haloalkyl, $C_1$-$C_8$ alkylaryl, $C_{2-8}$ alkenyl, $C_{2-8}$ alkynyl, cycloalkyl, substituted or unsubstituted aryl, substituted or unsubstituted heteroaryl, or heterocycle;
m=0 to 6;
wherein alkyl, alkenyl, alkynyl, cycloalkyl, aryl, heteroaryl or heterocycle may be substituted or unsubstituted;
pharmaceutically acceptable salt thereof; solvate thereof and deuterated form thereof.

2. A compound according to claim 1, wherein Y is a direct bond.

3. A compound according to claim 1, wherein W is O.

4. A compound according to claim 1, wherein X is

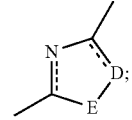

D is CH and E is S.

5. A compound according to claim 1, wherein $R^6$ is selected from the group consisting of CN, $NO_2$, $C_1$-$C_6$ alkyl, aryloxy and halo; each of $R^4$ and $R^8$ is independently H or a $C_1$-$C_6$ alkyl; and each of $R^5$ and $R^7$ is H.

6. A compound being represented by the formula II

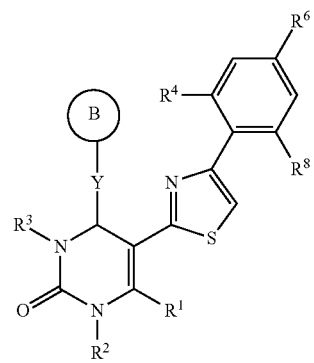

II wherein B is selected from the group consisting of substituted or unsubstituted pyridinyl and when substituted the substitution is halo or $C_1$-$C_6$ alkoxy in the ortho position to the nitrogen in the pyridinyl ring or can be halo in the meta position when the nitrogen is in the 2-position; mono-substituted or unsubstituted quinolinyl and when substituted the substitution is hydroxyl; mono-substituted or unsubstituted indolyl and when substituted the substitution is $C_1$-$C_6$ alkyl; unsubstituted benzothiopheneyl; unsubstituted thiopheneyl; and unsubstituted biphenyl;

Y is a direct bond or Y can be a $C_1$-$C_6$ alkyl when $R^6$ is CN;

$R^1$ is H, $C_1$-$C_6$ alkyl or $C_{3-8}$ cycloalkyl;

$R^2$ is H, $C_1$-$C_6$ alkyl or $C_{3-8}$ cycloalkyl;

$R^3$ is H;

each of $R^4$ and $R^8$ is independently H, $C_1$-$C_6$ alkyl or $C_{3-8}$ cycloalkyl;

$R^6$ is selected from the group consisting of CN, $NO_2$, aryloxy, and halo;

pharmaceutically acceptable salts thereof solvates thereof and deuterated form thereof.

7. A compound represented by the formula III

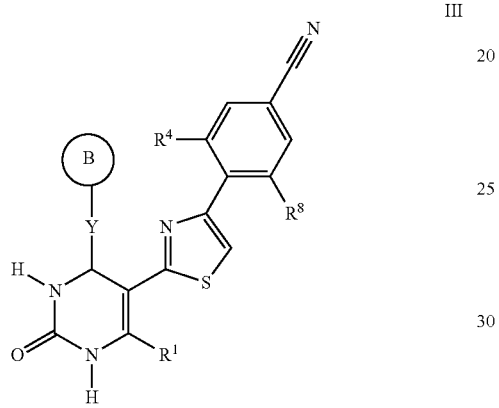

wherein $R^1$ is H, $C_1$-$C_6$ alkyl or $C_{3-8}$ cycloalkyl; $R^4$ and $R^8$ are each independently H, $C_1$-$C_6$ alkyl or $C_{3-8}$ cycloalkyl; Y is a linker moiety selected from the group consisting of a direct bond, O, S, NR $C_1$-$C_8$ alkyl, $C_2$-$C_8$ alkenyl, $C_2$-$C_8$ alkynyl, $C_1$-$C_8$ alkoxy, $C_1$-$C_8$ thioalkyl, $C_1$-$C_8$ alkylNR; and B is selected from the group consisting of phenyl substituted with at least one member selected from the group consisting hydroxyl, halo, $C_1$-$C_6$ alkoxy, aryloxy; pyridyl substituted with at least one member selected from the group consisting halo and $C_1$-$C_6$ alkoxy and indolyl substituted with a $C_1$-$C_6$ alkyl group; pharmaceutically acceptable salts thereof; solvates thereof and deuterated form thereof.

8. A compound being selected from the group consisting of

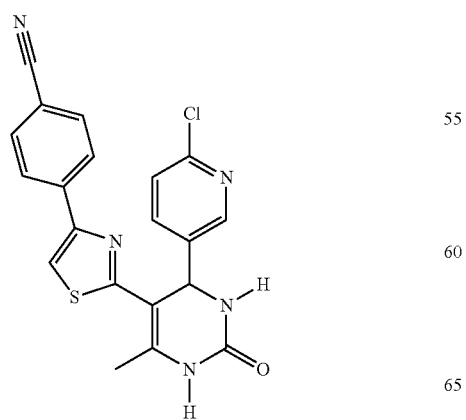

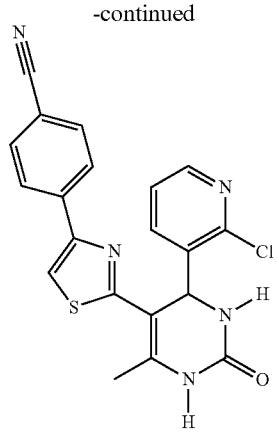

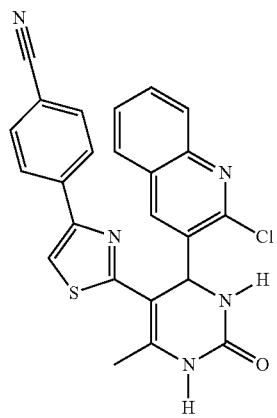

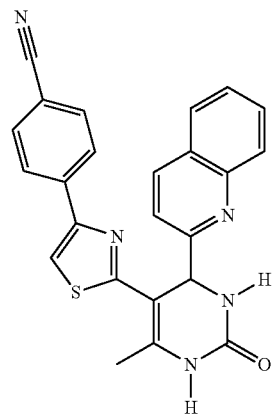

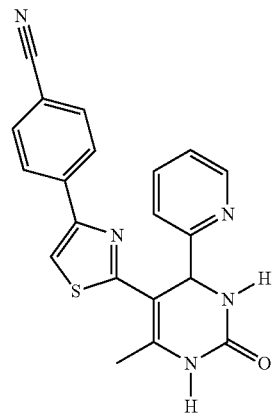

87
-continued
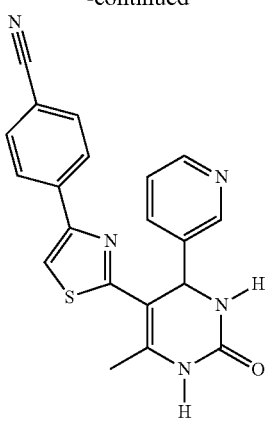
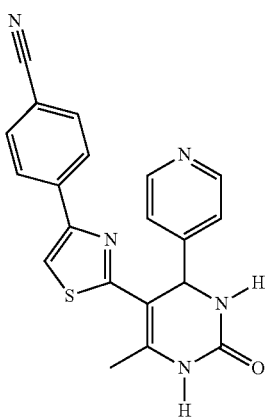
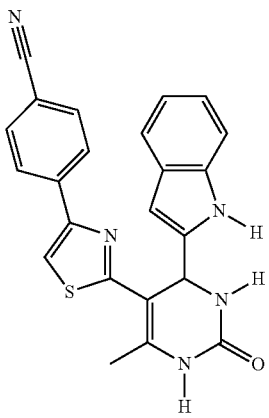
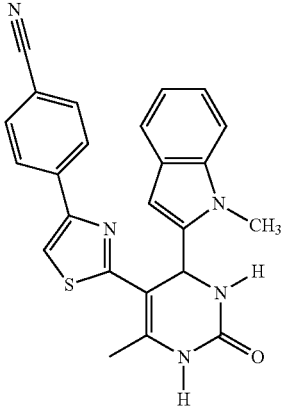
88
-continued
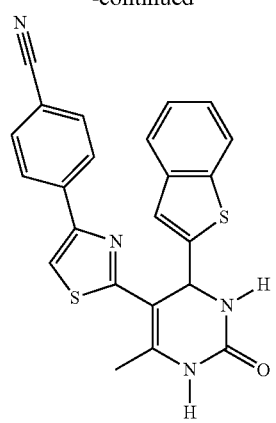
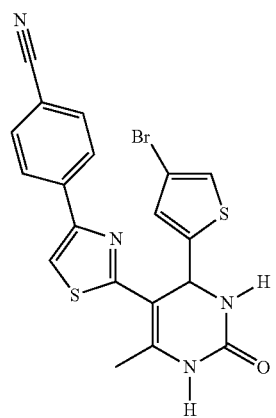
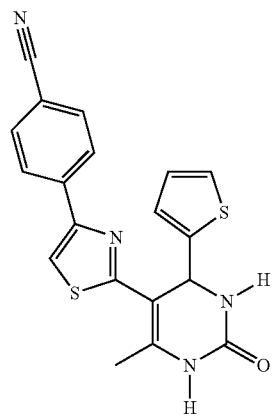
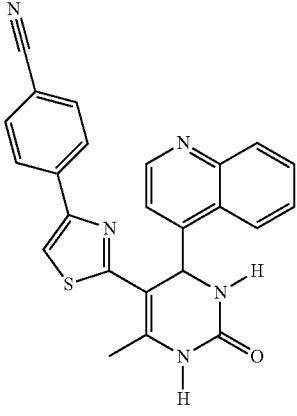

89
-continued
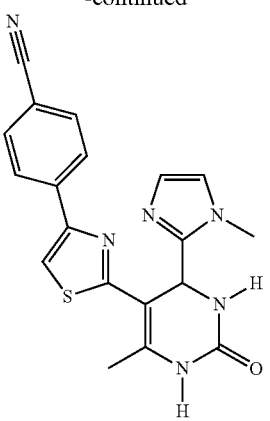
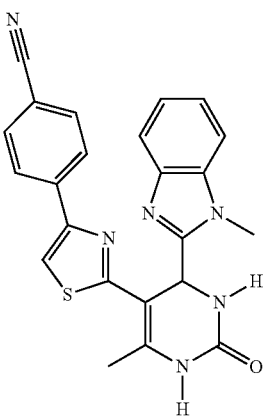
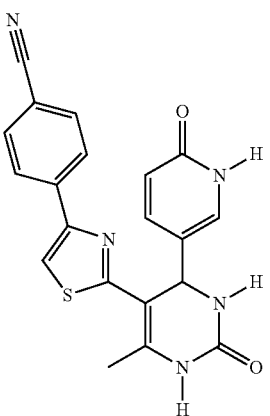
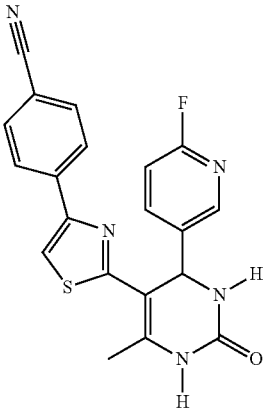
90
-continued
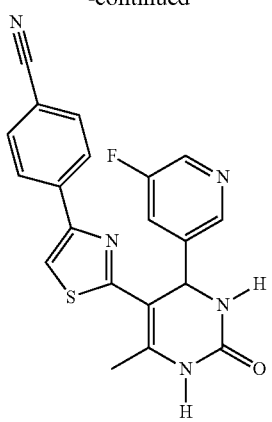
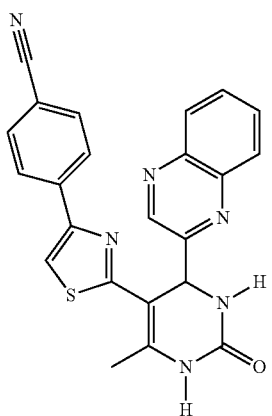
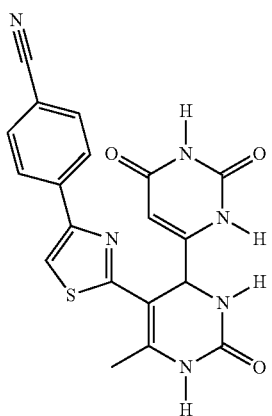
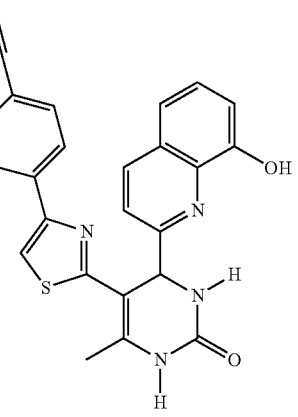

91
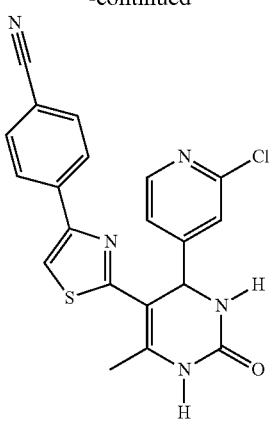
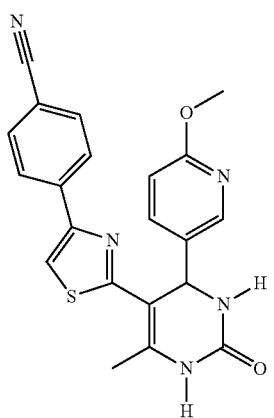
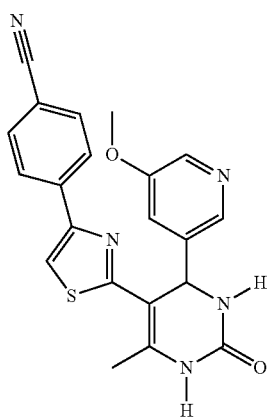
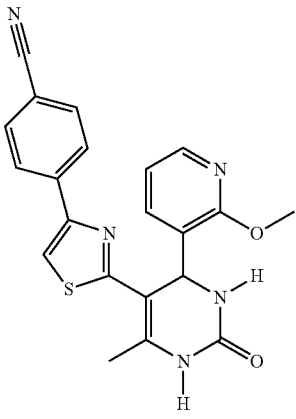
92
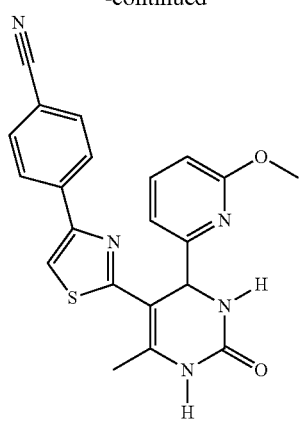
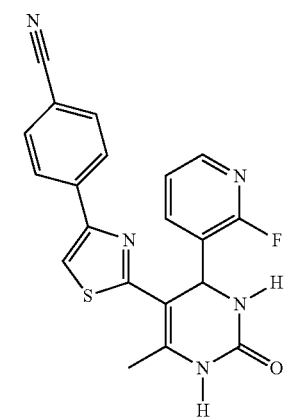
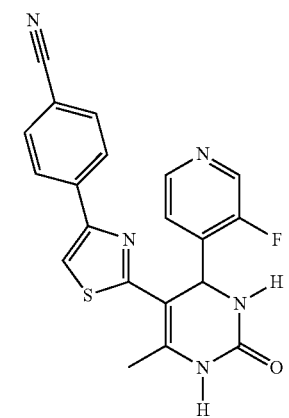
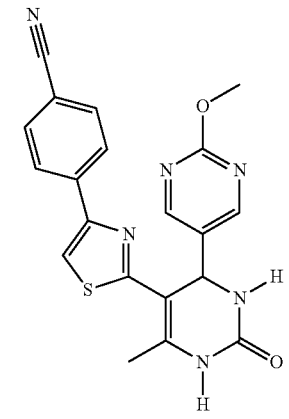

93
-continued
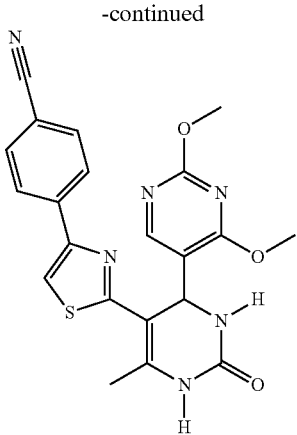
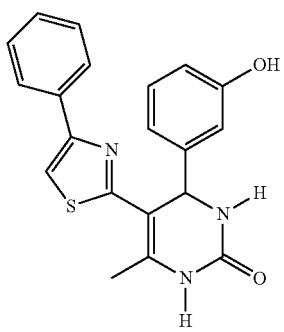
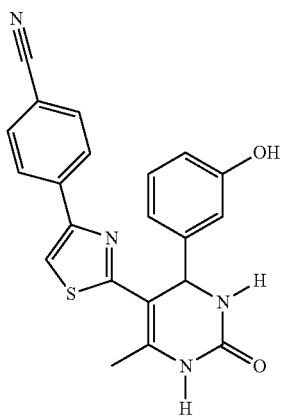
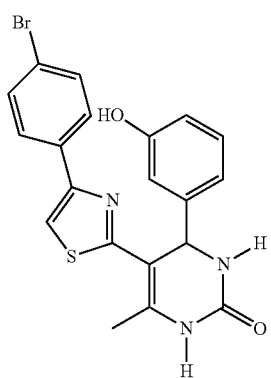
94
-continued
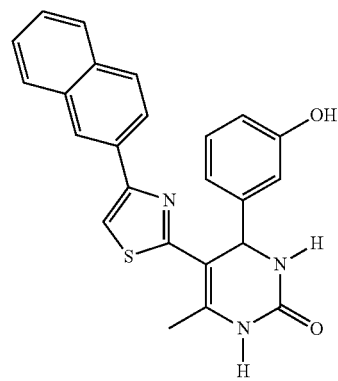
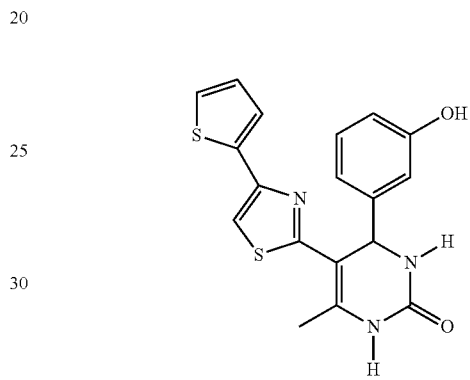
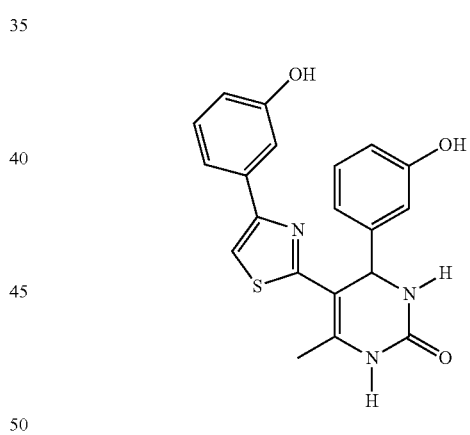
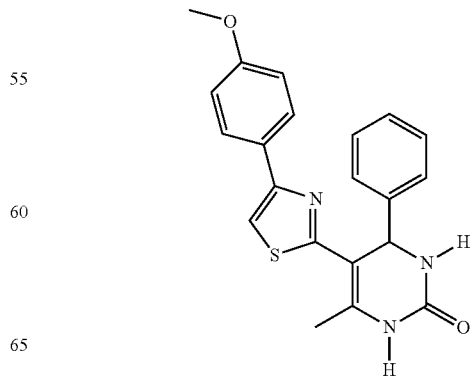

95
-continued
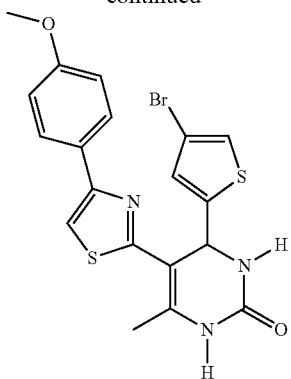
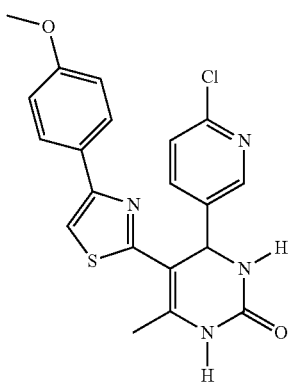
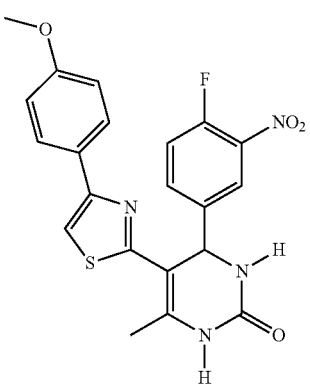
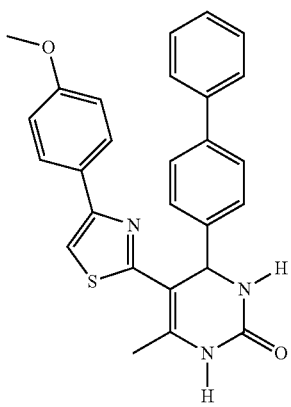
96
-continued
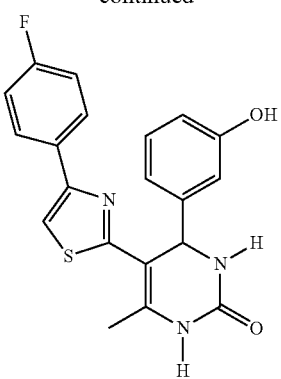
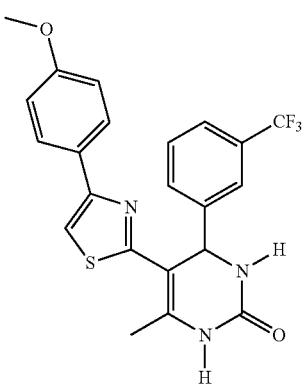
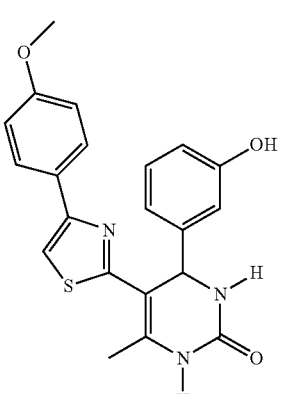
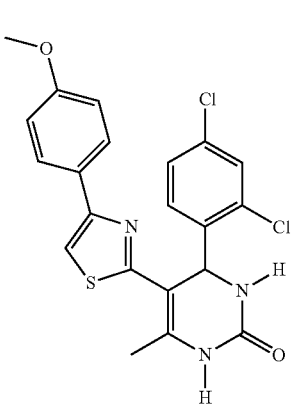

97
-continued
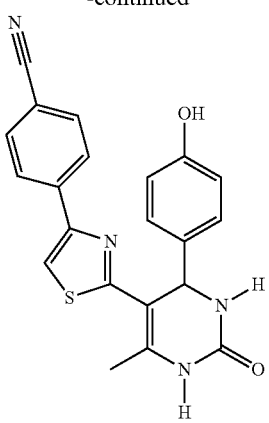
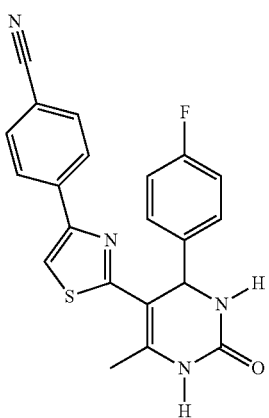
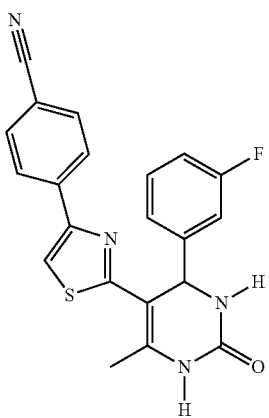
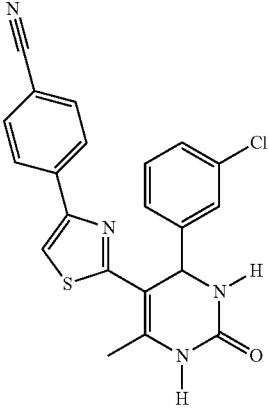
98
-continued
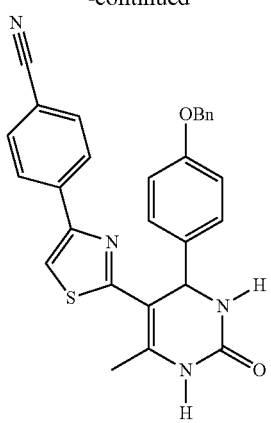
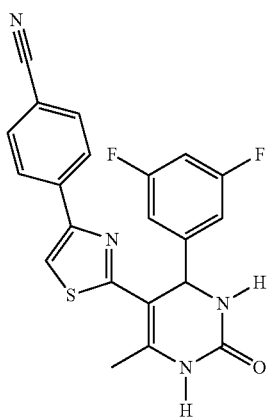
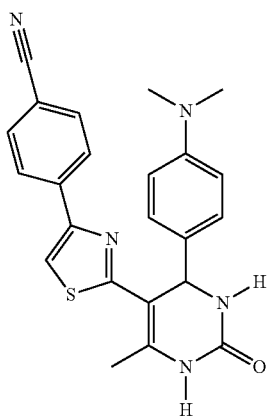
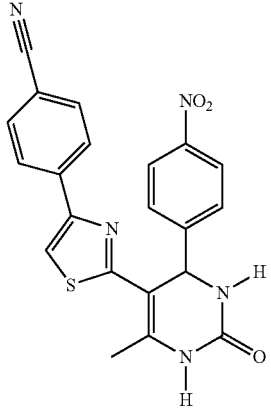

99
-continued
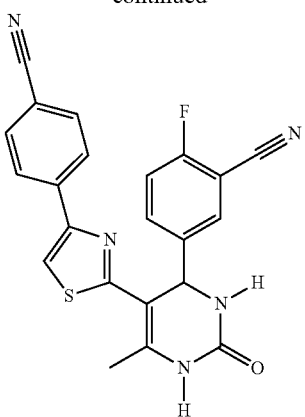
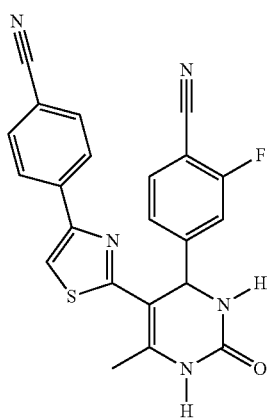
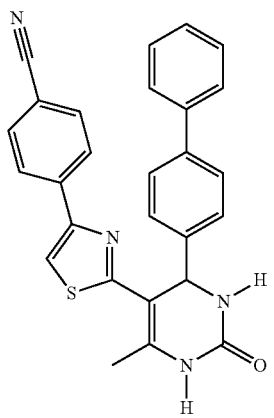
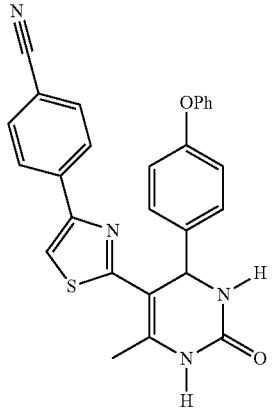
100
-continued
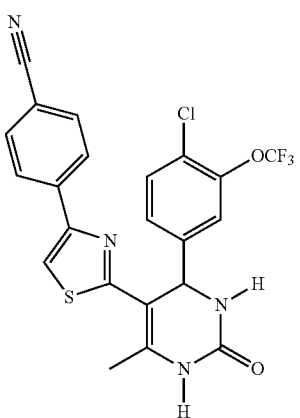
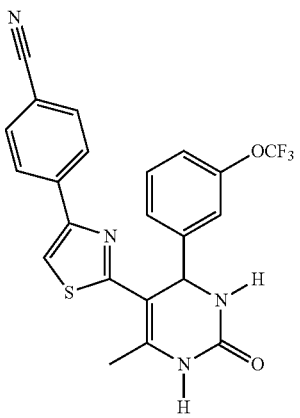
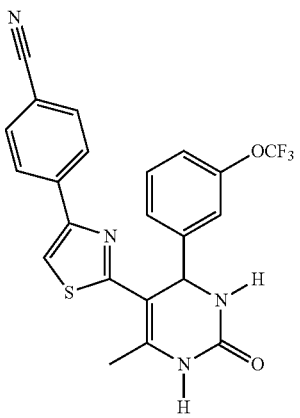
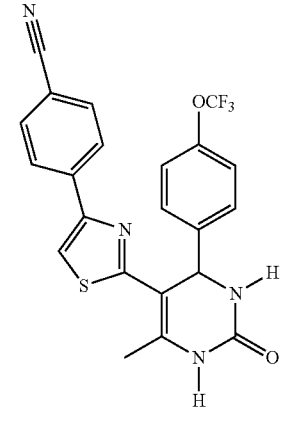

101
-continued
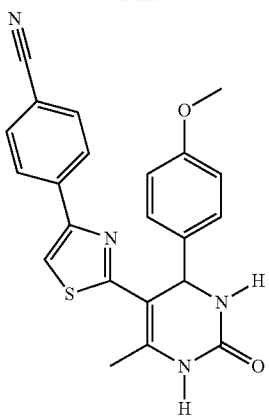
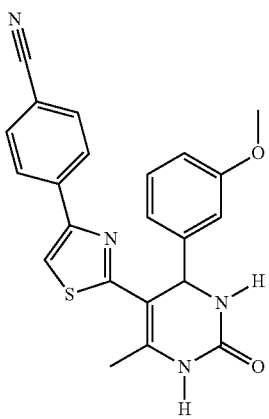
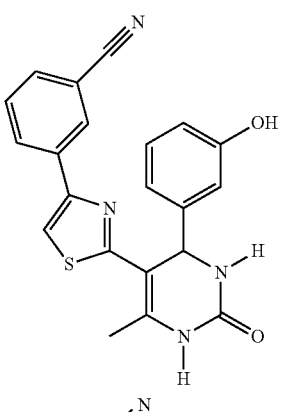
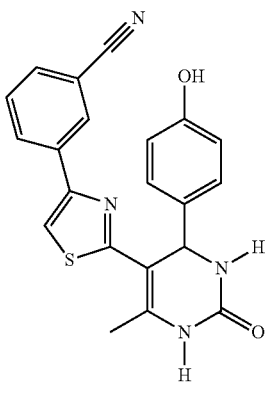
102
-continued
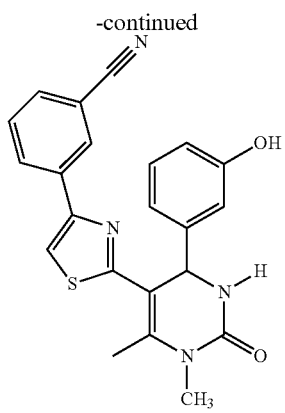
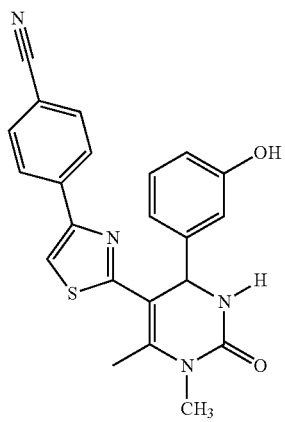
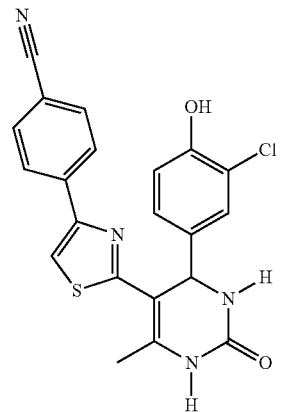
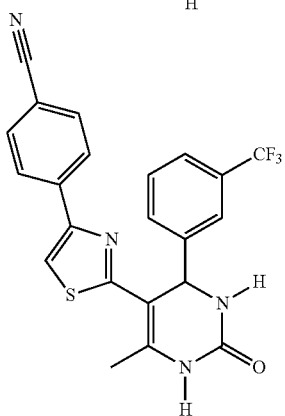

103
-continued
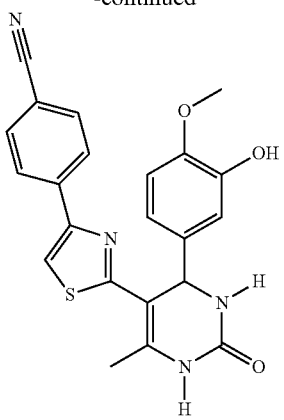
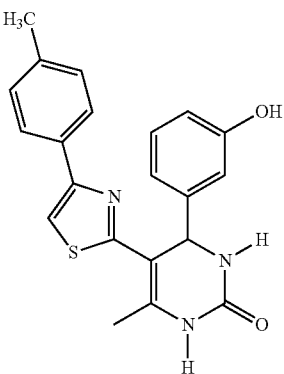
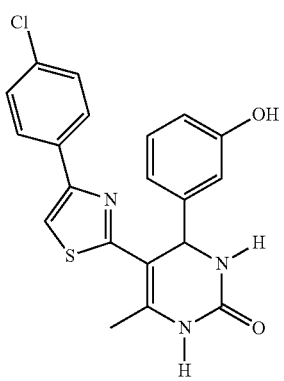
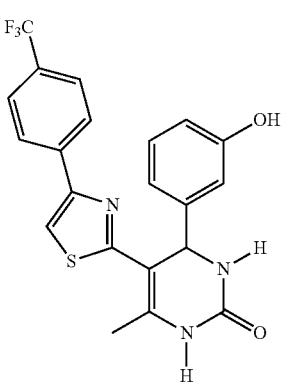
104
-continued
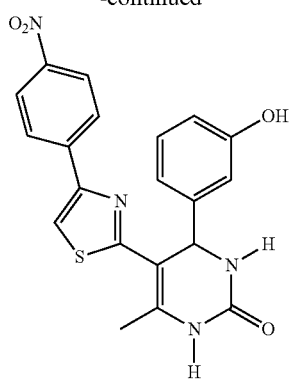
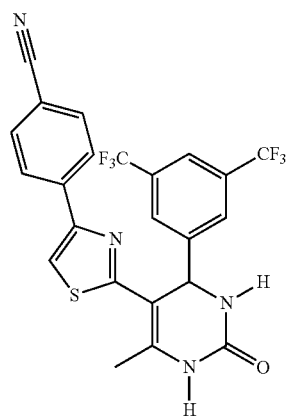
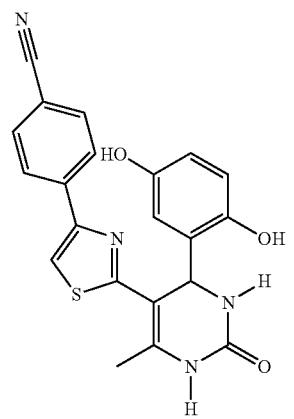
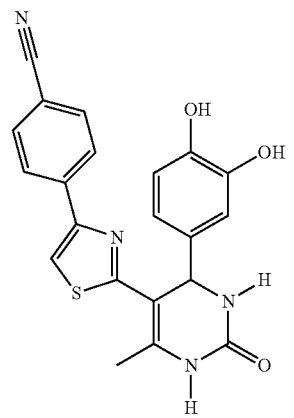

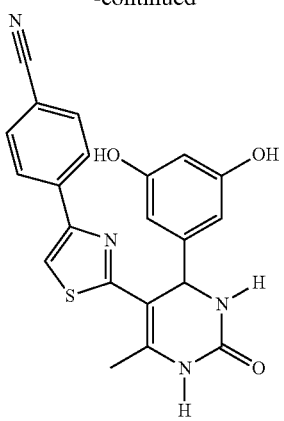
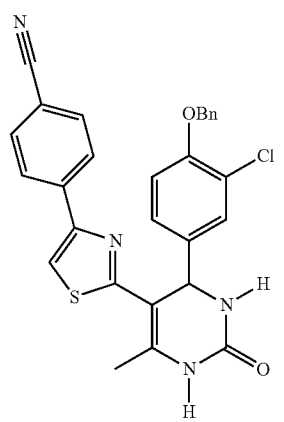 [SMILES: CC1=C(c2nc(-c3ccc(C#N)cc3)cs2)C(c2ccc(OCc3ccccc3)c(Cl)c2)NC(=O)N1]
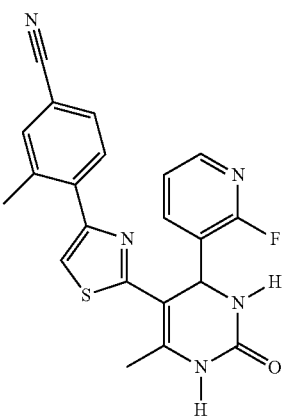 [SMILES: CC1=C(c2nc(-c3ccc(C#N)cc3C)cs2)C(c2cccnc2F)NC(=O)N1]
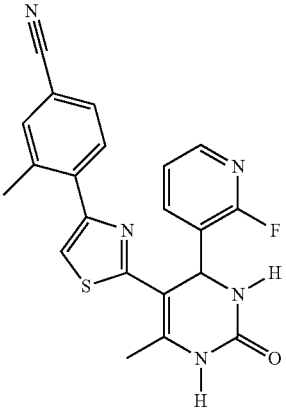 [SMILES: CC1=C(c2nc(-c3ccc(C#N)cc3C)cs2)C(c2cccnc2F)NC(=O)N1]
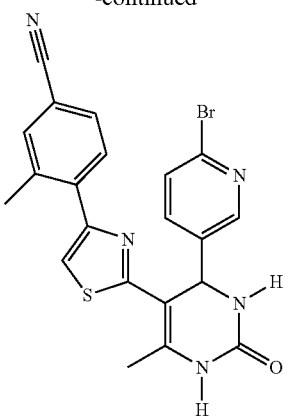
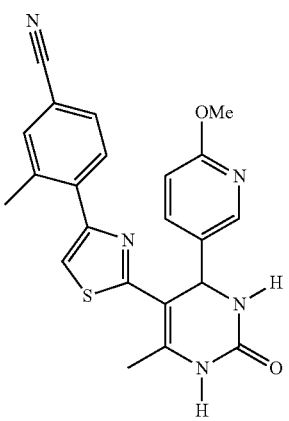 [SMILES: COc1ccc(C2NC(=O)NC(C)=C2c2nc(-c3ccc(C#N)cc3C)cs2)cn1]
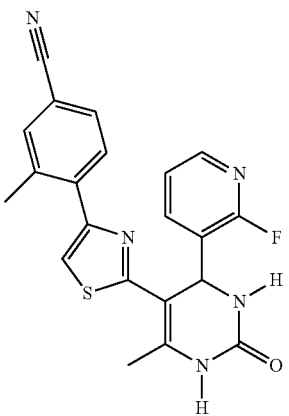 [SMILES: CC1=C(c2nc(-c3ccc(C#N)cc3C)cs2)C(c2cccnc2F)NC(=O)N1]
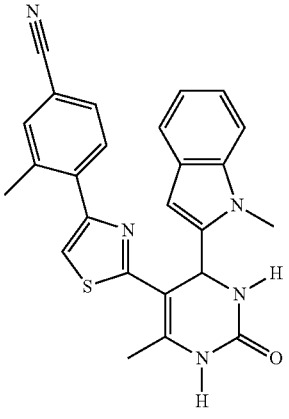

107
-continued
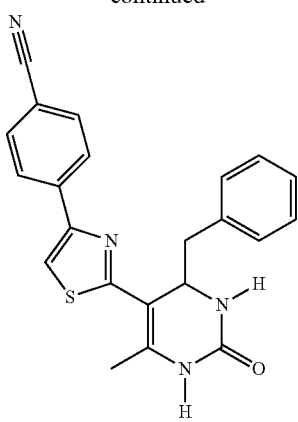
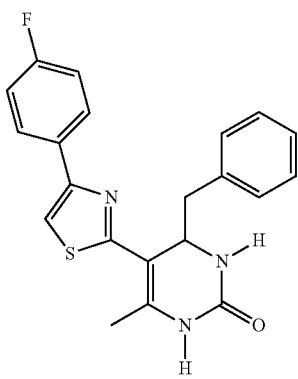 [SMILES: CC1=C(c2nc(-c3ccc(F)cc3)cs2)C(Cc2ccccc2)NC(=O)N1]
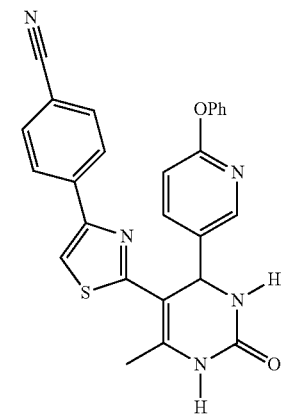 [SMILES: CC1=C(c2nc(-c3ccc(C#N)cc3)cs2)C(c2ccc(Oc3ccccc3)nc2)NC(=O)N1]
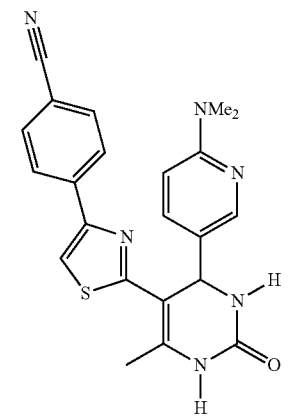 [SMILES: CC1=C(c2nc(-c3ccc(C#N)cc3)cs2)C(c2ccc(N(C)C)nc2)NC(=O)N1]
108
-continued
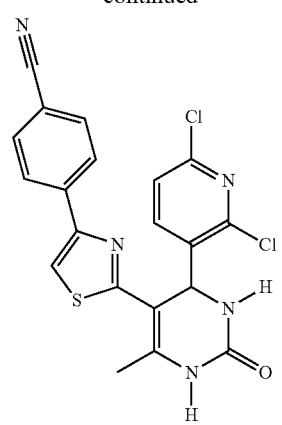
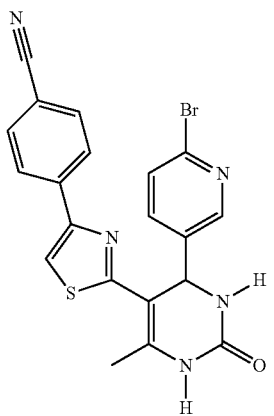 [SMILES: CC1=C(c2nc(-c3ccc(C#N)cc3)cs2)C(c2ccc(Br)nc2)NC(=O)N1]
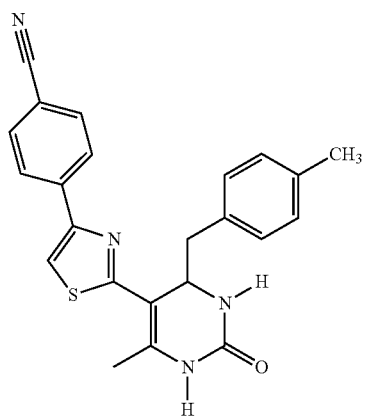 [SMILES: CC1=C(c2nc(-c3ccc(C#N)cc3)cs2)C(Cc2ccc(C)cc2)NC(=O)N1]
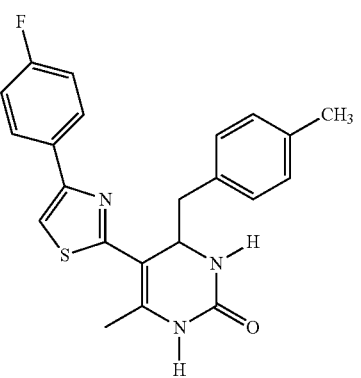 [SMILES: CC1=C(c2nc(-c3ccc(F)cc3)cs2)C(Cc2ccc(C)cc2)NC(=O)N1]
and

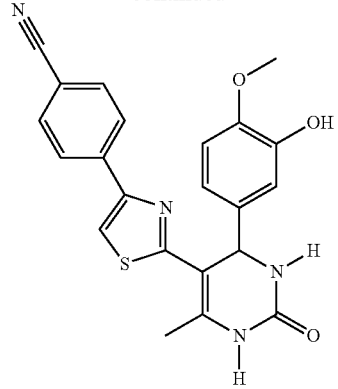
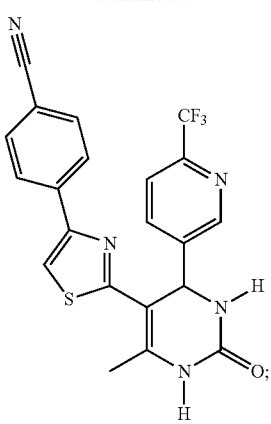 [SMILES: CC1=C(c2nc(-c3ccc(C#N)cc3)cs2)C(c2ccc(C(F)(F)F)nc2)NC(=O)N1]
pharmaceutically acceptable salts thereof solvates thereof and deuterated form thereof.
9. A compound being selected from the group consisting of
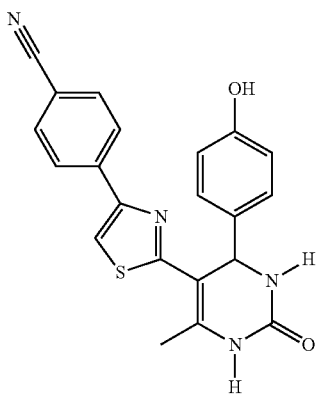
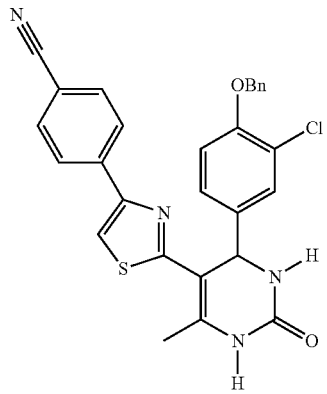
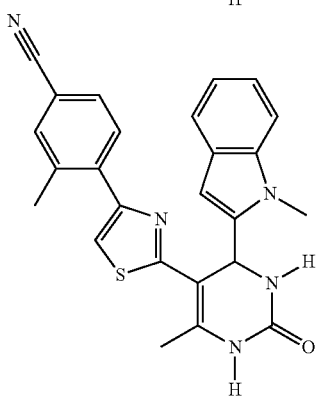
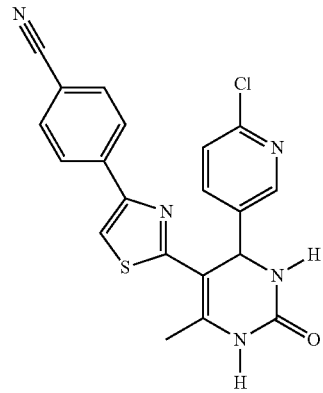
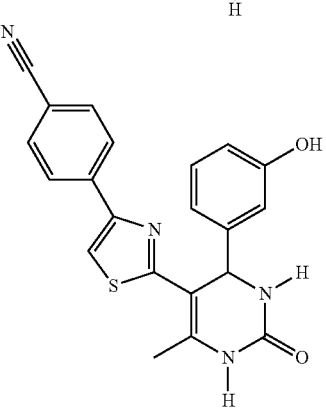
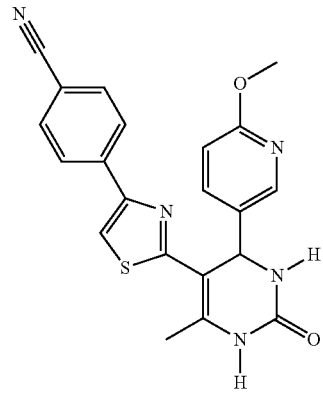

-continued

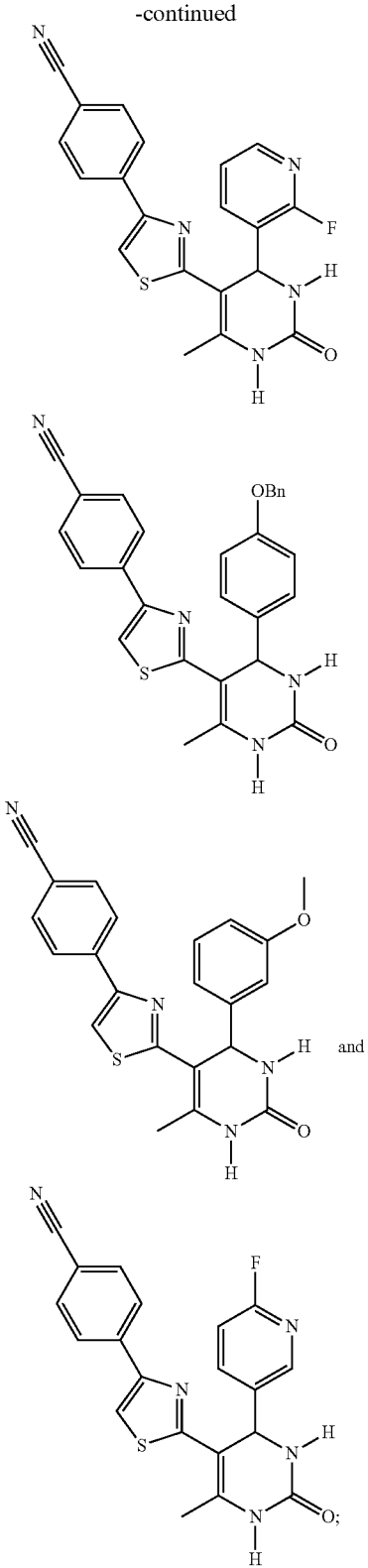

pharmaceutically acceptable salts thereof; solvates thereof and deuterated form thereof.

10. A composition comprising a compound according to claim 1, pharmaceutically acceptable salt thereof or solvate thereof and pharmaceutically acceptable carrier.

11. A composition comprising a compound according to claim 1, pharmaceutically acceptable salt thereof or solvate thereof and another therapeutic agent.

12. A composition according to claim 11, wherein said therapeutic agent is selected from the group consisting of NRTIs, NNRTIs, protease inhibitors, integrase inhibitors, and CCR5 antagonists.

13. A composition according to claim 11, wherein said therapeutic agent is tenofovir.

14. A method for inhibiting HIV-1 replication in a patient by administering an effective HIV-1 replication inhibiting amount of a compound represented by the following Formula I:

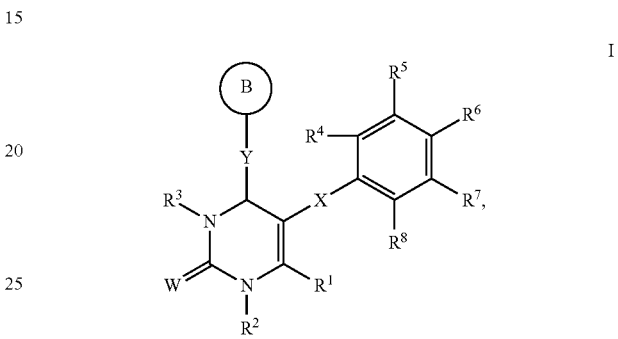

wherein B is selected from the group consisting of substituted or unsubstituted aryl, substituted or unsubstituted heteroaryl;

W is O, S, or NR;

Y is a linker moiety selected from the group consisting of a direct bond, O, S, NR, $C_1$-$C_8$ alkyl, $C_2$-$C_8$ alkenyl, $C_2$-$C_8$ alkynyl, $C_1$-$C_8$ alkoxy, $C_1$-$C_8$ thioalkyl, $C_1$-$C_8$ alkylNR;

R, $R^1$, $R^2$, and $R^3$ are each individually selected from the group consisting of H, $C_1$-$C_8$ alkyl, $C_1$-$C_8$ haloalkyl, $C_1$-$C_8$ alkylaryl, $C_{2-8}$ alkenyl, $C_{2-8}$ alkynyl, cycloalkyl, substituted or unsubstituted aryl, substituted or unsubstituted heteroaryl, or heterocycle;

X is

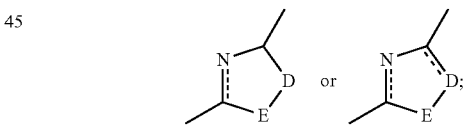

D and E are each individually selected from the group consisting of O, S, $NR^9$, CR or $CR^1R^2$;

$R^9$ is selected from the group consisting of H, $C_1$-$C_8$ alkyl, $C_1$-$C_8$ haloalkyl, $C_3$-$C_8$ cycloalkyl, $C_2$-$C_8$ alkenyl, $C_2$-$C_8$ alkynyl, $C_5$-$C_{10}$ aryl, $C_5$-$C_{10}$ heterocycle each of which is optionally substituted with halogen, —$OR^{10}$, —$NR^{11}R^{12}$, —$SR^{11}$, —$S(O)R^{11}$, —$S(O)_2^{12}$, or —$S(O)_2NR^{11}R^{12}$;

$R^4$, $R^5$, $R^6$, $R^7$, and $R^8$ are each are independently selected from H, hydroxyl, halogen, cyano, $NO_2$, —$OR^{10}$, —$SR^{11}$, —$S(O)R^{11}$, —$S(O)_2R^{12}$, —$S(O)_2NR^{11}R^{12}$, $C_1$-$C_8$ haloalkyl, $COR^{13}$, —$C(O)OR^{12}$, —$C(O)NR^{11}R^{12}$, —$C(O)R^{12}$, —$NR^{11}R^{12}$, —$NR^{11}C(O)R^{12}$, —$NR^{11}S(O)_2R^{12}$, —$NR^{11}C(O)OR^{12}$, —$B(OH)_2$, $C_1$-$C_8$ alkyl, $C_3$-$C_8$ cycloalkyl, $C_2$-$C_8$ alkenyl, $C_2$-$C_8$ alkynyl, substituted or unsubstituted aryl, substituted or unsubstituted heteroaryl, -alkylC(O)—$OR^{12}$, -alkylC (O)NR$^{11}$R$^{12}$, -alkenylC(O)OR$^{12}$, -alkenylC(O)NR$^{11}$R$^{12}$, -aryl(CH$_2$)$_m$C(O)OR$^{12}$, -aryl(CH$_2$)$_m$C(O)NR$^{11}$R$^{12}$, —(CH$_2$)$_m$C(O)NR$^{11}$S(O)$_2$R$^{12}$, -aryl(CH$_2$)$_m$—C(O)NR$^{11}$S(O)$_2$R$^{12}$, —(CH$_2$)$_m$S(O)$_2$NR$^{11}$C(O)R$^{12}$, -aryl(CH$_2$)$_m$S(O)$_2$NR$^{11}$C(O)R$^{12}$, or substituted or unsubstituted heterocycle or substituted or unsubstituted heteroaryl containing 1 to 4 heteroatoms, optionally substituted with 1 to 2 substituents selected from the group consisting of H, hydroxyl, halogen, CF$_3$, C$_1$-C$_8$ alkyl, C$_1$-C$_8$ alkoxy, cyano, amino, C$_1$-C$_8$ alkylamino, and C$_1$-C$_8$ alkoxyC$_1$-C$_8$ alkylamino provided at least one of R$^4$, R$^5$, R$^6$, R$^7$, or R$^8$ is other than hydrogen;

R$^{10}$, R$^{11}$, R$^{12}$, and R$^{13}$ are each individually selected from the group consisting of H, C$_1$-C$_8$ alkyl, C$_1$-C$_8$ haloalkyl, C$_1$-C$_8$ alkylaryl, C$_{2-8}$ alkenyl, C$_{2-8}$ alkynyl, cycloalkyl, substituted or unsubstituted aryl, substituted or unsubstituted heteroaryl, or heterocycle;

m=0 to 6;

wherein alkyl, alkenyl, alkynyl, cycloalkyl, aryl, heteroaryl or heterocycle may be substituted or unsubstituted; pharmaceutically acceptable salt thereof solvate thereof and deuterated form thereof to a subject in need thereof.

15. The method according to claim 14, which comprises inhibiting the viral RT enzyme.

16. The method according to claim 14, which comprises inhibiting HIV strains resistant to NNRTIs.

17. A method for treating patients infected with HIV-1, by administering a therapeutically effective amount of a compound represented by the following Formula I:

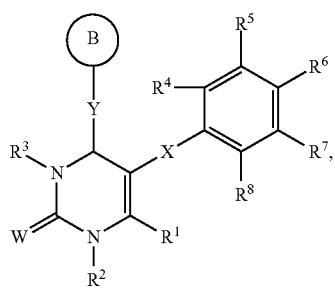

I wherein B is selected from the group consisting of substituted or unsubstituted aryl, substituted or unsubstituted heteroaryl;

W is O, S, or NR;

Y is a linker moiety selected from the group consisting of a direct bond, O, S, NR, C$_1$-C$_8$ alkyl, C$_2$-C$_8$ alkenyl, C$_2$-C$_8$ alkynyl, C$_1$-C$_8$ alkoxy, C$_1$-C$_8$ thioalkyl, C$_1$-C$_8$ alkylNR;

R, R$^1$, R$^2$, and R$^3$ are each individually selected from the group consisting of H, C$_1$-C$_8$ alkyl, C$_1$-C$_8$ haloalkyl, C$_1$-C$_8$ alkylaryl, C$_{2-8}$ alkenyl, C$_{2-8}$ alkynyl, cycloalkyl, substituted or unsubstituted aryl, substituted or unsubstituted heteroaryl, or heterocycle;

X is

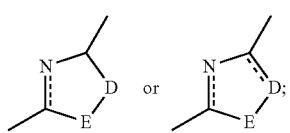

D and E are each individually selected from the group consisting of O, S, NR$^9$, CR or CR$^1$R$^2$;

R$^9$ is selected from the group consisting of H, C$_1$-C$_8$ alkyl, C$_1$-C$_8$ haloalkyl, C$_3$-C$_8$ cycloalkyl, C$_2$-C$_8$ alkenyl, C$_2$-C$_8$ alkynyl, C$_5$-C$_{10}$ aryl, C$_5$-C$_{10}$ heterocycle each of which is optionally substituted with halogen, —OR$^{10}$, —NR$^{11}$R$^{12}$, —SR$^{11}$, —S(O)R$^{11}$, —S(O)$_2$R$^{12}$, or —S(O)$_2$NR$^{11}$R$^{12}$;

R$^4$, R$^5$, R$^6$, R$^7$, and R$^8$ are each are independently selected from H, hydroxyl, halogen, cyano, NO$_2$, —OR$^{10}$, —SR$^{11}$, —S(O)R$^{11}$, —S(O)$_2$R$^{12}$, —S(O)$_2$NR$^{11}$R$^{12}$, C$_1$-C$_8$ haloalkyl, COR$^{13}$, —C(O)OR$^{12}$, —C(O)NR$^{11}$R$^{12}$, —C(O)R$^{12}$, —NR$^{11}$R$^{12}$, —NR$^{11}$C(O)R$^{12}$, —NR$^{11}$S(O)$_2$R$^{12}$, —NR$^{11}$C(O)OR$^{12}$, —B(OH)$_2$, C$_1$-C$_8$ alkyl, C$_3$-C$_8$ cycloalkyl, C$_2$-C$_8$ alkenyl, C$_2$-C$_8$ alkynyl, substituted or unsubstituted aryl, substituted or unsubstituted heteroaryl, -alkylC(O)—OR$^{12}$, -alkylC(O)NR$^{11}$R$^{12}$, -alkenylC(O)OR$^{12}$, -alkenylC(O)NR$^{11}$R$^{12}$, -aryl(CH$_2$)$_m$C(O)OR$^{12}$, -aryl(CH$_2$)$_m$C(O)NR$^{11}$R$^{12}$, —(CH$_2$)$_m$C(O)NR$^{11}$S(O)$_2$R$^{12}$, -aryl(CH$_2$)$_m$—C(O)NR$^{11}$S(O)$_2$R$^{12}$, —(CH$_2$)$_m$S(O)$_2$NR$^{11}$C(O)R$^{12}$, -aryl(CH$_2$)$_m$S(O)$_2$NR$^{11}$C(O)R$^{12}$, or substituted or unsubstituted heterocycle or substituted or unsubstituted heteroaryl containing 1 to 4 heteroatoms, optionally substituted with 1 to 2 substituents selected from the group consisting of H, hydroxyl, halogen, CF$_3$, C$_1$-C$_8$ alkyl, C$_1$-C$_8$ alkoxy, cyano, amino, C$_1$-C$_8$ alkylamino, and C$_1$-C$_8$ alkoxyC$_1$-C$_8$ alkylamino provided at least one of R$^4$, R$^5$, R$^6$, R$^7$, or R$^8$ is other than hydrogen;

R$^{10}$, R$^{11}$, R$^{12}$, and R$^{13}$ are each individually selected from the group consisting of H, C$_1$-C$_8$ alkyl, C$_1$-C$_8$ haloalkyl, C$_1$-C$_8$ alkylaryl, C$_{2-8}$ alkenyl, C$_{2-8}$ alkynyl, cycloalkyl, substituted or unsubstituted aryl, substituted or unsubstituted heteroaryl, or heterocycle;

m=0 to 6;

wherein alkyl, alkenyl, alkynyl, cycloalkyl, aryl, heteroaryl or heterocycle may be substituted or unsubstituted; pharmaceutically acceptable salt thereof solvate thereof and deuterated form thereof to a subject in need thereof.

18. A method for treating a patient against HIV-1 infection by administering to a patient in need thereof a therapeutically effective amount of a compound according to claim 1, pharmaceutically acceptable salt thereof or solvate.

19. The compound according to claim 8 being selected from the group consisting of

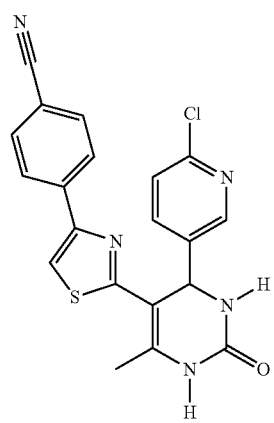

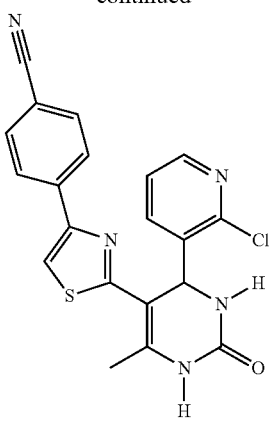
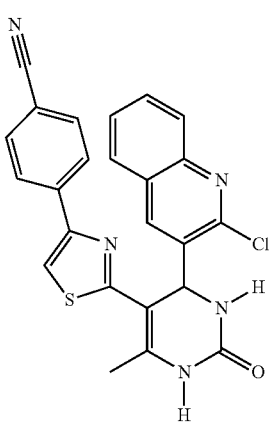
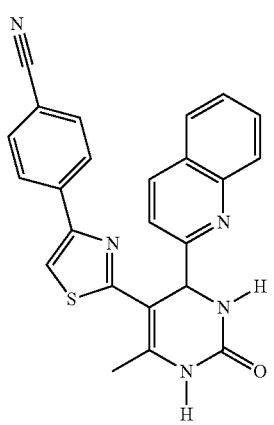
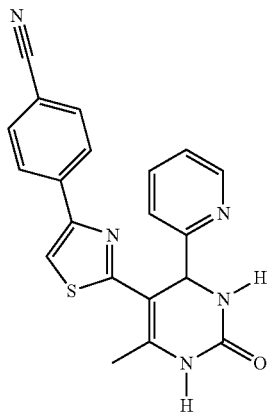
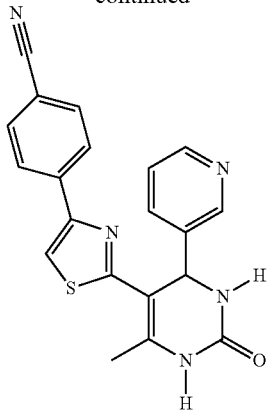
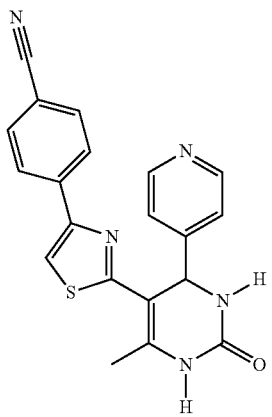
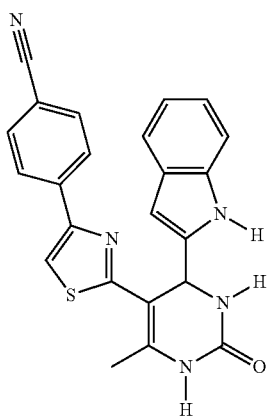
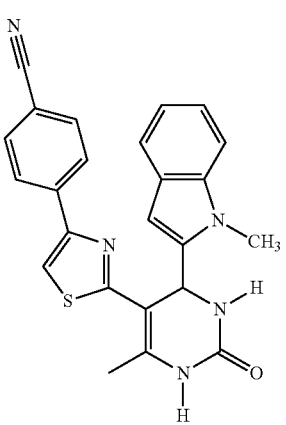

117
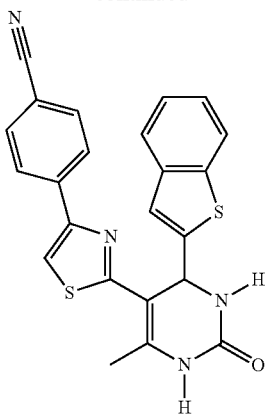
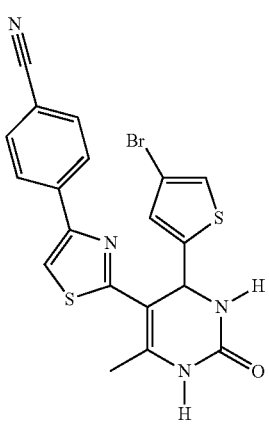
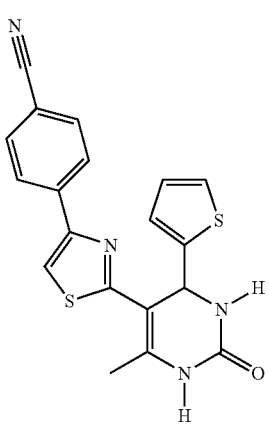
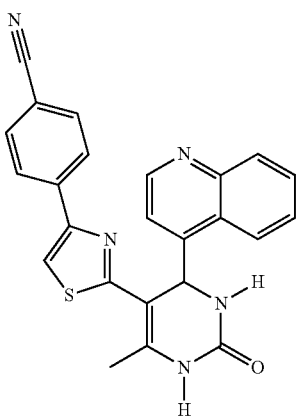
118
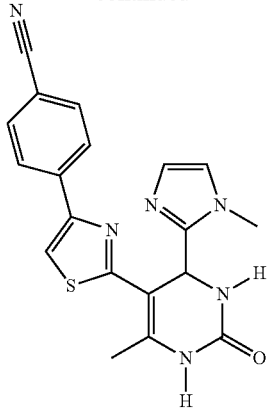
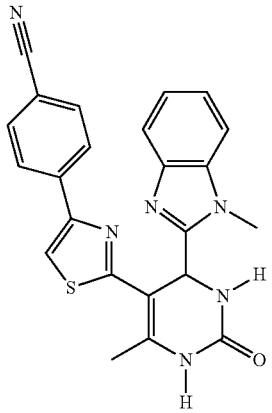
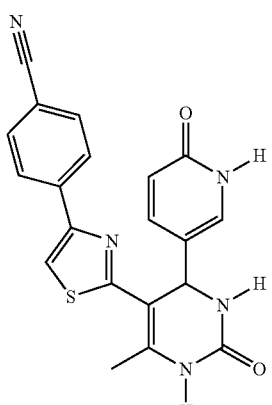
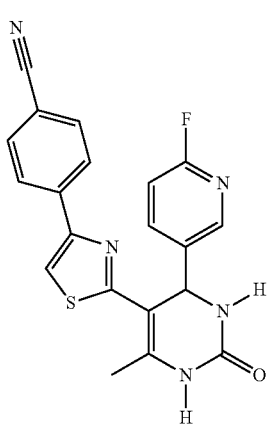

119
-continued
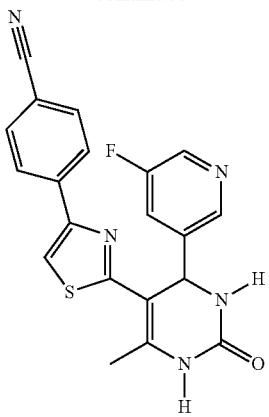
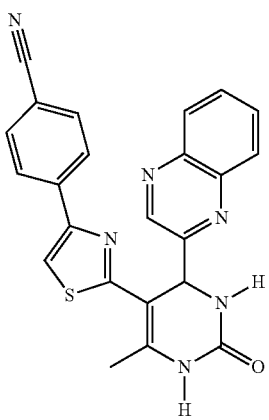
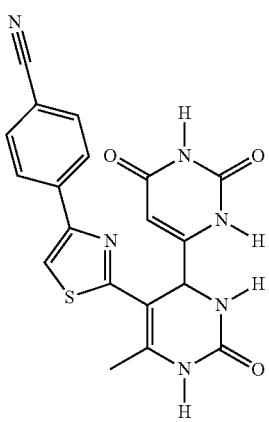
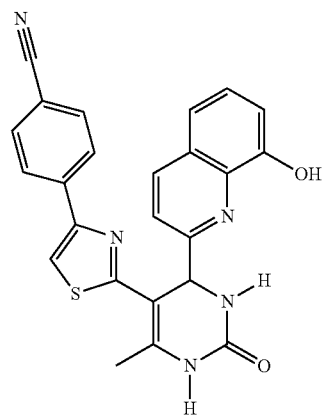
120
-continued
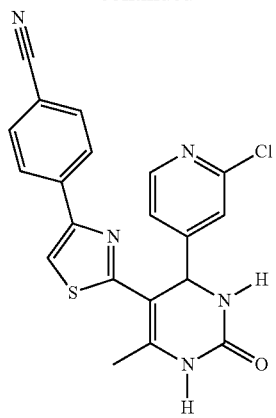
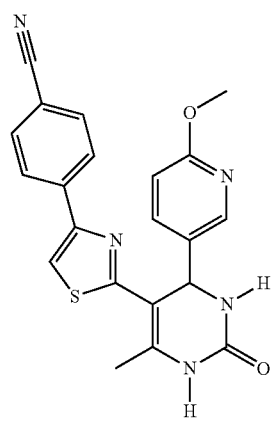
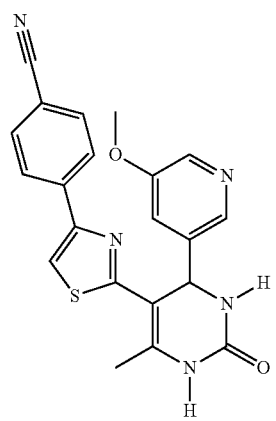
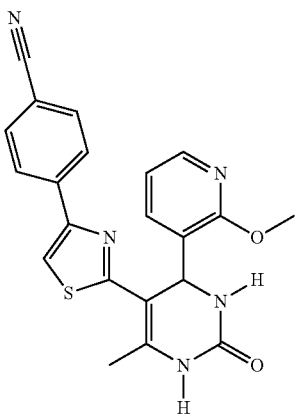

121
-continued
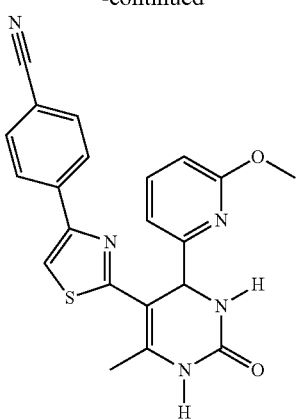
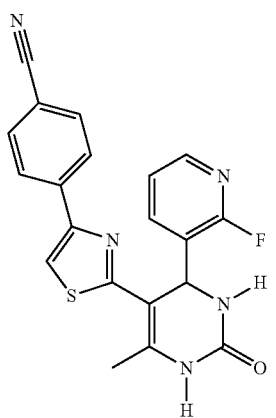
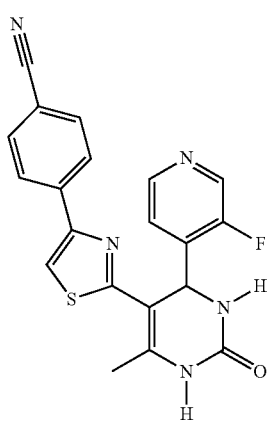
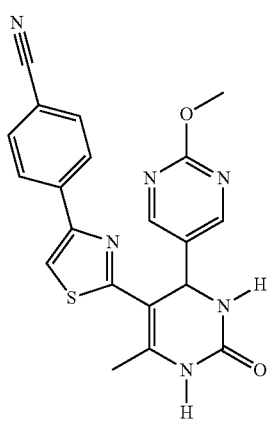
122
-continued
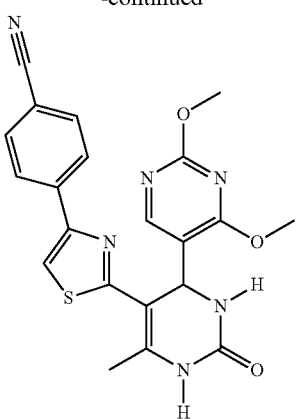
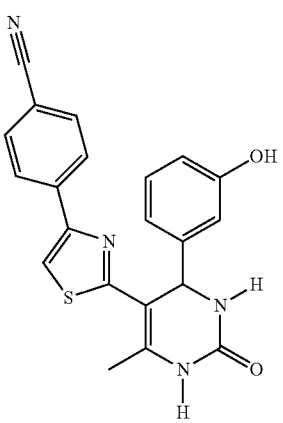
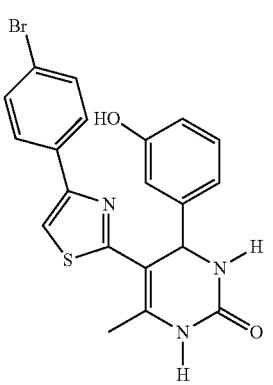
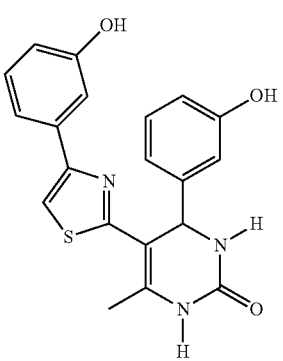

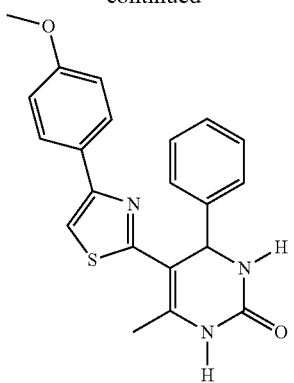
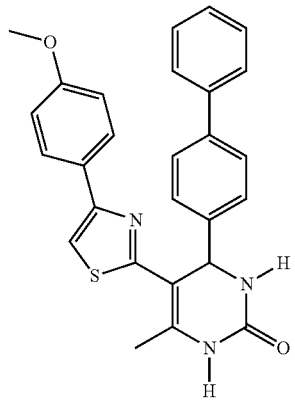
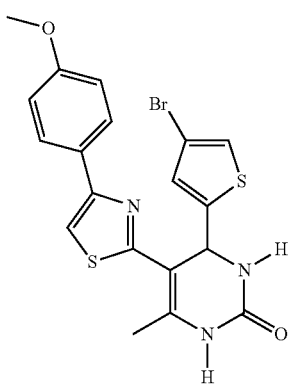
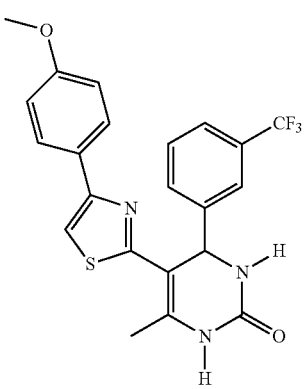
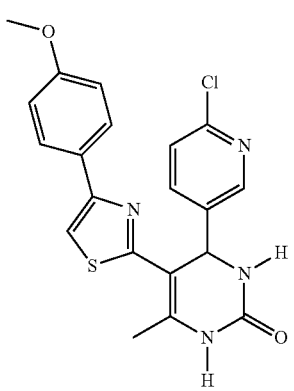
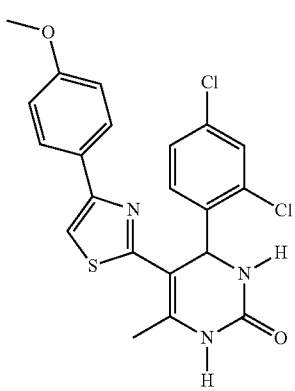
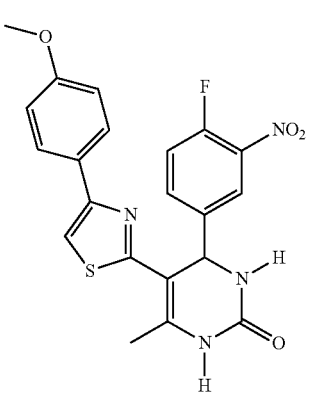
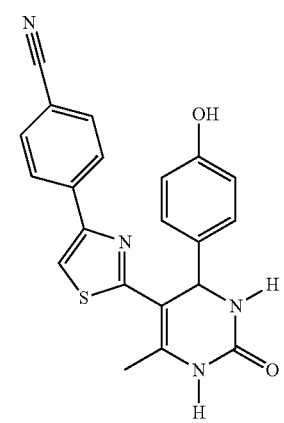

125
-continued
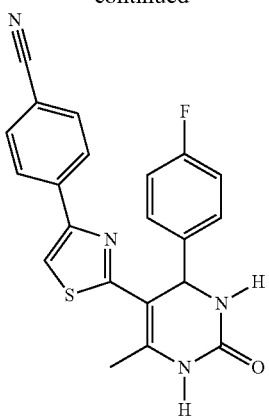
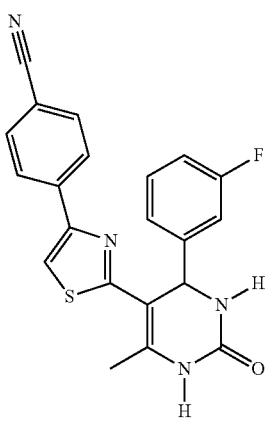
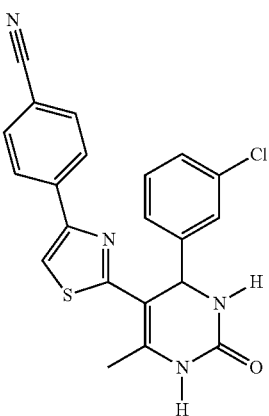
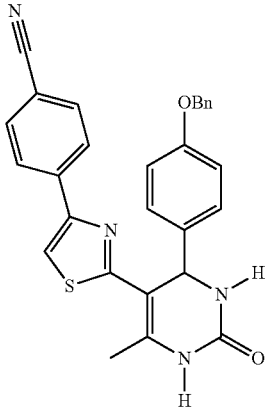
126
-continued
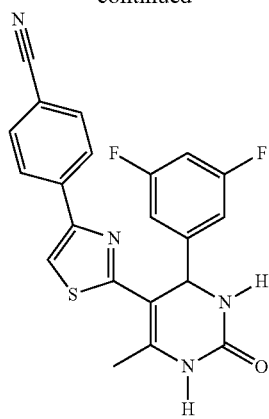
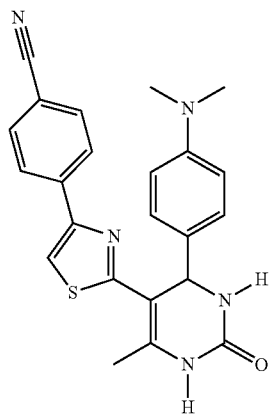
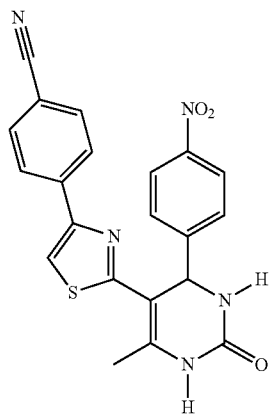
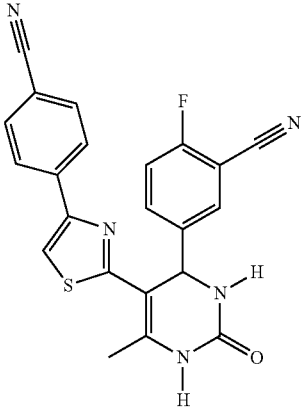

127
-continued
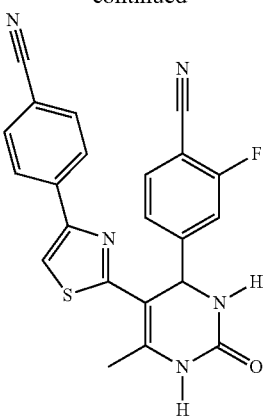
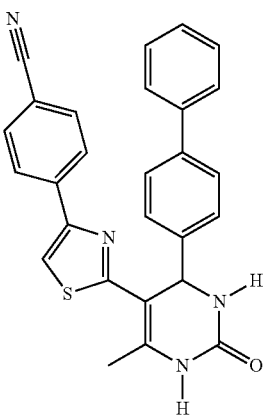
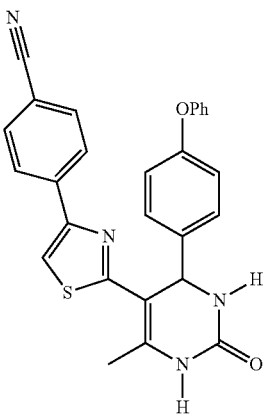
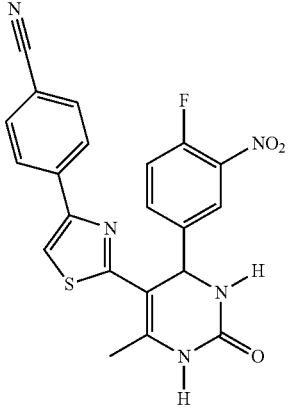
128
-continued
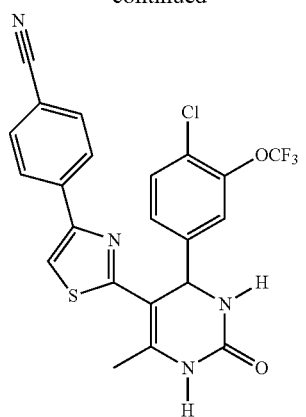
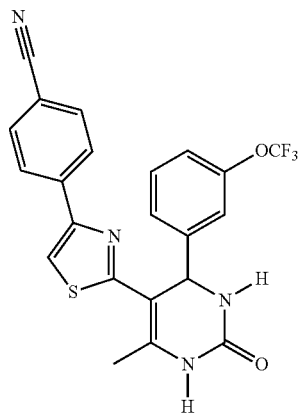
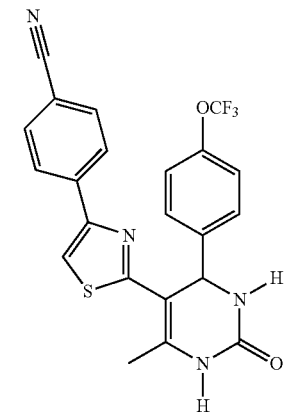
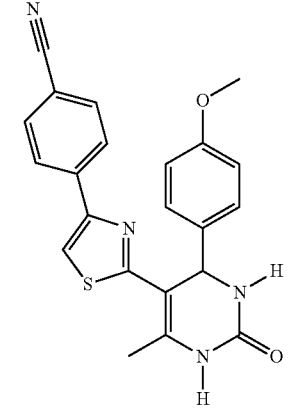

129
-continued
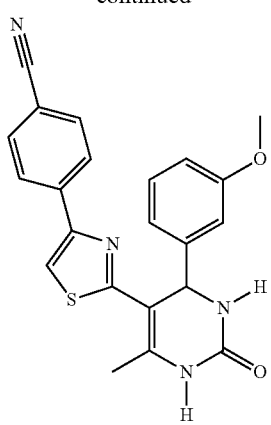
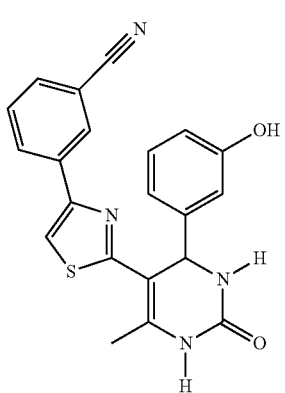
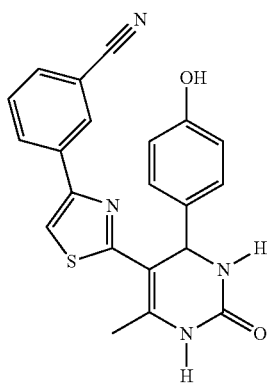
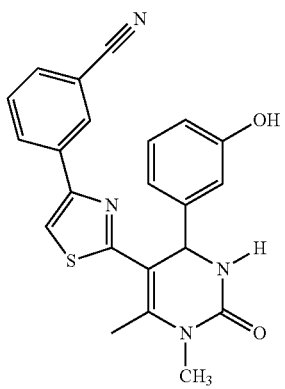
130
-continued
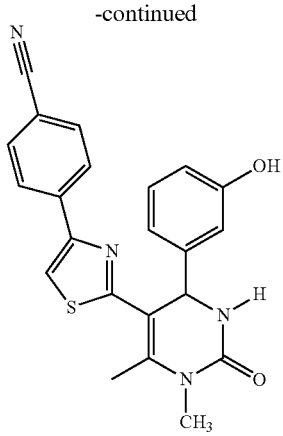
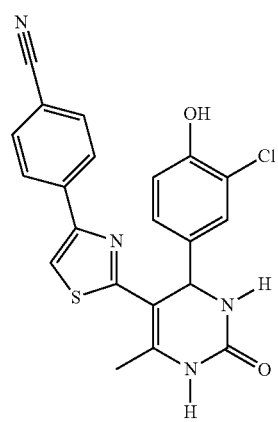
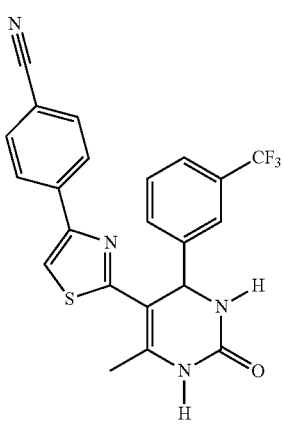
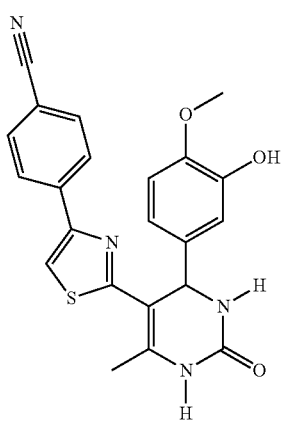

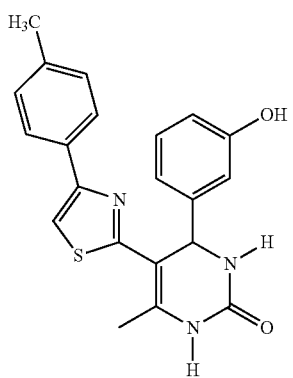
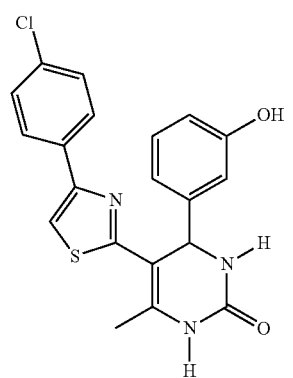
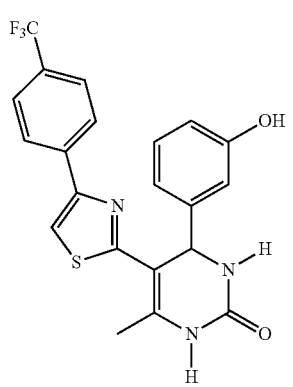
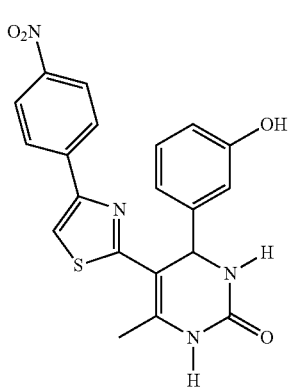
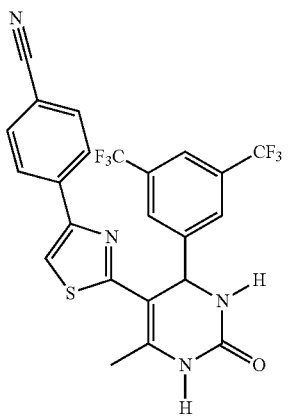
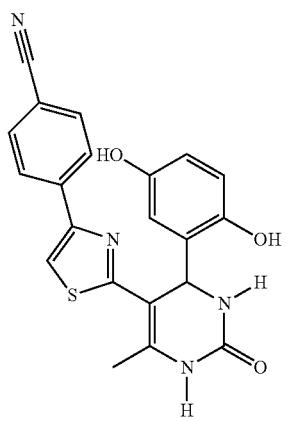
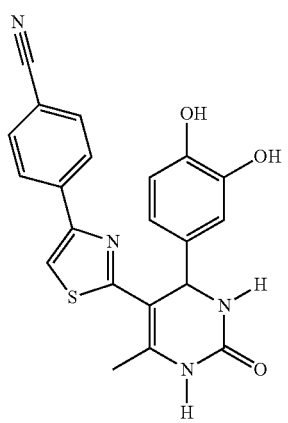
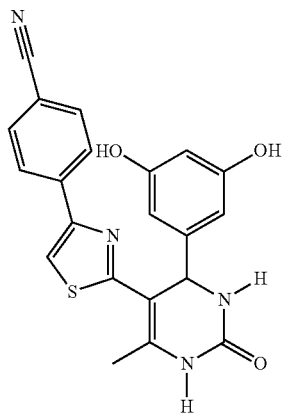

133
-continued
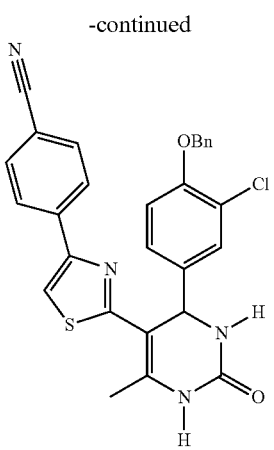
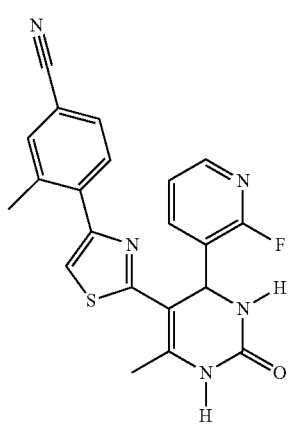
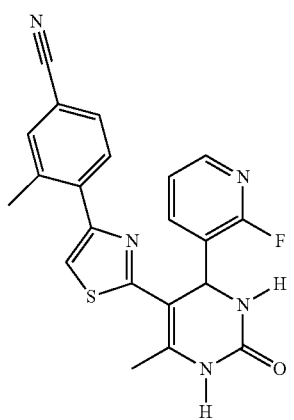
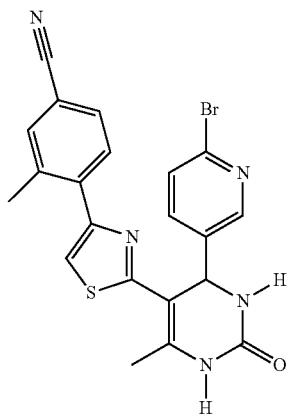
134
-continued
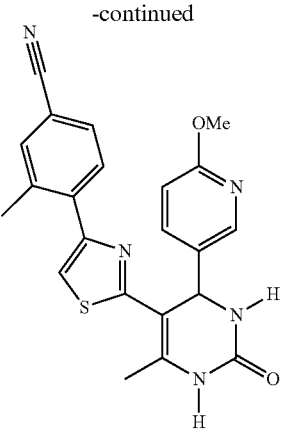
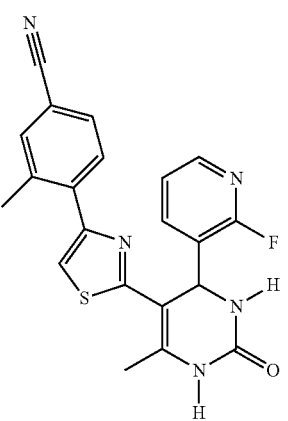
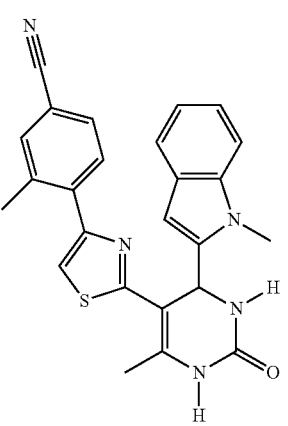
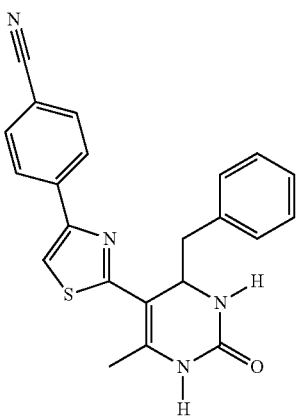

135
-continued
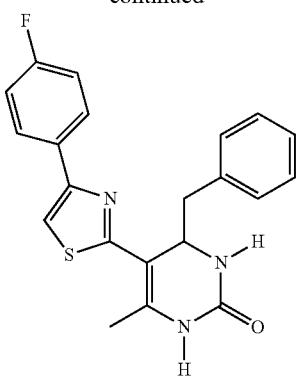
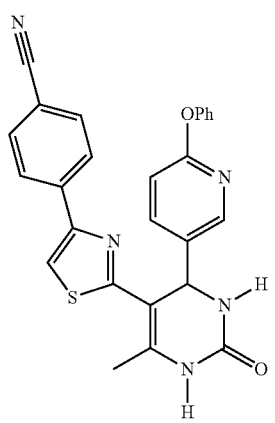
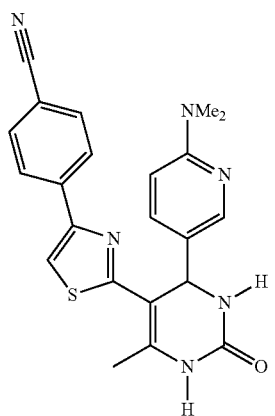
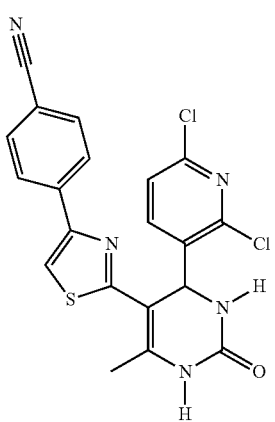
136
-continued
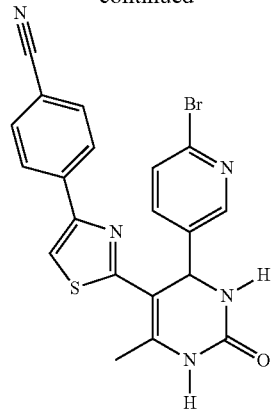
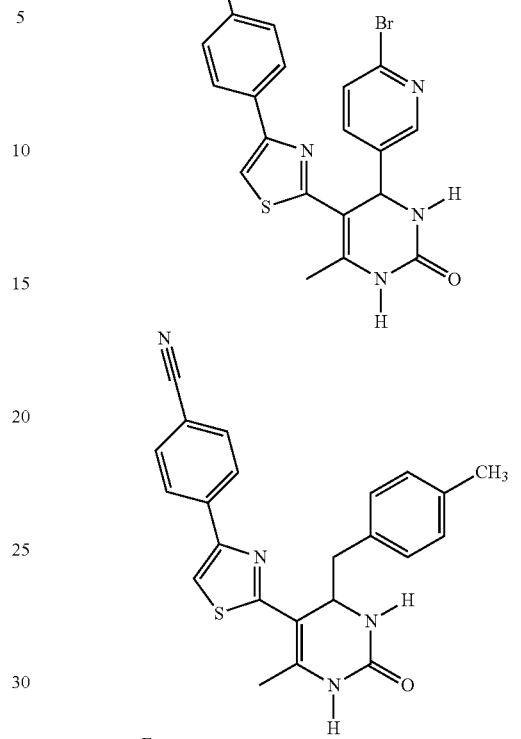
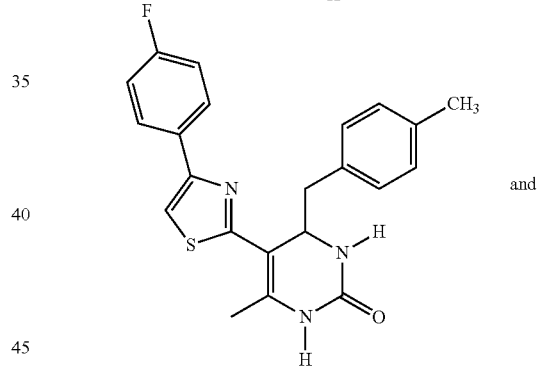
and
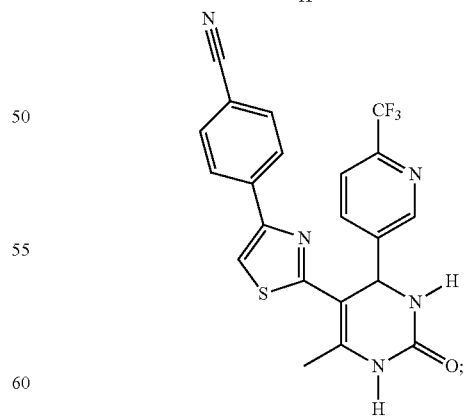
pharmaceutically acceptable salts thereof; solvates thereof and deuterated form thereof.
* * * * *